US007589179B2

(12) United States Patent
Gillies et al.

(10) Patent No.: US 7,589,179 B2
(45) Date of Patent: Sep. 15, 2009

(54) IL-7 VARIANTS WITH REDUCED IMMUNOGENICITY

(75) Inventors: Stephen D. Gillies, Carlisle, MA (US); Jeffrey Way, Cambridge, MA (US)

(73) Assignee: Merck Patent GmbH, Darmstadt (DE)

( * ) Notice: Subject to any disclaimer, the term of this patent is extended or adjusted under 35 U.S.C. 154(b) by 272 days.

(21) Appl. No.: 11/297,166

(22) Filed: Dec. 8, 2005

(65) Prior Publication Data

US 2006/0141581 A1 Jun. 29, 2006

Related U.S. Application Data

(60) Provisional application No. 60/634,470, filed on Dec. 9, 2004.

(51) Int. Cl.
*C07K 16/00* (2006.01)
*C12P 21/08* (2006.01)
*C07K 17/00* (2006.01)
*A61K 39/00* (2006.01)

(52) U.S. Cl. ................. 530/387.1; 530/387.3; 530/351; 424/134.1; 424/178.1; 424/192.1

(58) Field of Classification Search ....................... None
See application file for complete search history.

(56) References Cited

U.S. PATENT DOCUMENTS

| | | | |
|---|---|---|---|
| 4,196,265 | A | 4/1980 | Koprowski et al. |
| 4,469,797 | A | 9/1984 | Albarella |
| 4,676,980 | A | 6/1987 | Segal et al. |
| 5,019,368 | A | 5/1991 | Epstein et al. |
| 5,082,658 | A | 1/1992 | Palladino |
| 5,091,513 | A | 2/1992 | Huston et al. |
| 5,114,711 | A | 5/1992 | Bell et al. |
| 5,116,964 | A | 5/1992 | Capon et al. |
| 5,225,538 | A | 7/1993 | Capon et al. |
| 5,258,498 | A | 11/1993 | Huston et al. |
| 5,314,995 | A | 5/1994 | Fell, Jr. et al. |
| 5,349,053 | A | 9/1994 | Landolfi |
| 5,359,035 | A | 10/1994 | Habermann |
| 5,399,346 | A | 3/1995 | Anderson et al. |
| 5,428,130 | A | 6/1995 | Capon et al. |
| 5,480,981 | A | 1/1996 | Goodwin et al. |
| 5,514,582 | A | 5/1996 | Capon et al. |
| 5,541,087 | A | 7/1996 | Lo et al. |
| 5,601,819 | A | 2/1997 | Wong et al. |
| 5,609,846 | A | 3/1997 | Goldenberg |
| 5,614,184 | A | 3/1997 | Sytkowski et al. |
| 5,624,821 | A | 4/1997 | Winter et al. |
| 5,645,835 | A | 7/1997 | Fell, Jr. et al. |
| 5,650,150 | A | 7/1997 | Gillies |
| 5,677,425 | A | 10/1997 | Bodmer et al. |
| 5,679,543 | A | 10/1997 | Lawlis |
| 5,709,859 | A | 1/1998 | Aruffo et al. |
| 5,723,125 | A | 3/1998 | Chang et al. |
| 5,726,044 | A | 3/1998 | Lo et al. |
| 5,728,552 | A | 3/1998 | Fujisawa et al. |
| 5,770,195 | A | 6/1998 | Hudziak et al. |
| 5,827,516 | A | 10/1998 | Urban et al. |
| 5,827,703 | A | 10/1998 | Debs et al. |
| 5,843,423 | A | 12/1998 | Lyman et al. |
| 5,908,626 | A | 6/1999 | Chang et al. |
| 6,086,875 | A | 7/2000 | Blumberg et al. |
| 6,100,387 | A | 8/2000 | Herrmann et al. |
| 6,156,301 | A | 12/2000 | Namen et al. |
| 6,169,070 | B1 | 1/2001 | Chen et al. |
| 6,277,375 | B1 | 8/2001 | Ward |
| 6,281,010 | B1 | 8/2001 | Gao et al. |
| 6,284,536 | B1 | 9/2001 | Morrison et al. |
| 6,335,176 | B1 | 1/2002 | Inglese et al. |
| 6,444,792 | B1 | 9/2002 | Gray et al. |
| 6,475,717 | B1 | 11/2002 | Enssle et al. |
| 6,485,726 | B1 | 11/2002 | Blumberg et al. |
| 6,500,641 | B1 | 12/2002 | Chen et al. |
| 6,551,592 | B2 | 4/2003 | Lindhofer et al. |
| 6,617,135 | B1 | 9/2003 | Gillies et al. |
| 6,620,413 | B1 | 9/2003 | DeSauvage et al. |
| 6,627,615 | B1 | 9/2003 | Debs et al. |
| 6,646,113 | B1 | 11/2003 | Dreyfuss et al. |
| 6,696,517 | B2 | 2/2004 | Gillies et al. |
| 6,750,329 | B1 | 6/2004 | Rosenblum et al. |
| 6,838,260 | B2 | 1/2005 | Gillies et al. |
| 6,992,174 | B2 | 1/2006 | Gillies et al. |
| 7,067,110 | B1 | 6/2006 | Gillies et al. |

(Continued)

FOREIGN PATENT DOCUMENTS

AU 21725/88 3/1989

(Continued)

OTHER PUBLICATIONS

Bowie et al, 1990, Science 247:1306-1310.*

(Continued)

*Primary Examiner*—Manjunath Rao
*Assistant Examiner*—Shulamith H Shafer
(74) *Attorney, Agent, or Firm*—Goodwin Procter LLP

(57) ABSTRACT

Modified interleukin-7 (IL-7) polypeptides are disclosed. The modified IL-7 polypeptides have alterations to one or more potential T-cell epitopes, thereby to reduce a T-cell response.

8 Claims, 10 Drawing Sheets

U.S. PATENT DOCUMENTS

| | | | |
|---|---|---|---|
| 7,091,321 | B2 | 8/2006 | Gillies et al. |
| 7,141,651 | B2 | 11/2006 | Gillies et al. |
| 7,148,321 | B2 | 12/2006 | Gillies et al. |
| 7,169,904 | B2 | 1/2007 | Gillies et al. |
| 2001/0053539 | A1 | 12/2001 | Lauffer et al. |
| 2002/0037558 | A1 | 3/2002 | Lo et al. |
| 2002/0081664 | A1 | 6/2002 | Lo et al. |
| 2002/0142374 | A1 | 10/2002 | Gallo et al. |
| 2002/0146388 | A1 | 10/2002 | Gillies |
| 2002/0147311 | A1 | 10/2002 | Gillies et al. |
| 2002/0192222 | A1 | 12/2002 | Blumberg et al. |
| 2002/0193570 | A1 | 12/2002 | Gillies et al. |
| 2003/0003529 | A1 | 1/2003 | Bayer |
| 2003/0012789 | A1 | 1/2003 | Blumberg et al. |
| 2003/0044423 | A1 | 3/2003 | Gillies et al. |
| 2003/0049227 | A1 | 3/2003 | Gillies et al. |
| 2003/0105294 | A1 | 6/2003 | Gillies et al. |
| 2003/0139365 | A1 | 7/2003 | Lo et al. |
| 2003/0139575 | A1 | 7/2003 | Gillies |
| 2003/0157054 | A1 | 8/2003 | Gillies et al. |
| 2003/0166163 | A1 | 9/2003 | Gillies |
| 2003/0166877 | A1 | 9/2003 | Gillies et al. |
| 2004/0013640 | A1 | 1/2004 | Zardi et al. |
| 2004/0033210 | A1 | 2/2004 | Gillies |
| 2004/0043457 | A1 | 3/2004 | Schumacher et al. |
| 2004/0053366 | A1 | 3/2004 | Lo et al. |
| 2004/0072299 | A1 | 4/2004 | Gillies et al. |
| 2004/0082039 | A1 | 4/2004 | Gillies et al. |
| 2004/0180035 | A1 | 9/2004 | Gillies et al. |
| 2004/0180386 | A1 | 9/2004 | Carr et al. |
| 2004/0203100 | A1 | 10/2004 | Gillies et al. |
| 2005/0042729 | A1 | 2/2005 | Lo et al. |
| 2005/0069521 | A1 | 3/2005 | Gillies et al. |
| 2005/0137384 | A1 | 6/2005 | Gillies et al. |
| 2005/0164352 | A1 | 7/2005 | Lauder et al. |
| 2005/0192211 | A1 | 9/2005 | Gillies et al. |
| 2005/0202021 | A1 | 9/2005 | Gillies |
| 2005/0244418 | A1 | 11/2005 | Gillies et al. |
| 2005/0261229 | A1 | 11/2005 | Gillies et al. |
| 2006/0025573 | A1 | 2/2006 | Gillies et al. |
| 2006/0034836 | A1 | 2/2006 | Gillies et al. |
| 2006/0141581 | A1 | 6/2006 | Gillies et al. |
| 2006/0194952 | A1 | 8/2006 | Gillies et al. |
| 2006/0228332 | A1 | 10/2006 | Gillies et al. |
| 2006/0263856 | A1 | 11/2006 | Gillies et al. |

FOREIGN PATENT DOCUMENTS

| | | | |
|---|---|---|---|
| EP | 0 294 703 | A2 | 12/1988 |
| EP | 0 308 936 | B1 | 3/1989 |
| EP | 0 314 317 | B1 | 3/1989 |
| EP | 0 318 554 | B1 | 6/1989 |
| EP | 0 326 120 | B1 | 8/1989 |
| EP | 0 350 230 | A2 | 1/1990 |
| EP | 0 375 562 | B1 | 6/1990 |
| EP | 0 396 387 | A2 | 11/1990 |
| EP | 0 439 095 | A2 | 7/1991 |
| EP | 0 511 747 | A1 | 11/1992 |
| EP | 0 519 596 | | 12/1992 |
| EP | 0 601 043 | B1 | 6/1994 |
| EP | 0 699 755 | | 3/1996 |
| EP | 0 428 596 | B1 | 4/1996 |
| EP | 0 706 799 | A2 | 4/1996 |
| EP | 1 088 888 | A1 | 4/2001 |
| WO | WO 86/01533 | | 3/1986 |
| WO | WO 88/00052 | | 1/1988 |
| WO | WO 88/09344 | | 12/1988 |
| WO | WO 89/02922 | | 4/1989 |
| WO | WO 89/09620 | | 10/1989 |
| WO | WO 91/00360 | | 1/1991 |
| WO | WO 91/04329 | | 4/1991 |
| WO | WO 91/08298 | | 6/1991 |
| WO | WO 91/13166 | | 9/1991 |
| WO | WO 91/14438 | | 10/1991 |
| WO | WO 92/02240 | | 2/1992 |
| WO | WO 92/08495 | | 5/1992 |
| WO | WO 92/08801 | | 5/1992 |
| WO | WO 92/10755 | | 6/1992 |
| WO | WO 92/16562 | | 10/1992 |
| WO | WO 93/03157 | | 2/1993 |
| WO | WO 94/25609 | | 11/1994 |
| WO | WO 95/05468 | | 2/1995 |
| WO | WO 95/21258 | | 8/1995 |
| WO | WO 95/31483 | | 11/1995 |
| WO | WO 96/04388 | | 2/1996 |
| WO | WO 96/08570 | | 3/1996 |
| WO | WO 96/18412 | | 6/1996 |
| WO | WO 96/40792 | | 12/1996 |
| WO | WO 97/00317 | | 1/1997 |
| WO | WO 97/00319 | | 1/1997 |
| WO | WO 97/24137 | | 7/1997 |
| WO | WO 97/24440 | | 7/1997 |
| WO | WO 97/30089 | | 8/1997 |
| WO | WO 97/33617 | | 9/1997 |
| WO | WO 97/33619 | | 9/1997 |
| WO | WO 97/34631 | | 9/1997 |
| WO | WO 97/43316 | | 11/1997 |
| WO | WO 98/00127 | | 1/1998 |
| WO | WO 98/28427 | | 7/1998 |
| WO | WO 98/30706 | | 7/1998 |
| WO | WO 98/46257 | | 10/1998 |
| WO | WO 98/52976 | | 11/1998 |
| WO | WO 98/59244 | | 12/1998 |
| WO | WO 99/02709 | | 1/1999 |
| WO | WO 99/03887 | | 1/1999 |
| WO | WO 99/29732 | | 6/1999 |
| WO | WO 99/43713 | | 9/1999 |
| WO | WO 99/52562 | | 10/1999 |
| WO | WO 99/53958 | | 10/1999 |
| WO | WO 01/07081 | | 2/2000 |
| WO | WO 00/11033 | | 3/2000 |
| WO | WO 00/34317 | | 6/2000 |
| WO | WO 00/40615 | | 7/2000 |
| WO | WO 00/69913 | | 11/2000 |
| WO | WO 01/10912 | | 2/2001 |
| WO | WO 01/36489 | | 5/2001 |
| WO | WO 01/58957 | | 8/2001 |
| WO | WO 02/02143 | | 1/2002 |
| WO | WO 02/066514 | | 8/2002 |
| WO | WO 02/072605 | | 9/2002 |
| WO | WO 02/079232 | | 10/2002 |
| WO | WO 02/090566 | | 11/2002 |
| WO | WO 03/015697 | | 2/2003 |
| WO | WO 03/048334 | | 6/2003 |
| WO | WO 03/077834 | | 9/2003 |

OTHER PUBLICATIONS

Sequence Q95J83, submitted by Gregoire et al to the EMBL/GenBank/DDBJ databases on Jul. 1991, downloaded Mar. 10, 2008.*

International Search Report for International Application Serial No. PCT/EP2005/013145, mailed Nov. 28, 2006 (5 pages).

Written Opinion for International Application Serial No. PCT/EP2005/013145, mailed Nov. 28, 2006 (9 pages).

"Bos Taurus IL-7 mRNA, complete cds." EMBL Database, EBI accession No. AF348422, Dec. 4, 2002.

"Ovis aries interleukin-7 (IL-7), complete cds." EMBL Database, EBI accession No. U10089, Jun. 8, 1994.

Alpdogan et al., (2005), "IL-7 and IL-15: therapeutic cytokines for immunodeficiency," *Trends in Immunology*, 26(1):56-64.

Storek et al., (2003), "Interleukin-7 improves CD4 T-cell reconstitution after autologous CD34 cell transplantation in monkeys," *Blood*, 101(10):4209-4218.

Anderson et al., (1980), "Characterization of the Fc Receptor for IgG on a Human Macrophage Cell Line U937," *J. Immunol.*, 125(6):2735-41.
Angal et al., (1993), "A Single Amino Acid Substitution Abolishes the Heterogeneity of Chimeric Mouse/Human (IgG4) Antibody," *Molecular Immunology*, 30(1):105-108.
Baici et al., (1980), "Kinetics of the Different Susceptibilities of the Four Human Immunoglobulin G Subclasses to Proteolysis by Human Lysosomal Elastase," *Scand. J. Immunol.* 12(1):41-50.
Batova et al., (1999), "The Ch14.18-GM-CSF Fusion Protein is Effective at Mediating Antibody-Dependent Cellular Cytotoxicity and Complement-Dependent Cytotoxicity in Vitro," *Clinical Cancer Research*, 5:4259-4263.
Batra et al., (1993), "Insertion of Constant Region Domains of Human IgG1 into CD4-PE40 Increases Its Plasma Half-Life," *Molecular Immunology*, 30(4):379-386.
Becker et al., (1996), "An Antibody-Interleukin 2 Fusion Protein Overcomes Tumor Heterogeneity by Induction of a Cellular Immune Response," *Proc. Natl. Acad. Sci. USA*, 93:7826-7831.
Becker et al., (1996), "Eradiction of Human Hepatic and Pulmonary Melanoma Metastases in SCID Mice by Antibody-Interleukin 2 Fusion Proteins," *Proc. Natl. Acad. Sci. USA*, 93:27202-2707.
Becker et al., (1996), "Long-Lived and Transferable Tumor Immunity in Mice after Targeted Interleukin-2 Therapy," *J. Clin. Invest.*, 98(12):2801-2804.
Becker et al., (1996), "T Cell-Mediated Eradicated of Murine Metastatic Melanoma Induced by Targeted Interleukin-2 Therapy," *J. Exp. Med.*, 183(50):2361-2366.
Beutler et al., (1988), "Tumor Necrosis, Cachexia, Shock, and Inflammation: A Common Mediator," *Annual Rev. Biochem.*, 57:505-518.
Bitonti et al., (2002), "Transepithelail Absorption of an Erythropoietin-Fc Fusion Protein After Delivery to the Central Airways," *Respiratory Drug Delivery*, 8:309-312.
Botonti et al. (2004), "Pulmonary Delivery of an Erythropoietin Fc Fusion Protein in Non-Human Primates Through an Immunoglobulin Transport Pathway," *Proc. Natl. Acad. Sci. USA*101(26):9763-9768.
Bjorn et al., (1985), "Evaluation of Monoclonal Antibodies for the Development of Breast Cancer Immunotoxins," *Cancer Research*, 45:1214-1221.
Boulianne et al., (1984), "Production of Functional Chimaeric Mouse/Human Antibody," *Nature*, 312:643-6.
Bourgois et al., (1974), "Determination of the Primary Structure of a Mouse IgG2a Immunoglobulin: Amino-Acid Sequence of the Fc Fragment: Implications for the Evolution of Immunoglobulin Structure and Function," *Eur. J. Biochem.*, 43:423-35.
Brambell et al., (1964), "A Theoretical Model of γ-Globulin Catabolism," *Nature*, 203:1352-55.
Brekke et al., (1994), "Human IgG Isotype-Specific Amino Acid Residues Affecting Complement-Mediated Cell Lysis and Phagocytosis," *Eur. J. Immunol.*, 24:2542-2547.
Bubenik et al., (1995), "Interleukin-2 Gene Therapy of Residual EL-4 Leukaemia Potentiates the Effect of the Cyclophosphamide Pretreatment," *J. Cancer Res. Clin. Oncol.*, 121:39-43.
Burgess et al., (1990), "Possible Dissociation of the Heparin-Binding Mitogenic Activities of Heparin-Binding (Acidic Fibroblast) Growth Factor-1 from Its Receptor-Binding Activities by Site-Directed Mutagenesis of a Single Lysine Residue," *Journal of Cell Biology*, 111:2129-2138.
Canfield et al., (1991), "The Binding Affinity of Human IgG for its High Affinity Fc Receptor is Determined by Multiple Amino Acids in the CH2 Domain and is Modulated by the Hinge Region," *J. Exp. Med.*, 173(6):1483-1491.
Capon et al., (1989), "Designing CD4 Immunoadhesins for AIDS Therapy," *Nature*, 337:525-531.
Caton et al., (1986), "Structural and Functional Implications of a Restricted Antibody Response to a Defined Antigenic Region on the Influenza Virus Hemagglutinin," *The EMBO Journal*, 5(7):1577-1587.
Chan et al., (1992), "Mechanisms of IFN-γ Induction by Natural Killer Cell Stimulatory Factor (NKSF/IL-12). Role of Transcription and mRNA Stability in the Synergistic Interaction Between NKSF and IL-2," *J. Immunol.*, 148:92-98.
Chapman et al., (1994), "Mapping Effector Functions of a Monoclonal Antibody to GD3 by Characterization of a Mouse-Human Chimeric Antibody," *Cancer Immuno. Immunother.*, 39:198-204.
Chappel et al., (1991), "Identification of the Fc Gamma Receptor Class I Binding Site In Human IgG Through Use of Recombinant IgG1/IgG2 Hybrid and Point-Mutated Antibodies," *Proc. Natl. Acad. Sci. USA*, 88(20):9036-40.
Chaudhary et al., (1988), "Selective Killing of HIV-Infected Cells by Recombinant Human CD4-*Pseudomonas* Exotoxin Hybrid Protein," *Nature*, 335:370-372.
Chaudhary et al., (1989), "A Recombinant Immunotoxin Consisting of Two Antibody Variable Domains Fused to *Pseudomonas* Exotoxin," *Nature*, 339:394-397.
Cheon et al., (1994), "High-Affinity Binding Sites for Related Fibroblast Growth Factor Ligands Reside Within Different Receptor Immunoglobulin-Like Domains," *Proc. Natl. Acad. Sci. USA*, 91:989-993.
Cohen et al., (1998), "An Artificial Cell-Cycle Inhibitor Isolated From a Combinatorial Library," *Proc. Natl. Acad. Sci. USA*, 95:14272-7.
Cole et al., (1997), "Human IgG2 Variants of Chimeric Anti-CD3 Are Nonmitogenic to T Cells," *Journal of Immunology*, 159:3613-3621.
Connor et al., (2004), "Ex vivo Evaluation of Anti-EpCAM Immunocytokine huKS-IL2 in Ovarian Cancer," *J. Immunotherapy*, 27:211-219.
Cosenza et al., (1997), "Disulfide Bond Assignment in Human Interleukin-7 by Matrix-Assisted Laser Desorption/Ionization Mass Spectroscopy and Site-Directed Cysteine to Serine Mutational Analysis," *J. Biol. Chem.*, 272:32995-3000.
Cruse et al., (eds.), (1995), *Illustrated Dictionary of Immunology*, pp. 156-158, CRC Press, NY.
Davis et al., (2003), "Immunocytokines: Amplification of Anti-Cancer Immunity," *Cancer Immunol. Immunother.*, 52:297-308.
de la Salle et al., (1996), "FCγR on Human Dendritic Cells," in *Human IgG Receptors*, pp. 39-55, van de Winkel et al. (eds.), R.G. Landes Co.
Dolman et al., (1998), "Suppression of Human Prostate Carcinoma Metastases in Severe Combined Immunodeficient Mice by Interleukin 2 Immunocytokine Therapy," *Clin. Cancer Research.*, 4(10:2551-2557.
Dorai et al., (1991), "Aglycosylated Chimeric Mouse/Human IgG1 Antibody Retains Some Effector Function," *Hybridoma*, 10(2):211-217.
Dorai et al., (1992), "Role of Inter-Heavy and Light Chain Disulfide Bonds in the Effector Functions of Human IgG1," *Molecular Immunology*, 29(12):1487-1491.
Duncan et al., (1988), "The Binding Site for C1q on IgG," *Nature*, 332:738-740.
Ellison et al., (1982), "The Nucleotide Sequence of a Human Immunoglobulin C $\gamma_1$ Gene," *Nucleic Acids Res.*, 10:4071-9.
Fell et al., (1991), "Genetic Construction and Characterization of a Fusion Protein Consisting of a Chimeric F(ab') with Specificity for Carcinomas and Human IL-2," *J. Immunology*, 146(7):2446-2452.
Fell et al., (1992), "Chimeric L6 Anti-Tumor Antibody: Genomic Construction, Expression, and Characterization of the Antigen Binding Site," *J. Biological Chemistry*, 267:15552-15558.
Frost et al., (1997), "A Phase I/IB Trial of Murine Monoclonal Anti-GD2 Antibody 14.G2a Plus Interleukin-2 in Children with Refractory Neuroblastoma," *Cancer*, 80(2):317-333.
Fry et al., (2003), "IL-7 Therapy Dramatically Alters Peripheral T-Cell Homeostasis in Normal and SIV-Infected Non-Human Primates," *Blood*, 101:2294-9.
Gan et al., (1999), "Specific Enzyme-Linked Immunosorbent Assays for Quantitation of Antibody-Cytokine Fusion Proteins," *Clinical and Diagnostic Laboratory Immunology*, 6(2):236-42.
Gasson et al., (1984), "Purified Human Granulocyte Macrophage Colony-Stimulating Factor: Direct Action on Neutrophils," *Science*, 226:1339-1342.

Ghetie et al., (1997), "FcRn: The MHC Class I-Related Receptor that is More Than an IgG Transporter," *Immunology Today*, 18(12):592-598.
Gillies et al., (1989), "Expression of Human Anti-Tetanus Toxoid Antibody in Transfected Murine Myeloma Cells," *Bio/Technology*, 7:799-804.
Gillies et al., (1989), "High-Level Expression of Chimeric Antibodies Using Adapted cDNA Variable Region Cassettes," *J. Immunol. Methods*, 125:191-202.
Gillies et al., (1990), "Antigen Binding and Biological Activities of Engineered Mutant Chimeric Antibodies with Human Tumor Specificities," *Hum. Antibod. Hybridomas*, 1(1):47-54.
Gillies et al., (1991), "Expression of Genetically Engineered Immunoconjugates of Lymphotoxin and a Chimeric Anti-Ganglioside GD2 Antibody," *Hybridoma*., 10(3):347-56.
Gillies et al., (1991), "Targeting Human Cytotoxc T Lymphocytes to Kill Heterologous Epidermal Growth Factor Receptor-Bearing Tumor Cells: Tumor-Infiltrating Lymphocyte/Hormone Receptor/Recombinant Antibody," *J. Immunology*, 146(3):1067-1071.
Gillies et al., (1992), "Antibody-Targeted Interleukin 2 Stimulates T-Cell Killing of Autologous Tumor Cells," *Proc. Natl. Acad. Sci. USA*, 89:1428-1432.
Gillies et al., (1993), "Biological Activity and In Vivo Clearance of Antitumor Antibody/Cytokine Fusion Proteins," *Bioconjugate Chem*., 4(3):230-235.
Gillies et al., (1998), "Antibody-IL-12 Fusion Proteins are Effective in SCID Mouse Models of Prostate and Colon Carcinoma Metastases," *J. Immunology*, 160:6195-6203.
Gillies et al., (1999), "Improving the Efficacy of Antibody-Interleukin 2 Fusion Proteins by Reducing Their Interaction with Fc Receptors," *Cancer Research*, 59:2159-2166.
Gillies et al., (2002), "Bi-Functional Cytokine Fusion Proteins for Gene Therapy and Antibody-Targeted Treatment of Cancer," *Cancer Immunol. Immunother*., 51(8):449-60.
Gillies et al., (2002), "Improved Circulating Half-Life and Efficacy of an Antibody-Interleukin 2 Immunocytokine Based on Reduced Intracellular Proteolysis," *Clin. Cancer Research*, 8(1):210-216.
Goeddel et al., (1986), "Tumor Necrosis Factors: Gene Structure and Biological Activities," *Cold Spring Harb. Symp. Quant. Biol*., 51:597-609.
Gren et al., (1983), "A New Type of Leukocytic Interferon," English Translation of *Dokl. Akad. Nauk. SSSR*., 269(4):986-990.
Grimaldi et al., (1989), "The t(5;14) Chromosomal Translocation in a Case of Acute Lymphocytic Leukemia Joins the Interleukin-3 Gene to the Immunoglobulin Heavy Chain Gene," *Blood*, 73(8):2081-2085.
Gurewich et al., (1988), "Characterization of the Intrinsic Fibrinolytic Properties of Pro-Urokinase Through a Study of Plasmin-Resistant Mutant Forms Produced by Site-Specific Mutagenesis of Lysine," *J. Clin. Invest*., 82:1956-1962.
Guyre et al., (1997), "Increased Potency of Fc-Receptor-Targeted Antigens," *Cancer Immunol. Immunother*., 45:146-148.
Halin et al., (2002), "Enhancement of the Antitumor Activity of Interleukin-12 by Targeted Delivery to Neovasculature," *Nature Biotechnology*, 20:264-269.
Hank et al., (1996), "Activation of Human Effector Cells by a Tumor Reactive Receombinant Anti-Ganglioside GD2 Interleukin-2 Fusion Protein (ch14.18-IL2)," *Clin Cancer Research*, 2(12):1951-1959.
Hank et al., (2003), "Determination of Peak Serum Levels and Immune Response to the Humanized Anti-Ganglioside Antibody-Interleukin-2 Immunocytokine," in *Methods in Molecular Medicine, 85: Novel Anticancer Drug Protocols*, Buolamwini et al., (eds), pp. 123-131, Humana Press Inc., Totowana, NJ.
Harris et al., (1993), "Therapeutic Antibodies—the Coming of Age," *Trends in Biotechnology*, 11:42-44.
Harris, (1995), "Processing of C-Terminal Lysine and Arginine Residues of Proteins Isolated from Mammalian Cell Culture," *J. Chromatography A*, 705:129-134.
Harvill et al., (1995), "An IgG3-IL2 Fusion Protein Activates Complement, Binds FcγRI, Generates LAK Activity and Shows Enhanced Binding to the High Affinity IL-2R," *Immunotechnology*, 1:95-105.
Harvill et al., (1996), "In Vivo Properties of an IgG3-IL-2 Fusion Protein: A General Strategy for Immune Potentiation," *J. Immunology*, 157(7):3165-3170.
He et al., (1998), "Humanization and Pharmacokinetics of a Monoclonal Antibody with Specificity for Both E- and P-Selectin," *J. Immunology*, 160:1029-1035.
Henkart, (1985), "Mechanism of Lymphocyte-Mediated Cytotoxicity," *Ann. Rev. Immunol*., 3:31-58.
Herrmann et al., (1989), "Hematopoietic Responses With Advanced Malignancy Treated With Recombinant Human Granulocyte-Macrophage Colony-Stimulating Factor," *Journal of Clinical Oncology*, 7(2):159-167.
Hezareh et al., (2001), "Effector Function Activities of a Panel of Mutants of a Broadly Neutralizing Antibody against Human Immunodeficiency Virus Type 1," *J. Virology*, 75(24):12161-12168.
Holden et al., (2001), "Augmentation of Antitumor Activity of an Antibody-Interleukin 2 Immunocytokine with Chemotherapeutic Agents," *Clinical Cancer Research*, 7:2862-2869.
Holden et al., (2001), "Augmentation of Anti-Tumor Activity of KS-IL2 Immunocytokine with Chemotherapeutic Agents," *Proceedings of the American Association for Cancer Research*, 42:683, Abstract No. 3675 (XP-002195344).
Hoogenboom et al., (1991), "Construction and Expression of Antibody-Tumor Necrosis Factor Fusion Proteins," *Molecular Immunology*, 28(9):1027-1037.
Hoogenboom et al., (1991), "Targeting of Tumor Necrosis Factor to Tumor Cells Secretion by Myeloma Cells of a Genetically Engineered Antibody-Tumor Necrosis Factor Hybrid Molecule," *Biochim. Biophys. Acta*, 1096(4):345-354 (Abstract).
Hornick et al., (1999), "Pretreatment with a Monoclonal Antibody/Interleukin-2 Fusion Protein Directed Against DNA Enhances the Delivery of Therapeutic Molecules to Solid Tumors," *Clin. Cancer Research*, 5:51-60.
Huck et al., (1986), "Sequence of a Human Immunoglobulin Gamma 3 Heavy Chain Constant Region Gene: Comparison With the Other Human Cγ genes," *Nucleic Acids Research*, 14(4):1779-1789.
Hulett et al., (1994), "Molecular Basis of Fc Receptor Function," *Adv. Immunol*., 57:1127.
Hurn et al., (1980), "Production of Reagent Antibodies," *Methods in Enzymology*, 70: 104-142.
Idusogie et al., (2000), "Mapping of the C1q Binding Site on Rituxan, a Chimeric Antibody with a Human IgG1 Fc," *J. Immunology*, 164(8):4178-4184.
Imboden et al., (2001), "The Level of MHC Class I Expression on Murine Adenocarcinoma Can Change the Antitumor Effector Mechanism of Immunocytokine Therapy," *Cancer Research*, 61(4):1500-7.
Isaacs et al., (1998), "Therapy with Monoclonal Antibodies. II. The Contribution of Fcγ Receptor Binding and the Influence of CH1 and CH3 Domains on In Vivo Effector Funcion," *J. Immunol*., 161:3862-3869.
Isenman et al., (1975), "The Structure and Function of Immunoglobulin Domains: II. The Importance of Interchain Disulfide Bonds and the Possible Role of Molecular Flexibility in the Interaction between Immunoglobulin G and Complement," *J. Immunology*, 114(6):1726-1729.
Jefferis et al., (1990), "Molcular Definition of Interaction Sites on Human IgG for Fc Receptors huFcγR," *Mol. Immunol*., 27(12):1237-1240.
Jones et al., (2004), "The Development of a Modified Human IFN-α2b Linked to the Fc Portion of Human IgG1 as a Novel Potential Therapeutic for the Treatment of Hepatitis C Virus Infection," *J. Interferon and Cytokine Res*., 24:560-572.
Jung et al., (1986), "Activation of Human Peripheral Blood Mononuclear Cells by Anti-T3: Killing of Tumor Target Cells Coated with Anti-Target-Anti-T3 Conjugates," *Proc. Natl. Acad. Sci. USA*, 83:4479-4483.
Junghans et al., (1996), "The Protection Receptor of IgG Catabolism is the B2-Microglobulin-Containing Neonatal Intestinal Transport Receptor," *Proc. Natl. Acad. Sci. USA*, 93(11):5512-5516.
Kappel et al., (1992), "Regulating Gene Expression in Transgenic Animals," *Current Opinion in Biotechnology*, 3:548-553.

Karpovsky et al., (1984), "Production of Target-Specific Effector Cells using Hetero-Cross Linked Aggregate Containing Anti-Target Cell and AntiFcγ Receptor Antibodies," *Journal of Experimental Medicine*, 1609(6):1686-1701.
Kendra et al., (1999), "Pharmacokinetics and Stability of the ch14. 18-Interleukin-2 Fusion Protein in Mice," *Cancer Immunol. Immunother.*, 48:219-229.
Kim et al., (1999), "Cytokine Molecular Adjuvants Modulate Immune Responses Induced by DNA Vaccine Constructs for HIV-1 and SIV," *Journal of Interferon and Cytokine Research*, 19:77-84.
King et al., (2004), "Phase I Clinical Trial of the Immunocytokine EMD 273063 in Melanoma Patients," *J. Clin. Oncol.*, 22(22):4463-73.
Ko et al., (2004), "Safety, Pharmacokinetics, and Biological Pharmacodynamics of the Immunocytokine EMD 273066 (huKS-IL2)," *J. Immunotherapy*, 27:232-239.
Kranz et al., (1984), "Attachment of an Anti-Receptor Antibody to Non-Target Cells Renders Them Susceptible to Lysis by a Clone of Cytotoxic T Lymphocytes," *Proc. Natl. Acad. Sci. USA*, 81:7922-7926.
Kushner et al., (2001), "Phase II Trial of the Anti-GD2 Monoclonal Antibody 3F8 and Granulocyte-Macrophage Colony-Stimulating Factor for Neuroblastoma," *J. Clinical Oncology*, 19(22):4189-94.
Lazar et al., (1988), "Transforming Growth Factor α: Mutation of Aspartic Acid 47 and Leucine 48 Results in Different Biological Activities," Molecular *and Cellular Biology*, 8(3):1247-1252.
LeBerthon et al., (1991), "Enhanced Tumor Uptake of Macromolecules Induced by a Novel Vasoactive Interleukin 2 Immunoconjugate," *Cancer Research*, 51:2694-2698.
Linsley et al., (1991), " CTLA-4 is a Second Receptor for B Cell Activation Antigen B7," *J. Exp. Med.*, 174(3):561-569.
Liu et al., (1985), "Heteroantibody Duplexes Target Cells for Lysis by Cytotoxic T Lymphocytes," *Proc. Natl. Acad. Sci. USA*, 82:8648-8652.
Liu et al., (1988), "Hormone Conjugated with Antibody to CD3 Mediates Cytotoxic T Cell Lysis of Human Melanoma Cells," *Science*, 239:395-398.
Lo et al., (1992), "Expression and Secretion of an Assembled Tetrameric CH2- Deleted Antibody in *E. Coli.," Hum. Antibod. Hybridomas*, 3:123-128.
Lo et al., (1998), "High Level Expression and Secretion of Fc-X Fusion Proteins in Mammalian Cells," *Protein Engineering*, 11(6):495-500.
Lo et al. (2005), "Engineering a Pharmacologically Superior Form of Leptin for the Treatment of Obesity," *Protein Engineering, Design & Selection*, 18(1):1-10.
Lode et al., (1997), "Targeted Interleukin-2 Therapy for Spontaneous Neuroblastoma Metastases to Bone Marrow," *J. Natl. Cancer Inst.*, 89(21):1586-94.
Lode et al., (1998), "Immunocytokines: A Promising Approach to Cancer Immunotherapy," *Pharmacol. Ther.*, 80(3):277-292.
Lode et al., (1998), "Natural Kill Cell-Mediated Eradication of Neuroblastoma Metastases to Bone Marrow by Targeted Interleukin-2 Therapy," *Blood*, 91(5):1706-1715.
Lode et al., (1999), "Synergy Between an Antiangiogenic Integrin $\alpha_v$ Antagonist and an Antibody-Cytokine Fusion Protein Eradicates Spontaneous Tumor Metastases," *Proc. Natl. Acad. Sci. USA*, 96:1591-1596.
Lode et al., (1999), "Tumor-Targeted IL-2 Amplifies T Cell-Mediated Immune Response Induced by Gene Therapy with Single-Chain IL-12," *Proc. Natl. Acad. Sci. USA*, 96:8591-8596.
Lode et al., (2000), "Amplification of T Cell Mediated Immune Responses by Anitbody-Cytokine Fusion Proteins," *Immunological Investigations*, 29(2):117-120.
Lode et al., (2000), "Melanoma Immunotherapy by Targeted IL-2 Depends on CD4(+) T-Cell Help Mediated by CD40/CD40L Interaction," *J. Clin. Invest.*, 105(11):1623-30.
Lode et al., (2000), "What To Do With Targeted IL-2," *Drugs of Today*, 36(5):321-336.
MacLean et al., (1996), "Enhancing the Effect of Theratope STn-KLH Cancer Vaccine in Patients with Metastatic Breast Cancer by Pretreatment with Low-Dose Intravenous Cyclophosphamide," *J. Immunother.*, 19(4):309-316.
Mark et al., (1992), "Expression and Characterization of Hepatocyte Growth Factor Receptor-IgG Fusion Proteins," *Journal of Biological Chemistry*, 267(36):26166-26171.
Martin et al., (2001), "Crystal Structure at 2.8 Å of an FcRn/Heterodimeric Fc Complex: Mechanism of pH-Dependent Binding," *Mol. Cell.*, 7(4):867-77.
McMahan et al., (1991), A Novel IL-1 Receptor, Cloned From B-Cells by Mammalian Expression is Expressed in Many Cell Types,38 *EMBO J.*, 10:2821-32.
Medesan et al., (1997), "Delineation of the Amino Acid Residues Involved in Transcytosis and Catabolism of Mouse IgG1," *J. Immunology*, 158(5):2211-2217.
Metelitsa et al., (2002), "Antidisialoganglioside/Granulocyte Macrophage-Colony-Stimulating Factor Fusion Protein Facilitates Neutrophil Antibody-Dependent Cellular Cytotoxicity and Depends on FcγRII (CD32) and Mac-1 (CD11b/CD18) for Enhanced Effector Cell Adhesion and Azurophil Granule Exocytosis," *Blood*, 99(11):4166-73.
Miyake et al., (1988), "Synthesis of Recombinant Human Single-Chain Urokinase-Type Plasminogen Activator Variants Resistant to Plasmin and Thrombin," *J. Biochem.*, 104:643-647.
Morrison et al., (1984), "Chimeric Human Antibody Molecules: Mouse Antigen-Binding Domains with Human Constant Region Domains," *Proc. Natl. Acad. Sci. USA*, 81:6851-5.
Mueller et al., (1990), "Enhancement of Antibody-Dependent Cytotoxicity With A Chimeric Anti-GD2 Antibody," *J. Immunology*, 144(4):1382-1386.
Mueller et al., (1990), "Serum Half-Life and Tumor Localization of a Chimeric Antibody Deleted of the CH2 Domain and Directed Against the Disialoganglioside GD2," *Proc. Natl. Acad. Sci. USA.*, 87:5702-5705.
Mueller et al., (1997), "Humanized Porcine VCAM-Specific Monoclonal Antibodies with Chimeric IgG2/G4 Constant Regions Block Human Leukocyte Binding to Porcine Endothelial Cells," *Molecular Immunology*, 34(6):441-452.
Murphy et al., (1986), "Genetic Construction, Expression, and Melanoma-Selective Cytotoxicity of a Diphtheria Toxin-Related α-Melanocyte-Stimulating Hormone Fusion Protein," *Proc. Natl. Acad. Sci. USA*, 83:8258-8262.
Murphy, (1988), "Diphtheria-Related Peptide Hormone Gene Fusions: A Molecular Gene Approach to Chimeric Toxin Development," in *Immunotoxins*, pp. 123-140, Frankel (ed.), Kluwer Acad. Pub.
Naramura et al., (1993), "Therapeutic Potential of Chimeric and Murine Anti-(Epidermal Growth Factor Receptor) Antibodies in a Metastasis Model for Human Melanoma," *Cancer Immuno. Immunother.*, 37:343-349.
Naramura et al., (1994), "Mechanisms of Cellular Cytotoxicity Mediated by a Recombinant Antibody-IL2 Fusion Protein Against Human Melanoma Cells," *Immunology Letters*, 39:91-99.
Nastala et al., (1994), "Recombinant IL-12 Adminstration Induces Tumor Regression in Association with IFN-γ Production," *J. Immunol.*, 153:1697-706.
Neal et al., (2003), "NXS2 Murine Neuroblastomas Express Increased Levels of MHC Class I Antigens upon Recurrence Following NK-Dependent Immunotherapy," *Cancer Immunol. Immunother.*, 53:41-52.
Neal et al., (2004), "Enhanced Activity of Hu14.18-IL2 Immunocytokine against Murine NXS2 Neuroblastoma when Combined with Interleukin-2 Therapy," *Clin. Cancer. Res.*, 10:4839-4847.
Nedwin et al., (1985), "Human Lymphotoxin and Tumor Necrosis Factor Genes: Structure, Homology and Chromosomal Localization," *Nucleic Acids Research*, 13(17):6361-6373.
Nelles et al., (1987), "Characterization of Recombinant Human Single Chain Urokinase-Type Plaminogen Activtor Mutants Produced by Site-Specific Mutagenesis of Lysine 158," *J. Biol. Chem.*, 262(12):5682-5689.
Neuberger et al., (1984), "Recombinant Antibodies Possessing Novel Effector Functions," *Nature*, 312:604-608.
Ngo et al., (1994), "Computational Complexity, Protein Structure Prediction, and the Levinthal Paradox," in *The Protein Folding Problem and Tertiary Structure Prediction*, Merz et al. (eds.), pp. 433-440 and 492-495, Birkhauser, Boston, MA.

Niethammer et al., (2001) "Targeted Interleukin 2 Therapy Enhances Protective Immunity Induced by an Autologous Oral DNA Vaccine against Murine Melanoma," *Cancer Research*, 61(16):6178-84.
Pancook et al., (1996), "Eradication of Established Hepatic Human Neuroblastoma Metastases in Mice with Severe Combined Immunodeficiency by Antibody-Targeted Interleukin-2," *Cancer Immunol. Immunother*., 42(2):88-92.
Pastan et al., (1989), "*Pseudomonas* Exotoxin: Chimeric Toxins," *Journal of Biological Chemistry*, 264(26):15157-15160.
Paul et al., (1988), "Lymphotoxin," *Ann. Rev. Immunol*., 6:407-438.
Pedley et al. (1999), "Enhancement of Antibody-Directed Enzyme Prodrug Therapy in Colorectal Xenografts by an Antivascular Agent," *Cancer Res*., 59:3998-4003.
Perez et al., (1986), "Specific Targeting of Human Peripheral Blood T Cells by Heteroaggregates Containing Anti-T3 Crosslinked to Anti-Target Cell Antibodies," *J. Exp. Med*., 163:166-178.
Poon et al., (1995), "Structure and Function of Several Anti-Dansyl Chimeric Antibodies Formed by Domain Interchanges Between Human IgM and Mouse IgG2b," *J. Biol. Chem*., 270:8571-7.
Reisfeld et al., (1996), "Antibody-Interleukin 2 Fusion Proteins: A New Approach to Cancer Therapy," *J. Clin. Lab. Anal*., 10:160-166.
Reisfeld et al., (1996), "Involvement of B Lymphocytes in the Growth Inhibition of Human Pulmonary Melanoma Metastases in Athymic *nu/nu* Mice by an Antibody-Lymphotoxin Fusion Protein," *Cancer Research*, 56(8):1707-1712.
Reisfeld et al., (1996), "Recombinant Antibody Fusion Proteins for Cancer Immunotherapy," *Current Topics in Microbiology and Immunology*, 213:27-53.
Reisfeld et al., (1997), "Immunocytokines: A New Approach to Immunotherapy of Melanoma," *Melanoma Research*, 7(Supp2):S99-S106.
Robinson et al., (1998), "Optimizing the Stability of Single-Chain Proteins by Linker Length and Composition Mutagenesis," *Proc. Natl. Acad. Sci. USA*, 95:5929-34.
Rosenberg, (1988), "Immunotherapy of Cancer Using Interleukin 2: Current Status and Future Prospects," *Immunology Today*, 9(2):58-62.
Ruehlmann et al., (2001), "MIG (CXCL9) Chemokine Gene Therapy Combines with Antibody-Cytokine Fusion Protein to Suppress Growth and Dissemination of Murine Colon Carcinoma," *Cancer Research*, 61(23):8498-503.
Sabzevari et al., (1994), "A Recombinant Antibody-Interleukin 2 Fusion Protein Suppresses Growth of Hepatic Human Severe Combined Immunodeficiency Mice," *Proc. Natl. Acad. Sci. USA*, 91(20):9626-30.
Sakano et al., (1980), "Two Types of Somatic Recombination are Necessary for the Generation of Complete Immunoglobin Heavy-Chain Genes," *Nature*, 286:676-683.
Schlom (1991), "Monoclonal Antibodies: They're More and Less Than You Think," in *Molecular Foundations of Oncology*, pp. 95-133.
Schnee et al., (1987), "Construction and Expression of a Recombinant Antibody-Targeted Plasminogen Activator," *Proc. Natl. Acad. Sci. USA*, 84:6904-6908.
Senior et al., (2000), "Cleavage of a Recombinant Human Immunoglobulin A2 (igA2)-IgA1 Hybrid Antibody by Certain Bacterial IgA1 Proteases," *Infect. Immun*., 68(2):463-9.
Senter et al., (1988), "Anti-Tumor Effects of Antibody-Alkaline Phosphatase Conjugates in Combination with Etoposide Phosphate," *Proc. Natl. Acad. Sci. USA*, 85(13):4842-4846.
Sharma et al., (1999), "T cell-Derived IL-10 Promotes Lung Cancer Growth by Suppressing Both T cell and APC Function," *Journal of Immunology*, 163:5020-5028.
Sharp et al., (1988), "Codon Usage Patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity," *Nucleic Acids Res*., 16(17):8207-8211.
Shen et al., (1986), "Heteroantibody-Mediated Cytotoxicity: Antibody to the High Affinty Fc Receptor for IgG Mediates Cytotoxicity by Human Monocytes that is Enhanced by Human Monocytes that is Enhanced by Interferon-γ and is Not Blocked by Human IgG," *J. Immunology*, 137(11):3378-3382.
Shin et al., (1990), "Expression and Characterization of an Antibody Binding Specificity Joined to Insulin-Like Growth Factor 1: Potential Applications for Cellular Targeting," *Proc. Natl. Acad. Sci. USA*, 87:5322-5326.
Shinkawa et al., (2003), "The Absence of Fucose But Not the Presence of Galactose or Bisecting N-Acetylglucosamine of HUman IgG1 Complex-Type Oligosaccharides Shows the Critical Role of Enhancing Antibody-Dependent Cellular Cytotoxicity," *J. Biol. Chem*., 278:3466-3473.
Spiekermann et al., (2002), "Receptor-Mediated Immunoglobulin G Transport Across Mucosal Barriers in Adult Life: Functional Expression of FcRn in the Mammalian Lung," *J. Exp. Med*., 196:303-310.
Stern et al., (1990), "Purification to Homogeneity and Partial Characterization of Cytotoxic Lymphocyte Maturation Factor from Human B-lymphoblastoid Cells," *Proc. Natl. Acad. Sci. USA*, 87:6808-6812.
Stevenson et al., (1997), "Conjugation of Human Fcγ in Closed-Hinge or Open-Hinge Configuration to Fab'γ and Analogous Ligands," *J. Immunology*, 158:2242-2250.
Storek et al., (2003), "Interleukin-7 Improves CD4 T-Cell Reconstitution After Autologous CD34 Cell Transplantation in Monkeys," *Blood*, 101:4209-18.
Takai, (2002), "Roles of Fc Receptors in Autoimmunity," *Nat. Rev. Immunol*., 2(8):580-92.
Tao et al., (1989), "Studies of Aglycosylated Chimeric Mouse IgG: Role of Carbohydrate in the Structure and Effector Functions Mediated by the Human IgG Constant Region," *J. Immunology*, 143(8):2595-2601.
Tao et al., (1993), "Structural Features of Human Immunoglobulin G that Determine Isotype-Differences in Complement Activation," *J. Exp. Med*., 178(2):661-667.
*The Merck Manual of Diagnosis and Therapy, 17th Ed*., (1999) pp. 990-993 and 1278-1283.
Thommesen et al., (2000), "Lysine 322 in the Human IgG3 CH2 Domain is Crucial for Antibody Dependent Complement Activation," *Mol. Immunol*., 37(16):995-1004.
Till et al., (1988), "An Assay that Predicts the Ability of Monoclonal Antibodies to Form Potent Ricin A Chain-Containing Immunotoxins," *Cancer Research*, 48(5):1119-1123.
Till et al., (1988), "HIV-Infected Cells are Killed by rCD4-Ricin A Chain," *Science*, 242:1166-1168.
Tiruppathi et al., (1996), "Isolation and Characterization of a Cell Surface Albumin-Binding Protein from Vascular Endothelial Cells," *Proc. Natl. Acad. Sci. USA*, 93:250-4.
Vagliani et al., (1996), "Interleukin 12 Potentiates the Curative Effect of a Vaccine Based on Interleukin 2-Transduced Tumor Cells," *Cancer Research*, 56:467-470.
Verhoeyen et al., (1988), "Reshaping Human Antibodies: Grafting an Antilysozyme Activity," *Science*, 239:1534-36.
Voest et al., (1995), "Inhibition of Angiogenesis in Vivo by Interleukin 12," *J. Natl. Canc. Inst*., 87:581-6.
Ward et al., (1995), "The Effector Functions of Immunoglobulins: Implications for Therapy," *Therapeutic. Immunology*, 2:77-94.
Weitkamp et al., (1973), "Additional Data on the Population Distribution of Human Serum Albumin Genes; Three New Variants," *Ann. Hum. Genet*., 37:219-26.
Wells, (1990), "Additivity of Mutational Effect in Proteins," *Biochemistry*, 29(37):8509-8517.
Williams et al., (1986), "Production of Antibody-Tagged Enzymes by Myeloma Cells: Application to DNA Polymerase I Klenow Fragment," *Gene*, 43:319-324.
Woof et al., (1986), "Localisation of the Monocyte-Binding Region on Human Immunoglobulin G," *Mol. Immunol*., 23:319-30.
Wooley et al., (1993), "Influence of a Recombinant Human Soluble Tumor Necrosis Factor Receptor Fc Fusion Protein on Type II Collagen-Induced Arthritis in Mice," *J. Immunology*, 151:6602-6607.
Wysocka et al., (1995), "Interleukin-12 is Required for Interferon-γ Production and Lethality in Lipopolysaccharide-Induced Shock in Mice," *Eur. J. Immunol*., 25:672-6.

Xiang et al., (1997), "Elimination of Established Murine Colon Carcinoma Metastases by Antibody-Interleukin 2 Fusion Protein Therapy," *Cancer Research*, 57:4948-4955.
Xu et al., (1994), "Residue at Position 331 in the IgG1 and IgG4 CH2 Domains Contributes to Their Differential Ability to Bind and Activate Complement," *J. Biol. Chem.*, 269(5):3469-3474.
Yeh et al., (1992), "Design of Yeast-Secreted Albumin Derivatives for Human Therapy: Biological and Antiviral Properties of a Serum Albumin-CD4 Genetic Conjugate," *Proc. Natl. Acad. Sci. USA*, 89:1904-8.
Yokota et al., (1986), "Isolation and Characterization of a Human Interleukin cDNA Clone, Homologous to Mouse B-Cell Stimulatory Factor 1, that Expresses B-Cell- and T-Cell-Stimulating Activities," *Proc. Natl. Acad. Sci. USA*, 83:5894-5898.
Zheng et al., (1995), "Administration of Noncytolytic IL-10/Fc In Murine Models of Lipopolysaccharide-Induced Septic Shock and Allogeneic Islet Transplantation," *Journal of Immunol.*, 154:5590-5600.
Zhu et al., (2001), "MHC Class I-Related Neonatal Fc Receptor for IgG is Functionally Expressed in Monocytes, Intestinal Macrophages and Dendritic Cells," *J. Immunol.*, 166:3266-3276.
Zuckier et al., (1998), "Chimeric Human-Mouse IgG Antibodies with Shuffled Constant Region Exons Demonstrate that Multiple Domains Contribute to In Vivo Half-Life," *Cancer Res.*, 58(17):3905-8.
Cosenza et al., "Comparative model building of interleukin-7 using interleukin-4 as a template: A structural hypothesis that displays atypical surface chemistry in helix D important for receptor activation," *Protein Science*, 9:916-926, (2000).
Cosenza et al., "Disulfide Bond Assignment in Human Interleukin-7 by Matrix-assisted Laser Desorption/Ionization Mass Spectroscopy and Site-directed Cysteine to Serine Mutational Analysis," *The Journal of Biological Chemistry*, vol. 272, No. 52, pp. 32995-33000 (1997).
vanderSpek JC et al., "Structure function analysis of interleukin 7: requirement for an aromatic ring at position 143 of helix D," *Cytokine*, 17(5): 227-33 (2002) (abstract only).
Weber et al., (2001), "Phase I Trial of huKS-IL2 Immunocytokine in Patients with Prostate Carcinoma: Clinical, PK, and Biological PD Results (Abstract)," *American Society of Clinical Oncology Program/Proceedings*, 20(Part I):259a.

* cited by examiner

Figure 1: Human IL-7 Amino Acid Sequence

MFHVSFRYIFGLPPLILVLLPVASSDCDIEGKDGKQYESVLMVSIDQLLDSMKEIGSNCLNNEFN
FFKRHICDANKEGMFLFRAARKLRQFLKMNSTGDFDLHLLKVSEGTTILLNCTGQ*VKGRKPAALG*
*EAQPTKSL*EENKSLKEQKKLNDLCFLKRLLQEIKTCWNKILMGTKEH (SEQ ID NO:1)

Figure 2: Cow IL-7 Amino Acid Sequence

MFHVSFRYIFGIPPLILVLLPVASSDCDISGRDGGAYQNVLMVNIDDLDNMINFDSNCLNNEPNF
FKKHSCDDNKEASFLNRASRKLRQFLKMNISDDFKLHLSTVSQGTLTLLNCTSKGKGRKPPSLSE
AQPTKNLEENKSSREQKKQNDLCFLKILLQKIKTCWNKILRGIKEH (SEQ ID NO:2)

Figure 3: Sheep IL-7 Amino Acid Sequence

MFHVSFRYIFGIPPLILVLLPVASSDCDFSGKDGGAYQNVLMVSIDDLDNMINFDSNCLNNEPNF
FKKHSCDDNKEASFLNRAARKLKQFLKMNISDDFKLHLSTVSQGTLTLLNCTSKGKGRKPPSLGE
AQPTKNLEENKSLKEQRKQNDLCFLKILLQKIKTCWNKILRGITEH (SEQ ID NO:3)

Figure 4 Alignment of IL-7 sequences of various mammals

```
  1 DCDIEGKDGKQYESVLMVSIDQLLDSMKEIGSNCLNNEFNFFKRHICDAN IL-7 Human
  1 --------------------------MKEIGSNCLNNEFNFFKRHICDAN IL-7 Chimp
  1 DCDIEGKDGKQYESVLMVSIDQLLDSMKEIGSNCLNNEFNFFKRHLCDDN IL-7 Baboon
  1 DCDIEGKDGKQYESVLMVSIDQLLDSMKEIGSNCLNNEFNFFKRHLCDDN IL-7 Macaque
  1 DCDISGKDGGAYQNVLMVNIDDL-DNMINFDSNCLNNEPNFFKKHSCDDN IL-7 Bovine
  1 DCDIEGKDGGVYQNVLMVSIDDL-DRMIDFDSNCLNNEPNFLKKHSCDDN IL-7 Pig
  1 DCDFSGKDGGAYQNVLMVSIDDL-DNMINFDSNCLNNEPNFFKKHSCDDN IL-7 Sheep
  1 DCHIKDKDGKAFGSVLMISINQL-DKMTGTDSDCPNNEPNFFKKHLCDDT IL-7 Rat
  1 ECHIKDKEGKAYESVLMISIDEL-DKMTGTDSNCPNNEPNFFRKHVCDDT IL-7 Murine

 51 KEGMFLFRAARKLRQFLKMNSTGDFDLHLLKVSEGTTILLNCTGQVKGRK IL-7 Human
 25 KEGMFLFRAARKLRQFLKMNSTGDFDLHLLKVSEGTTILLNCTGQVKGRK IL-7 Chimp
 51 KEGMFLFRAARKLRQFLKMNSTGDFDLHLLKVSEGTTILLNCTGKVKGRK IL-7 Baboon
 51 KEGMFLFRAARKLRQFLKMNSTGDFDLHLLKVSEGTTILLNCTGKVKGRK IL-7 Macaque
 50 KEASFLNRASRKLRQFLKMNISDDFKLHLSTVSQGTLTLLNCTSKGKGRK IL-7 Bovine
 50 KEASFLYRAARKLKQFIKMNISEEFNHHLSTVSQGTLTLFNCTSKVKGRK IL-7 Pig
 50 KEASFLNRAARKLKQFLKMNISDDFKLHLSTVSQGTLTLLNCTSKGKGRK IL-7 Sheep
 50 KEAAFLNRAARKLRQFLKMNISEEFNDHLLRVSDGTQTLVNCTSK----- IL-7 Rat
 50 KEAAFLNRAARKLKQFLKMNISEEFNVHLLTVSQGTQTLVNCTSK----- IL-7 Murine

101 PAALGEAQPTKSLEENKSLKEQKKLNDLCFLKRLLQEIKTCWNKILMGTK IL-7 Human
 75 PAALGEAQPTKSLEENKSLKEQKKLNDLCFLKRLLQEIKTCWNKILMGTK IL-7 Chimp
101 PAALGEPQPTKSLEENKSLKEQKKLNDSCFLKRLLQKIKTCWNKILMGTK IL-7 Baboon
101 PAALGEPQPTKSLEENKSLKEQKKLNDSCFLKRLLQKIKTCWNKILMGTK IL-7 Macaque
100 PPSLSEAQPTKNLEENKSSKEQKKQNDLCFLKILLQKIKTCWNKILRGIK IL-7 Bovine
100 PPSLGEAQLTKNLEENKSLKEQKRQGDLCFLKILLQKIKTCWNKILRGAK IL-7 Pig
100 PPSLGEAQPTKNLEENKSLKEQRKQNDLCFLKILLQKIKTCWNKILRGIT IL-7 Sheep
 95 --------------EEKTIKEQKK-NDPCFLKRLLREIKTCWNKILKGSI IL-7 Rat
 95 --------------EEKNVKEQKK-NDACFLKRLLREIKTCWNKILKGSI IL-7 Murine

151 EH                                            IL-7 Human   (SEQ ID NO:37)
125 EH                                            IL-7 Chimp   (SEQ ID NO:38)
151 EH                                            IL-7 Baboon  (SEQ ID NO:39)
151 EH                                            IL-7 Macaque (SEQ ID NO:40)
150 EH                                            IL-7 Bovine  (SEQ ID NO:41)
150 EY                                            IL-7 Pig     (SEQ ID NO:42)
150 EH                                            IL-7 Sheep   (SEQ ID NO:43)
129                                               IL-7 Rat     (SEQ ID NO:44)
129                                               IL-7 Murine  (SEQ ID NO:45)
```

Figure 6

Average -fold change in plasma concentration

| | Day 2 / Day 0 | | Day 4 / Day 2 | |
|---|---|---|---|---|
| | | sd | | sd |
| 0.5 mg/kg SC qdx5 | 5.5 | 0.0 | 2.2 | 0.5 |
| 5 mg/kg SC qdx5 | 4.5 | 0.3 | 2.1 | 0.3 |
| 25 mg/kg SC qdx5 | 2.5 | 0.3 | 1.6 | 0.3 |
| | | | | |
| average all doses: | 4.2 | 1.2 | 2.0 | 0.3 |

Figure 7

Average Organ Weights (g) on Day 7

| | Lung | +/- sd | Spleen | +/- sd | Kidney | +/- sd | Liver | +/- sd | Thymus | +/- sd |
|---|---|---|---|---|---|---|---|---|---|---|
| Vehicle | 0.175 | 0.075 | 0.137 | 0.024 | 0.192 | 0.033 | 1.323 | 0.110 | 0.093 | 0.003 |
| hu Fc g2h (N-->Q) -L2-hu IL7 (PNDS) 10ug, day0-4 | 0.201 | 0.004 | 0.462 | 0.059 | 0.190 | 0.009 | 1.354 | 0.186 | 0.141 | 0.024 |
| hu Fc g2h (N-->Q) -L2-hu IL7 (PNDS) 100ug, day0-4 | 0.352 | 0.045 | 0.661 | 0.054 | 0.168 | 0.044 | 1.098 | 0.350 | 0.102 | 0.053 |
| hu Fc g2h (N-->Q) -L2-hu IL7 (PNDS) 500ug, day0-4 | 0.387 | 0.014 | 0.681 | 0.053 | 0.151 | 0.014 | 1.460 | 0.063 | 0.121 | 0.011 |

SEQUENCE LISTING

```
<160> NUMBER OF SEQ ID NOS: 72

<210> SEQ ID NO 1
<211> LENGTH: 177
<212> TYPE: PRT
<213> ORGANISM: Homo sapiens

<400> SEQUENCE: 1

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
```

-continued

```
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His


<210> SEQ ID NO 2
<211> LENGTH: 176
<212> TYPE: PRT
<213> ORGANISM: Bos taurus

<400> SEQUENCE: 2

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Ile Ser Gly Arg
            20                  25                  30

Asp Gly Gly Ala Tyr Gln Asn Val Leu Met Val Asn Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ser Arg Lys Leu Arg Gln Phe Leu Lys Met Asn Ile Ser
                85                  90                  95

Asp Asp Phe Lys Leu His Leu Ser Thr Val Ser Gln Gly Thr Leu Thr
            100                 105                 110

Leu Leu Asn Cys Thr Ser Lys Gly Lys Gly Arg Lys Pro Pro Ser Leu
        115                 120                 125

Ser Glu Ala Gln Pro Thr Lys Asn Leu Glu Glu Asn Lys Ser Ser Arg
    130                 135                 140

Glu Gln Lys Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Lys Glu His
                165                 170                 175


<210> SEQ ID NO 3
<211> LENGTH: 176
<212> TYPE: PRT
<213> ORGANISM: Ovis aries

<400> SEQUENCE: 3

Met Phe His Val Ser Phe Arg Tyr Ile Phe Gly Ile Pro Pro Leu Ile
1               5                   10                  15

Leu Val Leu Leu Pro Val Ala Ser Ser Asp Cys Asp Phe Ser Gly Lys
            20                  25                  30

Asp Gly Gly Ala Tyr Gln Asn Val Leu Met Val Ser Ile Asp Asp Leu
        35                  40                  45

Asp Asn Met Ile Asn Phe Asp Ser Asn Cys Leu Asn Asn Glu Pro Asn
    50                  55                  60

Phe Phe Lys Lys His Ser Cys Asp Asp Asn Lys Glu Ala Ser Phe Leu
65                  70                  75                  80

Asn Arg Ala Ala Arg Lys Leu Lys Gln Phe Leu Lys Met Asn Ile Ser
                85                  90                  95

Asp Asp Phe Lys Leu His Leu Ser Thr Val Ser Gln Gly Thr Leu Thr
            100                 105                 110
```

-continued

```
Leu Leu Asn Cys Thr Ser Lys Gly Lys Gly Arg Lys Pro Pro Ser Leu
        115                 120                 125

Gly Glu Ala Gln Pro Thr Lys Asn Leu Glu Glu Asn Lys Ser Leu Lys
    130                 135                 140

Glu Gln Arg Lys Gln Asn Asp Leu Cys Phe Leu Lys Ile Leu Leu Gln
145                 150                 155                 160

Lys Ile Lys Thr Cys Trp Asn Lys Ile Leu Arg Gly Ile Thr Glu His
                165                 170                 175


<210> SEQ ID NO 4
<211> LENGTH: 152
<212> TYPE: PRT
<213> ORGANISM: Artificial Sequence
<220> FEATURE:
<223> OTHER INFORMATION: Deimmunized Human IL-7 Amino Acid Sequence.

<400> SEQUENCE: 4

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Asp Asp Asn Ser Thr Gly Asp Phe Asp Leu His Leu Leu
65                  70                  75                  80

Lys Val Ser Glu Gly Thr Thr Thr Leu Leu Asn Cys Thr Gly Gln Gly
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 5
<211> LENGTH: 153
<212> TYPE: PRT
<213> ORGANISM: Artificial Sequence
<220> FEATURE:
<223> OTHER INFORMATION: Bacterially Produced Deimmunized Human IL-7
      Amino acid sequence.

<400> SEQUENCE: 5

Met Asp Cys Asp Ile Glu Gly Lys Asp Gly Lys Gln Tyr Glu Ser Val
1               5                   10                  15

Leu Met Val Ser Ile Asp Gln Leu Leu Asp Ser Met Lys Glu Ile Gly
            20                  25                  30

Ser Asn Cys Leu Asn Asn Glu Phe Asn Phe Phe Lys Arg His Ile Cys
        35                  40                  45

Asp Ala Asn Lys Glu Gly Met Phe Leu Phe Arg Ala Ala Arg Lys Leu
    50                  55                  60

Arg Gln Phe Leu Asp Asp Asn Ser Thr Gly Asp Phe Asp Leu His Leu
65                  70                  75                  80
```

-continued

```
Leu Lys Val Ser Glu Gly Thr Thr Thr Leu Leu Asn Cys Thr Gly Gln
                85                  90                  95

Gly Lys Gly Arg Lys Pro Ala Ala Leu Gly Glu Ala Gln Pro Thr Lys
            100                 105                 110

Ser Leu Glu Glu Asn Lys Ser Leu Lys Glu Gln Lys Lys Leu Asn Asp
        115                 120                 125

Leu Cys Phe Leu Lys Arg Leu Leu Gln Glu Ile Lys Thr Cys Trp Asn
    130                 135                 140

Lys Ile Leu Met Gly Thr Lys Glu His
145                 150


<210> SEQ ID NO 6
<211> LENGTH: 456
<212> TYPE: DNA
<213> ORGANISM: Artificial Sequence
<220> FEATURE:
<223> OTHER INFORMATION: Nucleic acid sequence encoding mature IL-7 with
      codon substitutions for F39P, F57N, and L128S.

<400> SEQUENCE: 6

gattgtgata ttgagggtaa ggatggcaaa cagtacgaga gtgttctaat ggtgagcatc     60

gaccagttat tggacagcat gaaggagatt gggagcaatt gcctgaataa cgaacccaac    120

ttctttaaga gacacatctg cgatgccaat aaggaaggga tgtttttaaa ccgtgctgcc    180

cgcaagttga ggcaattcct taaaatgaac agcactggtg actttgatct ccacctgtta    240

aaagtttcag aaggcaccac aatcctgttg aactgcactg gccaggtgaa aggaaggaaa    300

cctgctgccc tgggtgaagc tcaaccaaca aagagtttgg aggagaataa atctttaaag    360

gaacagaaaa aactgaatga cagctgtttc ctaaagagac tactgcaaga gataaaaact    420

tgctggaata aaatcttgat gggcactaaa gaacac                              456


<210> SEQ ID NO 7
<211> LENGTH: 152
<212> TYPE: PRT
<213> ORGANISM: Artificial Sequence
<220> FEATURE:
<223> OTHER INFORMATION: Amino acid sequence of mature IL-7 with codons
      for amino acid substitutions F39P, F57N, and L128S

<400> SEQUENCE: 7

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Pro Asn Phe Phe Lys Arg His Ile Cys Asp
        35                  40                  45

Ala Asn Lys Glu Gly Met Phe Leu Asn Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Ser
        115                 120                 125

Cys Phe Leu Lys Arg Leu Leu Gln Glu Ile Lys Thr Cys Trp Asn Lys
    130                 135                 140
```

-continued

```
Ile Leu Met Gly Thr Lys Glu His
145                 150


<210> SEQ ID NO 8
<211> LENGTH: 456
<212> TYPE: DNA
<213> ORGANISM: Artificial Sequence
<220> FEATURE:
<223> OTHER INFORMATION: Nucleic acid sequence encoding mature IL-7 with
      codons for amino acid substitutions F39P, F57N, L77D, and L128S.

<400> SEQUENCE: 8

gattgtgata ttgagggtaa ggatggcaaa cagtacgaga gtgttctaat ggtgagcatc      60

gaccagttat tggacagcat gaaggagatt gggagcaatt gcctgaataa cgaacccaac     120

ttctttaaga gacacatctg cgatgccaat aaggaaggga tgtttttaaa ccgtgctgcc     180

cgcaagttga ggcaattcct taaaatgaac agcactggtg actttgatga ccacctgtta     240

aaagtttcag aaggcaccac aatcctgttg aactgcactg gccaggtgaa aggaaggaaa     300

cctgctgccc tgggtgaagc tcaaccaaca aagagtttgg aggagaataa atctttaaag     360

gaacagaaaa aactgaatga cagctgtttc ctaaagagac tactgcaaga gataaaaact     420

tgctggaata aaatcttgat gggcactaaa gaacac                               456


<210> SEQ ID NO 9
<211> LENGTH: 152
<212> TYPE: PRT
<213> ORGANISM: Artificial Sequence
<220> FEATURE:
<223> OTHER INFORMATION: Amino acid sequence of mature IL-7 with codons
      for amino acid substitutions F39P, F57N, L77D, and L128S.

<400> SEQUENCE: 9

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Pro Asn Phe Phe Lys Arg His Ile Cys Asp
        35                  40                  45

Ala Asn Lys Glu Gly Met Phe Leu Asn Arg Ala Ala Arg Lys Leu Arg
    50                  55                  60

Gln Phe Leu Lys Met Asn Ser Thr Gly Asp Phe Asp Asp His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Ser
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150


<210> SEQ ID NO 10
<211> LENGTH: 462
<212> TYPE: DNA
<213> ORGANISM: Artificial Sequence
<220> FEATURE:
<223> OTHER INFORMATION: Nucleic acid sequence encoding bacterially
```

-continued produced deimmunized IL-7, codon-optimized for E. coli with codons for amino acid substitutions K68D, M69D, I88T, V96G.

<400> SEQUENCE: 10

```
atggactgcg acatcgaagg taaagacggc aaacagtacg aatccgttct gatggtttcc     60

atcgaccagc tgctggactc catgaaagaa atcggctcca actgcctgaa caacgaattc    120

aacttcttca aacggcacat atgcgacgct aacaaagaag gcatgttcct gttccgcgct    180

gctcgcaaac tgcgccagtt cctggatgat aactctaccg gtgacttcga cctgcacctg    240

ctgaaagttt ctgaaggtac tactaccctg ctgaactgca ctggccaggg taaaggccgc    300

aagccggccg ctctgggcga agctcagccg actaaatctc tagaagaaaa caaatccctg    360

aaagaacaga agaagctgaa cgacctgtgc ttcctgaaac gcctgctgca ggaaatcaaa    420

acttgctgga acaaaatcct gatgggcact aaagaacact ag                        462
```

<210> SEQ ID NO 11
<211> LENGTH: 459
<212> TYPE: DNA
<213> ORGANISM: Artificial Sequence
<220> FEATURE:
<223> OTHER INFORMATION: Nucleic acid sequence encoding a mature deimmunized IL-7 variant with codons for amino acid substitutions K68D, M69D, I88T, V96G.

<400> SEQUENCE: 11

```
gattgtgata ttgaaggtaa agatggcaaa caatatgaga gtgttctaat ggtcagcatc     60

gatcaattat tggacagcat gaaagaaatt ggtagcaatt gcctgaataa tgaatttaac    120

ttttttaaaa gacatatctg tgatgctaat aaggaaggta tgtttttatt ccgtgctgct    180

cgcaagttga ggcaatttct tgacgataat agcactggtg attttgatct ccacttatta    240

aaagtttcag aaggcacaac aaccctgttg aactgcactg gccagggcaa aggaagaaaa    300

ccagctgccc tgggtgaagc ccaaccaaca aagagtttgg aagaaaataa atctttaaag    360

gaacagaaaa aactgaatga cttgtgtttc ctaaagagac tattacaaga gataaaaact    420

tgttggaata aaattttgat gggcactaaa gaacactga                           459
```

<210> SEQ ID NO 12
<211> LENGTH: 384
<212> TYPE: PRT
<213> ORGANISM: Artificial Sequence
<220> FEATURE:
<223> OTHER INFORMATION: Amino Acid Sequence for Human Fcgamma1-IL-7.

<400> SEQUENCE: 12

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110
```

-continued

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Ala Thr Ala Thr Pro Gly Ala Asp Cys Asp Ile Glu Gly Lys Asp
225                 230                 235                 240

Gly Lys Gln Tyr Glu Ser Val Leu Met Val Ser Ile Asp Gln Leu Leu
                245                 250                 255

Asp Ser Met Lys Glu Ile Gly Ser Asn Cys Leu Asn Asn Glu Phe Asn
            260                 265                 270

Phe Phe Lys Arg His Ile Cys Asp Ala Asn Lys Glu Gly Met Phe Leu
        275                 280                 285

Phe Arg Ala Ala Arg Lys Leu Arg Gln Phe Leu Lys Met Asn Ser Thr
    290                 295                 300

Gly Asp Phe Asp Leu His Leu Leu Lys Val Ser Glu Gly Thr Thr Ile
305                 310                 315                 320

Leu Leu Asn Cys Thr Gly Gln Val Lys Gly Arg Lys Pro Ala Ala Leu
                325                 330                 335

Gly Glu Ala Gln Pro Thr Lys Ser Leu Glu Glu Asn Lys Ser Leu Lys
            340                 345                 350

Glu Gln Lys Lys Leu Asn Asp Leu Cys Phe Leu Lys Arg Leu Leu Gln
        355                 360                 365

Glu Ile Lys Thr Cys Trp Asn Lys Ile Leu Met Gly Thr Lys Glu His
    370                 375                 380

<210> SEQ ID NO 13
<211> LENGTH: 383
<212> TYPE: PRT
<213> ORGANISM: Artificial Sequence
<220> FEATURE:
<223> OTHER INFORMATION: Amino Acid Sequence for Human
      Fcgamma2(h)(FN>AQ)-IL-7.

<400> SEQUENCE: 13

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val Val His Gln Asp

-continued

```
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Ala Thr Ala Thr Pro Gly Ala Asp Cys Asp Ile Glu Gly Lys Asp Gly
225                 230                 235                 240

Lys Gln Tyr Glu Ser Val Leu Met Val Ser Ile Asp Gln Leu Leu Asp
                245                 250                 255

Ser Met Lys Glu Ile Gly Ser Asn Cys Leu Asn Asn Glu Phe Asn Phe
            260                 265                 270

Phe Lys Arg His Ile Cys Asp Ala Asn Lys Glu Gly Met Phe Leu Phe
        275                 280                 285

Arg Ala Ala Arg Lys Leu Arg Gln Phe Leu Lys Met Asn Ser Thr Gly
    290                 295                 300

Asp Phe Asp Leu His Leu Leu Lys Val Ser Glu Gly Thr Thr Ile Leu
305                 310                 315                 320

Leu Asn Cys Thr Gly Gln Val Lys Gly Arg Lys Pro Ala Ala Leu Gly
                325                 330                 335

Glu Ala Gln Pro Thr Lys Ser Leu Glu Glu Asn Lys Ser Leu Lys Glu
            340                 345                 350

Gln Lys Lys Leu Asn Asp Leu Cys Phe Leu Lys Arg Leu Leu Gln Glu
        355                 360                 365

Ile Lys Thr Cys Trp Asn Lys Ile Leu Met Gly Thr Lys Glu His
    370                 375                 380


<210> SEQ ID NO 14
<211> LENGTH: 398
<212> TYPE: PRT
<213> ORGANISM: Artificial Sequence
<220> FEATURE:
<223> OTHER INFORMATION: Amino Acid Sequence for Human
      Fcgamma1-(linker1)-IL-7

<400> SEQUENCE: 14

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

-continued

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Ala Thr Ala Thr Pro Gly Ala Gly Gly Gly Gly Ser Gly Gly Gly
225 230 235 240

Gly Ser Gly Gly Gly Ser Asp Cys Asp Ile Glu Gly Lys Asp Gly Lys
245 250 255

Gln Tyr Glu Ser Val Leu Met Val Ser Ile Asp Gln Leu Leu Asp Ser
260 265 270

Met Lys Glu Ile Gly Ser Asn Cys Leu Asn Asn Glu Phe Asn Phe Phe
275 280 285

Lys Arg His Ile Cys Asp Ala Asn Lys Glu Gly Met Phe Leu Phe Arg
290 295 300

Ala Ala Arg Lys Leu Arg Gln Phe Leu Lys Met Asn Ser Thr Gly Asp
305 310 315 320

Phe Asp Leu His Leu Leu Lys Val Ser Glu Gly Thr Thr Ile Leu Leu
325 330 335

Asn Cys Thr Gly Gln Val Lys Gly Arg Lys Pro Ala Ala Leu Gly Glu
340 345 350

Ala Gln Pro Thr Lys Ser Leu Glu Glu Asn Lys Ser Leu Lys Glu Gln
355 360 365

Lys Lys Leu Asn Asp Leu Cys Phe Leu Lys Arg Leu Leu Gln Glu Ile
370 375 380

Lys Thr Cys Trp Asn Lys Ile Leu Met Gly Thr Lys Glu His
385 390 395

<210> SEQ ID NO 15
<211> LENGTH: 15
<212> TYPE: PRT
<213> ORGANISM: Artificial Sequence
<220> FEATURE:
<223> OTHER INFORMATION: A polypeptide linker.

<400> SEQUENCE: 15

Gly Gly Gly Gly Ser Gly Gly Gly Gly Ser Gly Gly Gly Gly Ser
1 5 10 15

<210> SEQ ID NO 16
<211> LENGTH: 393

-continued

<212> TYPE: PRT
<213> ORGANISM: Artificial Sequence
<220> FEATURE:
<223> OTHER INFORMATION: Amino Acid Sequence for Human
      Fcgamma1(YN>AQ)-(linker2)-IL-7.

<400> SEQUENCE: 16

```
Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Ala Gln Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Ala Thr Ala Thr Pro Gly Ala Gly Gly Gly Gly Ser Gly Gly Gly
225                 230                 235                 240

Gly Asp Cys Asp Ile Glu Gly Lys Asp Gly Lys Gln Tyr Glu Ser Val
                245                 250                 255

Leu Met Val Ser Ile Asp Gln Leu Leu Asp Ser Met Lys Glu Ile Gly
            260                 265                 270

Ser Asn Cys Leu Asn Asn Glu Phe Asn Phe Phe Lys Arg His Ile Cys
        275                 280                 285

Asp Ala Asn Lys Glu Gly Met Phe Leu Phe Arg Ala Ala Arg Lys Leu
    290                 295                 300

Arg Gln Phe Leu Lys Met Asn Ser Thr Gly Asp Phe Asp Leu His Leu
305                 310                 315                 320

Leu Lys Val Ser Glu Gly Thr Thr Ile Leu Leu Asn Cys Thr Gly Gln
                325                 330                 335

Val Lys Gly Arg Lys Pro Ala Ala Leu Gly Glu Ala Gln Pro Thr Lys
            340                 345                 350

Ser Leu Glu Glu Asn Lys Ser Leu Lys Glu Gln Lys Lys Leu Asn Asp
        355                 360                 365

Leu Cys Phe Leu Lys Arg Leu Leu Gln Glu Ile Lys Thr Cys Trp Asn
    370                 375                 380
```

-continued

Lys Ile Leu Met Gly Thr Lys Glu His
385 390

<210> SEQ ID NO 17
<211> LENGTH: 9
<212> TYPE: PRT
<213> ORGANISM: Artificial Sequence
<220> FEATURE:
<223> OTHER INFORMATION: A polypeptide linker.

<400> SEQUENCE: 17

Gly Gly Gly Gly Ser Gly Gly Gly Gly
1 5

<210> SEQ ID NO 18
<211> LENGTH: 391
<212> TYPE: PRT
<213> ORGANISM: Artificial Sequence
<220> FEATURE:
<223> OTHER INFORMATION: Amino Acid Sequence for Human Fcgamma1(YN>AQ,d)-(linker2)-IL-7.

<400> SEQUENCE: 18

Glu Pro Lys Ser Ser Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Ala Gln Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Asp Glu Leu Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Ala Thr Ala Thr Pro Gly Gly Gly Gly Ser Gly Gly Gly Gly Asp
225 230 235 240

Cys Asp Ile Glu Gly Lys Asp Gly Lys Gln Tyr Glu Ser Val Leu Met
245 250 255

Val Ser Ile Asp Gln Leu Leu Asp Ser Met Lys Glu Ile Gly Ser Asn
260 265 270

-continued

```
Cys Leu Asn Asn Glu Phe Asn Phe Phe Lys Arg His Ile Cys Asp Ala
        275                 280                 285

Asn Lys Glu Gly Met Phe Leu Phe Arg Ala Ala Arg Lys Leu Arg Gln
    290                 295                 300

Phe Leu Lys Met Asn Ser Thr Gly Asp Phe Asp Leu His Leu Leu Lys
305                 310                 315                 320

Val Ser Glu Gly Thr Thr Ile Leu Leu Asn Cys Thr Gly Gln Val Lys
                325                 330                 335

Gly Arg Lys Pro Ala Ala Leu Gly Glu Ala Gln Pro Thr Lys Ser Leu
            340                 345                 350

Glu Glu Asn Lys Ser Leu Lys Glu Gln Lys Lys Leu Asn Asp Leu Cys
        355                 360                 365

Phe Leu Lys Arg Leu Leu Gln Glu Ile Lys Thr Cys Trp Asn Lys Ile
    370                 375                 380

Leu Met Gly Thr Lys Glu His
385                 390
```

<210> SEQ ID NO 19
<211> LENGTH: 911
<212> TYPE: DNA
<213> ORGANISM: Artificial Sequence
<220> FEATURE:
<223> OTHER INFORMATION: Nucleic Acid Sequence for Human Fcgamma1.

<400> SEQUENCE: 19

```
gagcccaaat cttctgacaa aactcacaca tgcccaccgt gcccaggtaa gccagcccag     60

gcctcgccct ccagctcaag gcgggacagg tgccctagag tagcctgcat ccagggacag    120

gccccagccg ggtgctgaca cgtccacctc catctcttcc tcagcacctg aactcctggg    180

gggaccgtca gtcttcctct tcccccccaaa acccaaggac accctcatga tctcccggac    240

ccctgaggtc acatgcgtgg tggtggacgt gagccacgaa gaccctgagg tcaagttcaa    300

ctggtacgtg gacggcgtgg aggtgcataa tgccaagaca aagccgcggg aggagcagta    360

caacagcacg taccgtgtgg tcagcgtcct caccgtcctg caccaggact ggctgaatgg    420

caaggagtac aagtgcaagg tctccaacaa agccctccca gcccccatcg agaaaaccat    480

ctccaaagcc aaaggtggga cccgtggggt gcgagggcca catggacaga ggccggctcg    540

gcccaccctc tgccctgaga gtgaccgctg taccaacctc tgtccctaca gggcagcccc    600

gagaaccaca ggtgtacacc ctgcccccat cacgggagga gatgaccaag aaccaggtca    660

gcctgacctg cctggtcaaa ggcttctatc ccagcgacat cgccgtggag tgggagagca    720

atgggcagcc ggagaacaac tacaagacca cgcctcccgt gctggactcc gacggctcct    780

tcttcctcta tagcaagctc accgtggaca agagcaggtg gcagcagggg aacgtcttct    840

catgctccgt gatgcatgag gctctgcaca accactacac gcagaagagc gccaccgcga    900

ccccgggcgc c                                                          911
```

<210> SEQ ID NO 20
<211> LENGTH: 911
<212> TYPE: DNA
<213> ORGANISM: Artificial Sequence
<220> FEATURE:
<223> OTHER INFORMATION: Nucleic Acid Sequence for Human Fcgamma1(YN>AQ).

<400> SEQUENCE: 20

```
gagcccaaat cttctgacaa aactcacaca tgcccaccgt gcccaggtaa gccagcccag     60
```

-continued

```
gcctcgccct ccagctcaag gcgggacagg tgccctagag tagcctgcat ccagggacag    120

gccccagccg ggtgctgaca cgtccacctc catctcttcc tcagcacctg aactcctggg    180

gggaccgtca gtcttcctct tcccccccaaa acccaaggac accctcatga tctcccggac    240

ccctgaggtc acatgcgtgg tggtggacgt gagccacgaa gaccctgagg tcaagttcaa    300

ctggtacgtg gacggcgtgg aggtgcataa tgccaagaca aagccgcggg aggagcaggc    360

ccagagcacg taccgtgtgg tcagcgtcct caccgtcctg caccaggact ggctgaatgg    420

caaggagtac aagtgcaagg tctccaacaa agccctccca gcccccatcg agaaaaccat    480

ctccaaagcc aaaggtggga cccgtggggt gcgagggcca catggacaga ggccggctcg    540

gcccaccctc tgccctgaga gtgaccgctg taccaacctc tgtccctaca gggcagcccc    600

gagaaccaca ggtgtacacc ctgcccccat cacgggagga gatgaccaag aaccaggtca    660

gcctgacctg cctggtcaaa ggcttctatc ccagcgacat cgccgtggag tgggagagca    720

atgggcagcc ggagaacaac tacaagacca cgcctcccgt gctggactcc gacggctcct    780

tcttcctcta tagcaagctc accgtggaca agagcaggtg gcagcagggg aacgtcttct    840

catgctccgt gatgcatgag gctctgcaca accactacac gcagaagagc gccaccgcga    900

ccccgggcgc c                                                          911


<210> SEQ ID NO 21
<211> LENGTH: 908
<212> TYPE: DNA
<213> ORGANISM: Artificial Sequence
<220> FEATURE:
<223> OTHER INFORMATION: Nucleic Acid Sequence for Human Fcgamma2(h).

<400> SEQUENCE: 21

gagcccaaat cttctgacaa aactcacaca tgcccaccgt gcccaggtaa gccagcccag     60

gcctcgccct ccagctcaag gcgggacagg tgccctagag tagcctgcat ccagggacag    120

gccccagctg ggtgctgaca cgtccacctc catctcttcc tcagcaccac ctgtggcagg    180

accgtcagtc ttcctcttcc ccccaaaacc caaggacacc ctcatgatct cccggacccc    240

tgaggtcacg tgcgtggtgg tggacgtgag ccacgaagac cccgaggtcc agttcaactg    300

gtacgtggac ggcgtggagg tgcataatgc caagacaaag ccacgggagg agcagttcaa    360

cagcacgttc cgtgtggtca gcgtcctcac cgttgtgcac caggactggc tgaacggcaa    420

ggagtacaag tgcaaggtct ccaacaaagg cctcccagcc cccatcgaga aaaccatctc    480

caaaaccaaa ggtgggaccc gcggggtatg agggccacat ggacagaggc cggctcggcc    540

caccctctgc cctgagagtg accgctgtac caacctctgt ccctacaggg cagccccgag    600

aaccacaggt gtacaccctg cccccatcac gggaggagat gaccaagaac caggtcagcc    660

tgacctgcct ggtcaaaggc ttctacccca gcgacatcgc cgtggagtgg gagagcaatg    720

ggcagccgga gaacaactac aagaccacac ctcccatgct ggactccgac ggctccttct    780

tcctctacag caagctcacc gtggacaaga gcaggtggca gcaggggaac gtcttctcat    840

gctccgtgat gcatgaggct ctgcacaacc actacacaca gaagagcgcc accgcgaccc    900

cgggcgcc                                                              908


<210> SEQ ID NO 22
<211> LENGTH: 908
<212> TYPE: DNA
<213> ORGANISM: Artificial Sequence
<220> FEATURE:
<223> OTHER INFORMATION: Nucleic Acid Sequence for Human
```

-continued

Fcgamma2(h)(FN>AQ).

<400> SEQUENCE: 22

```
gagcccaaat cttctgacaa aactcacaca tgcccaccgt gcccaggtaa gccagcccag     60
gcctcgccct ccagctcaag gcgggacagg tgccctagag tagcctgcat ccagggacag    120
gccccagctg ggtgctgaca cgtccacctc catctcttcc tcagcaccac ctgtggcagg    180
accgtcagtc ttcctcttcc ccccaaaacc caaggacacc ctcatgatct cccggacccc    240
tgaggtcacg tgcgtggtgg tggacgtgag ccacgaagac cccgaggtcc agttcaactg    300
gtacgtggac ggcgtggagg tgcataatgc caagacaaag ccacgggagg agcaggccca    360
gagcacgttc cgtgtggtca gcgtcctcac cgttgtgcac caggactggc tgaacggcaa    420
ggagtacaag tgcaaggtct ccaacaaagg cctcccagcc cccatcgaga aaaccatctc    480
caaaaccaaa ggtgggaccc gcggggtatg agggccacat ggacagaggc cggctcggcc    540
caccctctgc cctgagagtg accgctgtac caacctctgt ccctacaggg cagccccgag    600
aaccacaggt gtacaccctg cccccatcac gggaggagat gaccaagaac caggtcagcc    660
tgacctgcct ggtcaaaggc ttctacccca gcgacatcgc cgtggagtgg gagagcaatg    720
ggcagccgga gaacaactac aagaccacac ctcccatgct ggactccgac ggctccttct    780
tcctctacag caagctcacc gtggacaaga gcaggtggca gcaggggaac gtcttctcat    840
gctccgtgat gcatgaggct ctgcacaacc actacacaca gaagagcgcc accgcgaccc    900
cgggtgca                                                             908
```

<210> SEQ ID NO 23
<211> LENGTH: 149
<212> TYPE: PRT
<213> ORGANISM: Artificial Sequence
<220> FEATURE:
<223> OTHER INFORMATION: Amino acid sequence for mature human deimmunized-IL-7.1.

<400> SEQUENCE: 23

```
Asp Cys Asp Ile Glu Gly Lys Asp Gly Lys Gln Tyr Glu Ser Val Leu
1               5                   10                  15

Met Val Ser Ile Asp Gln Leu Asp Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Ala Phe Leu Lys Arg Ala Ser Glu Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Lys Gly Ser
145
```

<210> SEQ ID NO 24

-continued

```
<211> LENGTH: 450
<212> TYPE: DNA
<213> ORGANISM: Artificial Sequence
<220> FEATURE:
<223> OTHER INFORMATION: Nucleic acid sequence encoding mature human
      deimmunized IL-7.1.

<400> SEQUENCE: 24

gattgtgata ttgaaggtaa agatggcaaa caatatgaga gtgttctaat ggtcagcatc     60

gatcaattag acgacagcat gaaagaaatt ggtagcaatt gcctgaataa tgaatttaac    120

ttttttaaaa gacatatctg tgatgctaat aaggaaggtg ccttttttaaa gcgtgcttcc    180

gagaagttga ggcaatttct taaaatgaat agcactggtg attttgatct ccacttatta    240

aaagtttcag aaggcacaac aatactgttg aactgcactg gccaggttaa aggaagaaaa    300

ccagctgccc tgggtgaagc ccaaccaaca aagagtttgg aagaaaataa atctttaaag    360

gaacagaaaa aactgaatga cttgtgtttc ctaaagagac tattacaaga gataaaaact    420

tgttggaata aaattttgaa aggcagctga                                     450


<210> SEQ ID NO 25
<211> LENGTH: 149
<212> TYPE: PRT
<213> ORGANISM: Artificial Sequence
<220> FEATURE:
<223> OTHER INFORMATION: Amino acid sequence for mature human
      deimmunized IL-7.2.

<400> SEQUENCE: 25

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asn Asp His Leu Leu
65                  70                  75                  80

Lys Val Ser Glu Gly Thr Gln Thr Leu Leu Asn Cys Thr Gly Gln Gly
                85                  90                  95

Lys Gly Arg Lys Pro Ala Ala Leu Gly Glu Ala Gln Pro Thr Lys Ser
            100                 105                 110

Leu Glu Glu Asn Lys Ser Ser Lys Glu Gln Lys Lys Leu Asn Asp Val
        115                 120                 125

Cys Phe Leu Lys Arg Leu Leu Gln Glu Ile Lys Thr Cys Trp Asn Lys
    130                 135                 140

Ile Leu Lys Gly Ser
145


<210> SEQ ID NO 26
<211> LENGTH: 450
<212> TYPE: DNA
<213> ORGANISM: Artificial Sequence
<220> FEATURE:
<223> OTHER INFORMATION: Nucleic acid sequence encoding mature human
      deimmunized IL-7.2.

<400> SEQUENCE: 26

gattgtgata ttgaaggtaa agatggcaaa caatatgaga gtgttctaat ggtcagcatc     60
```

-continued

```
gatcaattat tggacagcat gaaagaaatt ggtagcaatt gcctgaataa tgaatttaac    120

tttttaaaa gacatatctg tgatgctaat aaggaaggta tgtttttatt ccgtgctgct    180

cgcaagttga ggcaatttct taaaatgaat agcactggtg attttaacga tcacttatta    240

aaagtttcag aaggcacaca gacactcttg aactgcactg gccagggcaa aggaagaaaa    300

ccagctgccc tgggtgaagc ccaaccaaca aagagtttgg aagaaaataa atcttctaag    360

gaacagaaaa aactgaatga cgtgtgtttc ctaaagagac tattacaaga gataaaaact    420

tgttggaata aaattttgaa aggcagctga                                    450


<210> SEQ ID NO 27
<211> LENGTH: 149
<212> TYPE: PRT
<213> ORGANISM: Artificial Sequence
<220> FEATURE:
<223> OTHER INFORMATION: Amino acid sequence for mature human
      deimmunized IL-7.3.

<400> SEQUENCE: 27

Asp Cys Asp Ile Glu Gly Lys Asp Gly Lys Gln Tyr Glu Ser Val Leu
1               5                   10                  15

Met Val Ser Ile Asp Gln Leu Asp Asp Ser Met Lys Glu Thr Gly Ser
            20                  25                  30

Asn Cys Leu Asn Asn Glu Pro Asn Phe Phe Lys Arg His Ile Cys Asp
        35                  40                  45

Ala Asn Lys Glu Gly Ala Phe Leu Lys Arg Ala Ser Glu Lys Leu Arg
    50                  55                  60

Gln Phe Leu Asp Asp Asn Ser Thr Gly Asp Phe Asp Asp His Leu Leu
65                  70                  75                  80

Lys Val Ser Glu Gly Thr Gln Thr Leu Leu Asn Cys Thr Gly Gln Gly
                85                  90                  95

Lys Gly Arg Lys Pro Ala Ala Leu Gly Glu Ala Gln Pro Thr Lys Ser
            100                 105                 110

Leu Glu Glu Asn Lys Ser Ser Lys Glu Gln Lys Lys Leu Asn Asp Ala
        115                 120                 125

Cys Phe Leu Lys Arg Leu Leu Gln Glu Ile Lys Thr Cys Trp Asn Lys
    130                 135                 140

Ile Leu Lys Gly Ser
145


<210> SEQ ID NO 28
<211> LENGTH: 450
<212> TYPE: DNA
<213> ORGANISM: Artificial Sequence
<220> FEATURE:
<223> OTHER INFORMATION: Nucleic acid sequence encoding mature human
      DeI-IL-7.3.

<400> SEQUENCE: 28

gattgtgata ttgaaggtaa agatggcaaa caatatgaga gtgttctaat ggtcagcatc     60

gatcaattag acgacagcat gaaagaaacc ggtagcaatt gcctgaataa tgaacctaac    120

tttttaaaa gacatatctg tgatgctaat aaggaaggtg cctttttaaa gcgtgcttcc    180

gagaagttga ggcaatttct tgacgataat agcactggtg attttgatga ccacttatta    240

aaagtttcag aaggcacaca gacactcttg aactgcactg gccagggcaa aggaagaaaa    300

ccagctgccc tgggtgaagc ccaaccaaca aagagtttgg aagaaaataa atcttctaag    360

gaacagaaaa aactgaatga cgcctgtttc ctaaagagac tattacaaga gataaaaact    420
```

-continued tgttggaata aaattttgaa aggcagctga 450

<210> SEQ ID NO 29
<211> LENGTH: 502
<212> TYPE: DNA
<213> ORGANISM: Artificial Sequence
<220> FEATURE:
<223> OTHER INFORMATION: Nucleic acid sequence encoding GGGGSGGGG linker sequence following by mature human IL-7 containing the amino acid substitutions F39P, F57N, and L128S.

<400> SEQUENCE: 29
cccgggtgct ggaggtggag gatcaggtgg tggcggtgat tgtgatattg agggtaagga 60
tggcaaacag tacgagagtg ttctaatggt gagcatcgac cagttattgg acagcatgaa 120
ggagattggg agcaattgcc tgaataacga acccaacttc tttaagagac acatctgcga 180
tgccaataag gaagggatgt ttttaaaccg tgctgcccgc aagttgaggc aattccttaa 240
aatgaacagc actggtgact ttgatctcca cctgttaaaa gtttcagaag gcaccacaat 300
cctgttgaac tgcactggcc aggtgaaagg aaggaaacct gctgccctgg gtgaagctca 360
accaacaaag agtttggagg agaataaatc tttaaaggaa cagaaaaaac tgaatgacag 420
ctgtttccta aagagactac tgcaagagat aaaaacttgc tggaataaaa tcttgatggg 480
cactaaagaa cactgactcg ag 502

<210> SEQ ID NO 30
<211> LENGTH: 1394
<212> TYPE: DNA
<213> ORGANISM: Artificial Sequence
<220> FEATURE:
<223> OTHER INFORMATION: Nucleic acid sequence of mature human Fcgamma2(h)(FN>AQ)-(linker2)-IL-7(F39P, F57N, L77D, L128S).

<400> SEQUENCE: 30
gagcccaaat cttctgacaa aactcacaca tgcccaccgt gcccaggtaa gccagcccag 60
gcctcgccct ccagctcaag gcgggacagg tgccctagag tagcctgcat ccagggacag 120
gccccagctg ggtgctgaca cgtccacctc catctcttcc tcagcaccac ctgtggcagg 180
accgtcagtc ttcctcttcc ccccaaaacc caaggacacc ctcatgatct cccggacccc 240
tgaggtcacg tgcgtggtgg tggacgtgag ccacgaagac cccgaggtcc agttcaactg 300
gtacgtggac ggcgtggagg tgcataatgc caagacaaag ccacgggagg agcaggccca 360
gagcacgttc cgtgtggtca gcgtcctcac cgttgtgcac caggactggc tgaacggcaa 420
ggagtacaag tgcaaggtct ccaacaaagg cctcccagcc cccatcgaga aaaccatctc 480
caaaaccaaa ggtgggaccc gcggggtatg agggccacat ggacagaggc cggctcggcc 540
caccctctgc cctgagagtg accgctgtac caacctctgt ccctacaggg cagccccgag 600
aaccacaggt gtacaccctg cccccatcac gggaggagat gaccaagaac caggtcagcc 660
tgacctgcct ggtcaaaggc ttctacccca gcgacatcgc cgtggagtgg gagagcaatg 720
ggcagccgga gaacaactac aagaccacac ctcccatgct ggactccgac ggctccttct 780
tcctctacag caagctcacc gtggacaaga gcaggtggca gcaggggaac gtcttctcat 840
gctccgtgat gcatgaggct ctgcacaacc actacacgca gaagagcgcc accgcgaccc 900
cgggtgctgg aggtggagga tcaggtggtg gcggtgattg tgatattgag ggtaaggatg 960
gcaaacagta cgagagtgtt ctaatggtga gcatcgacca gttattggac agcatgaagg 1020
agattgggag caattgcctg aataacgaac ccaacttctt taagagacac atctgcgatg 1080

-continued

```
ccaataagga agggatgttt ttaaaccgtg ctgcccgcaa gttgaggcaa ttccttaaaa   1140

tgaacagcac tggtgacttt gatgaccacc tgttaaaagt ttcagaaggc accacaatcc   1200

tgttgaactg cactggccag gtgaaaggaa ggaaacctgc tgccctgggt gaagctcaac   1260

caacaaagag tttggaggag aataaatctt taaaggaaca gaaaaaactg aatgacagct   1320

gtttcctaaa gagactactg caagagataa aaacttgctg gaataaaatc ttgatgggca   1380

ctaaagaaca ctga                                                     1394
```

<210> SEQ ID NO 31
<211> LENGTH: 1394
<212> TYPE: DNA
<213> ORGANISM: Artificial Sequence
<220> FEATURE:
<223> OTHER INFORMATION: Nucleic acid sequence of mature human Fcgamma2(h)-(linker2)-IL-7(F39P, F57N, L128S).

<400> SEQUENCE: 31

```
gagcccaaat cttctgacaa aactcacaca tgcccaccgt gcccaggtaa gccagcccag     60

gcctcgccct ccagctcaag gcgggacagg tgccctagag tagcctgcat ccagggacag    120

gccccagctg ggtgctgaca cgtccacctc catctcttcc tcagcaccac ctgtggcagg    180

accgtcagtc ttcctcttcc ccccaaaacc caaggacacc ctcatgatct cccggacccc    240

tgaggtcacg tgcgtggtgg tggacgtgag ccacgaagac cccgaggtcc agttcaactg    300

gtacgtggac ggcgtggagg tgcataatgc caagacaaag ccacgggagg agcagttcaa    360

cagcacgttc cgtgtggtca gcgtcctcac cgttgtgcac caggactggc tgaacggcaa    420

ggagtacaag tgcaaggtct ccaacaaagg cctcccagcc cccatcgaga aaaccatctc    480

caaaaccaaa ggtgggaccc gcggggtatg agggccacat ggacagaggc cggctcggcc    540

caccctctgc cctgagagtg accgctgtac caacctctgt ccctacaggg cagccccgag    600

aaccacaggt gtacaccctg cccccatcac gggaggagat gaccaagaac caggtcagcc    660

tgacctgcct ggtcaaaggc ttctacccca gcgacatcgc cgtggagtgg gagagcaatg    720

ggcagccgga gaacaactac aagaccacac ctcccatgct ggactccgac ggctccttct    780

tcctctacag caagctcacc gtggacaaga gcaggtggca gcaggggaac gtcttctcat    840

gctccgtgat gcatgaggct ctgcacaacc actacacaca gaagagcgcc accgcgaccc    900

cgggtgctgg aggtggagga tcaggtggtg gcggtgattg tgatattgag ggtaaggatg    960

gcaaacagta cgagagtgtt ctaatggtga gcatcgacca gttattggac agcatgaagg   1020

agattgggag caattgcctg aataacgaac ccaacttctt taagagacac atctgcgatg   1080

ccaataagga agggatgttt ttaaaccgtg ctgcccgcaa gttgaggcaa ttccttaaaa   1140

tgaacagcac tggtgacttt gatctccacc tgttaaaagt ttcagaaggc accacaatcc   1200

tgttgaactg cactggccag gtgaaaggaa ggaaacctgc tgccctgggt gaagctcaac   1260

caacaaagag tttggaggag aataaatctt taaaggaaca gaaaaaactg aatgacagct   1320

gtttcctaaa gagactactg caagagataa aaacttgctg gaataaaatc ttgatgggca   1380

ctaaagaaca ctga                                                     1394
```

<210> SEQ ID NO 32
<211> LENGTH: 1394
<212> TYPE: DNA
<213> ORGANISM: Artificial Sequence
<220> FEATURE:
<223> OTHER INFORMATION: Nucleic acid sequence of mature -continued huFcgamma2(h)-(linker2)-IL-7(F39P, F57N, L77D, and L128S).

<400> SEQUENCE: 32

```
gagcccaaat cttctgacaa aactcacaca tgcccaccgt gcccaggtaa gccagcccag     60
gcctcgccct ccagctcaag gcgggacagg tgccctagag tagcctgcat ccagggacag    120
gccccagctg ggtgctgaca cgtccacctc catctcttcc tcagcaccac ctgtggcagg    180
accgtcagtc ttcctcttcc ccccaaaacc caaggacacc ctcatgatct cccggacccc    240
tgaggtcacg tgcgtggtgg tggacgtgag ccacgaagac cccgaggtcc agttcaactg    300
gtacgtggac ggcgtggagg tgcataatgc caagacaaag ccacgggagg agcagttcaa    360
cagcacgttc cgtgtggtca gcgtcctcac cgttgtgcac caggactggc tgaacggcaa    420
ggagtacaag tgcaaggtct ccaacaaagg cctcccagcc cccatcgaga aaaccatctc    480
caaaaccaaa ggtgggaccc gcggggtatg agggccacat ggacagaggc cggctcggcc    540
caccctctgc cctgagagtg accgctgtac caacctctgt ccctacaggg cagccccgag    600
aaccacaggt gtacaccctg cccccatcac gggaggagat gaccaagaac caggtcagcc    660
tgacctgcct ggtcaaaggc ttctacccca gcgacatcgc cgtggagtgg gagagcaatg    720
ggcagccgga gaacaactac aagaccacac ctcccatgct ggactccgac ggctccttct    780
tcctctacag caagctcacc gtggacaaga gcaggtggca gcaggggaac gtcttctcat    840
gctccgtgat gcatgaggct ctgcacaacc actacacaca gaagagcgcc accgcgaccc    900
cgggtgctgg aggtggagga tcaggtggtg gcggtgattg tgatattgag ggtaaggatg    960
gcaaacagta cgagagtgtt ctaatggtga gcatcgacca gttattggac agcatgaagg   1020
agattgggag caattgcctg aataacgaac ccaacttctt taagagacac atctgcgatg   1080
ccaataagga agggatgttt ttaaaccgtg ctgcccgcaa gttgaggcaa ttccttaaaa   1140
tgaacagcac tggtgacttt gatgaccacc tgttaaaagt ttcagaaggc accacaatcc   1200
tgttgaactg cactggccag gtgaaaggaa ggaaacctgc tgccctgggt gaagctcaac   1260
caacaaagag tttggaggag aataaatctt taaaggaaca gaaaaaactg aatgacagct   1320
gtttcctaaa gagactactg caagagataa aaacttgctg gaataaaatc ttgatgggca   1380
ctaaagaaca ctga                                                     1394
```

<210> SEQ ID NO 33
<211> LENGTH: 392
<212> TYPE: PRT
<213> ORGANISM: Artificial Sequence
<220> FEATURE:
<223> OTHER INFORMATION: Amino acid sequence of mature human Fcgamma2(h)(FN>AQ)-(linker2)-IL-7(F39P, F57N, L77D, L128S).

<400> SEQUENCE: 33

```
Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val Val His Gln Asp
```

-continued

```
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Ala Thr Ala Thr Pro Gly Ala Gly Gly Gly Gly Ser Gly Gly Gly Gly
225                 230                 235                 240

Asp Cys Asp Ile Glu Gly Lys Asp Gly Lys Gln Tyr Glu Ser Val Leu
                245                 250                 255

Met Val Ser Ile Asp Gln Leu Leu Asp Ser Met Lys Glu Ile Gly Ser
            260                 265                 270

Asn Cys Leu Asn Asn Glu Pro Asn Phe Phe Lys Arg His Ile Cys Asp
        275                 280                 285

Ala Asn Lys Glu Gly Met Phe Leu Asn Arg Ala Ala Arg Lys Leu Arg
    290                 295                 300

Gln Phe Leu Lys Met Asn Ser Thr Gly Asp Phe Asp Asp His Leu Leu
305                 310                 315                 320

Lys Val Ser Glu Gly Thr Thr Ile Leu Leu Asn Cys Thr Gly Gln Val
                325                 330                 335

Lys Gly Arg Lys Pro Ala Ala Leu Gly Glu Ala Gln Pro Thr Lys Ser
            340                 345                 350

Leu Glu Glu Asn Lys Ser Leu Lys Glu Gln Lys Lys Leu Asn Asp Ser
        355                 360                 365

Cys Phe Leu Lys Arg Leu Leu Gln Glu Ile Lys Thr Cys Trp Asn Lys
    370                 375                 380

Ile Leu Met Gly Thr Lys Glu His
385                 390


<210> SEQ ID NO 34
<211> LENGTH: 392
<212> TYPE: PRT
<213> ORGANISM: Artificial Sequence
<220> FEATURE:
<223> OTHER INFORMATION: Amino acid sequence of mature human
      Fcgamma2(h)(FN>AQ)-(linker2)-IL-7(F39P, F57N, L128S).

<400> SEQUENCE: 34

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45
```

-continued

```
Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Ala
65                  70                  75                  80

Gln Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Ala Thr Ala Thr Pro Gly Ala Gly Gly Gly Gly Ser Gly Gly Gly Gly
225                 230                 235                 240

Asp Cys Asp Ile Glu Gly Lys Asp Gly Lys Gln Tyr Glu Ser Val Leu
                245                 250                 255

Met Val Ser Ile Asp Gln Leu Leu Asp Ser Met Lys Glu Ile Gly Ser
            260                 265                 270

Asn Cys Leu Asn Asn Glu Pro Asn Phe Phe Lys Arg His Ile Cys Asp
        275                 280                 285

Ala Asn Lys Glu Gly Met Phe Leu Asn Arg Ala Ala Arg Lys Leu Arg
    290                 295                 300

Gln Phe Leu Lys Met Asn Ser Thr Gly Asp Phe Asp Leu His Leu Leu
305                 310                 315                 320

Lys Val Ser Glu Gly Thr Thr Ile Leu Leu Asn Cys Thr Gly Gln Val
                325                 330                 335

Lys Gly Arg Lys Pro Ala Ala Leu Gly Glu Ala Gln Pro Thr Lys Ser
            340                 345                 350

Leu Glu Glu Asn Lys Ser Leu Lys Glu Gln Lys Lys Leu Asn Asp Ser
        355                 360                 365

Cys Phe Leu Lys Arg Leu Leu Gln Glu Ile Lys Thr Cys Trp Asn Lys
    370                 375                 380

Ile Leu Met Gly Thr Lys Glu His
385                 390
```

<210> SEQ ID NO 35
<211> LENGTH: 392
<212> TYPE: PRT
<213> ORGANISM: Artificial Sequence
<220> FEATURE:
<223> OTHER INFORMATION: Amino acid sequence of mature human
      Fcgamma2(h)-(linker2)-IL-7(F39P, F57N, L77D, L128S).

<400> SEQUENCE: 35

```
Glu Pro Lys Ser Ser Asp Lys Thr His Thr Cys Pro Pro Cys Pro Ala
1               5                   10                  15
```

-continued

```
Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Ala Thr Ala Thr Pro Gly Ala Gly Gly Gly Gly Ser Gly Gly Gly Gly
225                 230                 235                 240

Asp Cys Asp Ile Glu Gly Lys Asp Gly Lys Gln Tyr Glu Ser Val Leu
                245                 250                 255

Met Val Ser Ile Asp Gln Leu Leu Asp Ser Met Lys Glu Ile Gly Ser
            260                 265                 270

Asn Cys Leu Asn Asn Glu Pro Asn Phe Phe Lys Arg His Ile Cys Asp
        275                 280                 285

Ala Asn Lys Glu Gly Met Phe Leu Asn Arg Ala Ala Arg Lys Leu Arg
    290                 295                 300

Gln Phe Leu Lys Met Asn Ser Thr Gly Asp Phe Asp Asp His Leu Leu
305                 310                 315                 320

Lys Val Ser Glu Gly Thr Thr Ile Leu Leu Asn Cys Thr Gly Gln Val
                325                 330                 335

Lys Gly Arg Lys Pro Ala Ala Leu Gly Glu Ala Gln Pro Thr Lys Ser
            340                 345                 350

Leu Glu Glu Asn Lys Ser Leu Lys Glu Gln Lys Lys Leu Asn Asp Ser
        355                 360                 365

Cys Phe Leu Lys Arg Leu Leu Gln Glu Ile Lys Thr Cys Trp Asn Lys
    370                 375                 380

Ile Leu Met Gly Thr Lys Glu His
385                 390
```

<210> SEQ ID NO 36
<211> LENGTH: 392
<212> TYPE: PRT
<213> ORGANISM: Artificial Sequence
<220> FEATURE:

-continued

<223> OTHER INFORMATION: Amino acid sequence of mature human Fcgamma2(h)
      (linker2)-IL-7(F39P, F57N, L128S).

<400> SEQUENCE: 36

Glu Pro Lys Ser Ser Asp Lys Thr His Thr Cys Pro Pro Cys Pro Ala
1               5                   10                  15

Pro Pro Val Ala Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Gln Phe Asn Trp Tyr Val Asp
    50                  55                  60

Gly Val Glu Val His Asn Ala Lys Thr Lys Pro Arg Glu Glu Gln Phe
65                  70                  75                  80

Asn Ser Thr Phe Arg Val Val Ser Val Leu Thr Val Val His Gln Asp
                85                  90                  95

Trp Leu Asn Gly Lys Glu Tyr Lys Cys Lys Val Ser Asn Lys Gly Leu
            100                 105                 110

Pro Ala Pro Ile Glu Lys Thr Ile Ser Lys Thr Lys Gly Gln Pro Arg
        115                 120                 125

Glu Pro Gln Val Tyr Thr Leu Pro Pro Ser Arg Glu Glu Met Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Met Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Ala Thr Ala Thr Pro Gly Ala Gly Gly Gly Gly Ser Gly Gly Gly Gly
225                 230                 235                 240

Asp Cys Asp Ile Glu Gly Lys Asp Gly Lys Gln Tyr Glu Ser Val Leu
                245                 250                 255

Met Val Ser Ile Asp Gln Leu Leu Asp Ser Met Lys Glu Ile Gly Ser
            260                 265                 270

Asn Cys Leu Asn Asn Glu Pro Asn Phe Phe Lys Arg His Ile Cys Asp
        275                 280                 285

Ala Asn Lys Glu Gly Met Phe Leu Asn Arg Ala Ala Arg Lys Leu Arg
    290                 295                 300

Gln Phe Leu Lys Met Asn Ser Thr Gly Asp Phe Asp Leu His Leu Leu
305                 310                 315                 320

Lys Val Ser Glu Gly Thr Thr Ile Leu Leu Asn Cys Thr Gly Gln Val
                325                 330                 335

Lys Gly Arg Lys Pro Ala Ala Leu Gly Glu Ala Gln Pro Thr Lys Ser
            340                 345                 350

Leu Glu Glu Asn Lys Ser Leu Lys Glu Gln Lys Lys Leu Asn Asp Ser
        355                 360                 365

Cys Phe Leu Lys Arg Leu Leu Gln Glu Ile Lys Thr Cys Trp Asn Lys
    370                 375                 380

Ile Leu Met Gly Thr Lys Glu His
385                 390

<210> SEQ ID NO 37
<211> LENGTH: 152
<212> TYPE: PRT
<213> ORGANISM: Homo sapiens

<400> SEQUENCE: 37

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Ile Cys Asp
        35                  40                  45

Ala Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Gln Val
                85                  90                  95

Lys Gly Arg Lys Pro Ala Ala Leu Gly Glu Ala Gln Pro Thr Lys Ser
            100                 105                 110

Leu Glu Glu Asn Lys Ser Leu Lys Glu Gln Lys Lys Leu Asn Asp Leu
        115                 120                 125

Cys Phe Leu Lys Arg Leu Leu Gln Glu Ile Lys Thr Cys Trp Asn Lys
    130                 135                 140

Ile Leu Met Gly Thr Lys Glu His
145                 150
```

<210> SEQ ID NO 38
<211> LENGTH: 126
<212> TYPE: PRT
<213> ORGANISM: Pan troglodytes

<400> SEQUENCE: 38

```
Met Lys Glu Ile Gly Ser Asn Cys Leu Asn Asn Glu Phe Asn Phe Phe
1               5                   10                  15

Lys Arg His Ile Cys Asp Ala Asn Lys Glu Gly Met Phe Leu Phe Arg
            20                  25                  30

Ala Ala Arg Lys Leu Arg Gln Phe Leu Lys Met Asn Ser Thr Gly Asp
        35                  40                  45

Phe Asp Leu His Leu Leu Lys Val Ser Glu Gly Thr Thr Ile Leu Leu
    50                  55                  60

Asn Cys Thr Gly Gln Val Lys Gly Arg Lys Pro Ala Ala Leu Gly Glu
65                  70                  75                  80

Ala Gln Pro Thr Lys Ser Leu Glu Glu Asn Lys Ser Leu Lys Glu Gln
                85                  90                  95

Lys Lys Leu Asn Asp Leu Cys Phe Leu Lys Arg Leu Leu Gln Glu Ile
            100                 105                 110

Lys Thr Cys Trp Asn Lys Ile Leu Met Gly Thr Lys Glu His
        115                 120                 125
```

<210> SEQ ID NO 39
<211> LENGTH: 152
<212> TYPE: PRT
<213> ORGANISM: Papio sp.

<400> SEQUENCE: 39

-continued

```
Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Leu Cys Asp
        35                  40                  45

Asp Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Lys Val
                85                  90                  95

Lys Gly Arg Lys Pro Ala Ala Leu Gly Glu Pro Gln Pro Thr Lys Ser
            100                 105                 110

Leu Glu Glu Asn Lys Ser Leu Lys Glu Gln Lys Lys Leu Asn Asp Ser
        115                 120                 125

Cys Phe Leu Lys Arg Leu Leu Gln Lys Ile Lys Thr Cys Trp Asn Lys
    130                 135                 140

Ile Leu Met Gly Thr Lys Glu His
145                 150


<210> SEQ ID NO 40
<211> LENGTH: 152
<212> TYPE: PRT
<213> ORGANISM: Macaca mulatta

<400> SEQUENCE: 40

Asp Cys Asp Ile Glu Gly Lys Asp Gly Lys Gln Tyr Glu Ser Val Leu
1               5                   10                  15

Met Val Ser Ile Asp Gln Leu Leu Asp Ser Met Lys Glu Ile Gly Ser
            20                  25                  30

Asn Cys Leu Asn Asn Glu Phe Asn Phe Phe Lys Arg His Leu Cys Asp
        35                  40                  45

Asp Asn Lys Glu Gly Met Phe Leu Phe Arg Ala Ala Arg Lys Leu Arg
    50                  55                  60

Gln Phe Leu Lys Met Asn Ser Thr Gly Asp Phe Asp Leu His Leu Leu
65                  70                  75                  80

Lys Val Ser Glu Gly Thr Thr Ile Leu Leu Asn Cys Thr Gly Lys Val
                85                  90                  95

Lys Gly Arg Lys Pro Ala Ala Leu Gly Glu Pro Gln Pro Thr Lys Ser
            100                 105                 110

Leu Glu Glu Asn Lys Ser Leu Lys Glu Gln Lys Lys Leu Asn Asp Ser
        115                 120                 125

Cys Phe Leu Lys Arg Leu Leu Gln Lys Ile Lys Thr Cys Trp Asn Lys
    130                 135                 140

Ile Leu Met Gly Thr Lys Glu His
145                 150


<210> SEQ ID NO 41
<211> LENGTH: 151
<212> TYPE: PRT
<213> ORGANISM: Bos taurus

<400> SEQUENCE: 41

Asp Cys Asp Ile Ser Gly Lys Asp Gly Gly Ala Tyr Gln Asn Val Leu
1               5                   10                  15
```

-continued

```
Met Val Asn Ile Asp Asp Leu Asp Asn Met Ile Asn Phe Asp Ser Asn
            20                  25                  30

Cys Leu Asn Asn Glu Pro Asn Phe Phe Lys Lys His Ser Cys Asp Asp
        35                  40                  45

Asn Lys Glu Ala Ser Phe Leu Asn Arg Ala Ser Arg Lys Leu Arg Gln
    50                  55                  60

Phe Leu Lys Met Asn Ile Ser Asp Asp Phe Lys Leu His Leu Ser Thr
65                  70                  75                  80

Val Ser Gln Gly Thr Leu Thr Leu Leu Asn Cys Thr Ser Lys Gly Lys
                85                  90                  95

Gly Arg Lys Pro Pro Ser Leu Ser Glu Ala Gln Pro Thr Lys Asn Leu
            100                 105                 110

Glu Glu Asn Lys Ser Ser Lys Glu Gln Lys Lys Gln Asn Asp Leu Cys
        115                 120                 125

Phe Leu Lys Ile Leu Leu Gln Lys Ile Lys Thr Cys Trp Asn Lys Ile
    130                 135                 140

Leu Arg Gly Ile Lys Glu His
145                 150


<210> SEQ ID NO 42
<211> LENGTH: 151
<212> TYPE: PRT
<213> ORGANISM: Sus scrofa

<400> SEQUENCE: 42

Asp Cys Asp Ile Glu Gly Lys Asp Gly Gly Val Tyr Gln Asn Val Leu
1               5                   10                  15

Met Val Ser Ile Asp Asp Leu Asp Arg Met Ile Asp Phe Asp Ser Asn
            20                  25                  30

Cys Leu Asn Asn Glu Pro Asn Phe Leu Lys Lys His Ser Cys Asp Asp
        35                  40                  45

Asn Lys Glu Ala Ser Phe Leu Tyr Arg Ala Ala Arg Lys Leu Lys Gln
    50                  55                  60

Phe Ile Lys Met Asn Ile Ser Glu Glu Phe Asn His His Leu Ser Thr
65                  70                  75                  80

Val Ser Gln Gly Thr Leu Thr Leu Phe Asn Cys Thr Ser Lys Val Lys
                85                  90                  95

Gly Arg Lys Pro Pro Ser Leu Gly Glu Ala Gln Leu Thr Lys Asn Leu
            100                 105                 110

Glu Glu Asn Lys Ser Leu Lys Glu Gln Lys Arg Gln Gly Asp Leu Cys
        115                 120                 125

Phe Leu Lys Ile Leu Leu Gln Lys Ile Lys Thr Cys Trp Asn Lys Ile
    130                 135                 140

Leu Arg Gly Ala Lys Glu Tyr
145                 150


<210> SEQ ID NO 43
<211> LENGTH: 151
<212> TYPE: PRT
<213> ORGANISM: Ovis aries

<400> SEQUENCE: 43

Asp Cys Asp Phe Ser Gly Lys Asp Gly Gly Ala Tyr Gln Asn Val Leu
1               5                   10                  15

Met Val Ser Ile Asp Asp Leu Asp Asn Met Ile Asn Phe Asp Ser Asn
            20                  25                  30
```

-continued

Cys Leu Asn Asn Glu Pro Asn Phe Phe Lys Lys His Ser Cys Asp Asp
35 40 45

Asn Lys Glu Ala Ser Phe Leu Asn Arg Ala Ala Arg Lys Leu Lys Gln
50 55 60

Phe Leu Lys Met Asn Ile Ser Asp Asp Phe Lys Leu His Leu Ser Thr
65 70 75 80

Val Ser Gln Gly Thr Leu Thr Leu Leu Asn Cys Thr Ser Lys Gly Lys
85 90 95

Gly Arg Lys Pro Pro Ser Leu Gly Glu Ala Gln Pro Thr Lys Asn Leu
100 105 110

Glu Glu Asn Lys Ser Leu Lys Glu Gln Arg Lys Gln Asn Asp Leu Cys
115 120 125

Phe Leu Lys Ile Leu Leu Gln Lys Ile Lys Thr Cys Trp Asn Lys Ile
130 135 140

Leu Arg Gly Ile Thr Glu His
145 150

<210> SEQ ID NO 44
<211> LENGTH: 129
<212> TYPE: PRT
<213> ORGANISM: Rattus norvegicus

<400> SEQUENCE: 44

Asp Cys His Ile Lys Asp Lys Asp Gly Lys Ala Phe Gly Ser Val Leu
1 5 10 15

Met Ile Ser Ile Asn Gln Leu Asp Lys Met Thr Gly Thr Asp Ser Asp
20 25 30

Cys Pro Asn Asn Glu Pro Asn Phe Phe Lys Lys His Leu Cys Asp Asp
35 40 45

Thr Lys Glu Ala Ala Phe Leu Asn Arg Ala Ala Arg Lys Leu Arg Gln
50 55 60

Phe Leu Lys Met Asn Ile Ser Glu Glu Phe Asn Asp His Leu Leu Arg
65 70 75 80

Val Ser Asp Gly Thr Gln Thr Leu Val Asn Cys Thr Ser Lys Glu Glu
85 90 95

Lys Thr Ile Lys Glu Gln Lys Lys Asn Asp Pro Cys Phe Leu Lys Arg
100 105 110

Leu Leu Arg Glu Ile Lys Thr Cys Trp Asn Lys Ile Leu Lys Gly Ser
115 120 125

Ile

<210> SEQ ID NO 45
<211> LENGTH: 129
<212> TYPE: PRT
<213> ORGANISM: Mus musculus

<400> SEQUENCE: 45

Glu Cys His Ile Lys Asp Lys Glu Gly Lys Ala Tyr Glu Ser Val Leu
1 5 10 15

Met Ile Ser Ile Asp Glu Leu Asp Lys Met Thr Gly Thr Asp Ser Asn
20 25 30

Cys Pro Asn Asn Glu Pro Asn Phe Phe Arg Lys His Val Cys Asp Asp
35 40 45

Thr Lys Glu Ala Ala Phe Leu Asn Arg Ala Ala Arg Lys Leu Lys Gln
50 55 60

Phe Leu Lys Met Asn Ile Ser Glu Glu Phe Asn Val His Leu Leu Thr

-continued 65 70 75 80

Val Ser Gln Gly Thr Gln Thr Leu Val Asn Cys Thr Ser Lys Glu Glu
85 90 95

Lys Asn Val Lys Glu Gln Lys Lys Asn Asp Ala Cys Phe Leu Lys Arg
100 105 110

Leu Leu Arg Glu Ile Lys Thr Cys Trp Asn Lys Ile Leu Lys Gly Ser
115 120 125

Ile

<210> SEQ ID NO 46
<211> LENGTH: 18
<212> TYPE: PRT
<213> ORGANISM: Homo sapiens

<400> SEQUENCE: 46

Val Lys Gly Arg Lys Pro Ala Ala Leu Gly Glu Ala Gln Pro Thr Lys
1 5 10 15

Ser Leu

<210> SEQ ID NO 47
<211> LENGTH: 8
<212> TYPE: PRT
<213> ORGANISM: Artificial Sequence
<220> FEATURE:
<223> OTHER INFORMATION: N-terminal sequence of bacterially produced human IL-7 protein.

<400> SEQUENCE: 47

Met Asp Cys Asp Ile Glu Gly Lys
1 5

<210> SEQ ID NO 48
<211> LENGTH: 9
<212> TYPE: PRT
<213> ORGANISM: Artificial Sequence
<220> FEATURE:
<223> OTHER INFORMATION: A T cell epitope present in IL-7 including position 70.

<400> SEQUENCE: 48

Leu Arg Gln Phe Leu Lys Met Asn Ser
1 5

<210> SEQ ID NO 49
<211> LENGTH: 9
<212> TYPE: PRT
<213> ORGANISM: Artificial Sequence
<220> FEATURE:
<223> OTHER INFORMATION: A T-cell epitope present in IL-7 including position 70.

<400> SEQUENCE: 49

Phe Leu Lys Met Asn Ser Thr Gly Asp
1 5

<210> SEQ ID NO 50
<211> LENGTH: 9
<212> TYPE: PRT
<213> ORGANISM: Artificial Sequence
<220> FEATURE:
<223> OTHER INFORMATION: A T-cell epitope present in IL-7 including position 70.

<400> SEQUENCE: 50

-continued

Leu Lys Met Asn Ser Thr Gly Asp Phe
1 5

<210> SEQ ID NO 51
<211> LENGTH: 9
<212> TYPE: PRT
<213> ORGANISM: Artificial Sequence
<220> FEATURE:
<223> OTHER INFORMATION: A T-cell epitope present in IL-7 including position 70.

<400> SEQUENCE: 51

Met Asn Ser Thr Gly Asp Phe Asp Leu
1 5

<210> SEQ ID NO 52
<211> LENGTH: 9
<212> TYPE: PRT
<213> ORGANISM: Artificial Sequence
<220> FEATURE:
<223> OTHER INFORMATION: A T-cell epitope present in IL-7 including position 91.

<400> SEQUENCE: 52

Ile Leu Leu Asn Cys Thr Gly Gln Val
1 5

<210> SEQ ID NO 53
<211> LENGTH: 9
<212> TYPE: PRT
<213> ORGANISM: Artificial Sequence
<220> FEATURE:
<223> OTHER INFORMATION: A T-cell epitope present in IL-7 including position 91.

<400> SEQUENCE: 53

Leu Leu Asn Cys Thr Gly Gln Val Lys
1 5

<210> SEQ ID NO 54
<211> LENGTH: 4
<212> TYPE: PRT
<213> ORGANISM: Artificial Sequence
<220> FEATURE:
<223> OTHER INFORMATION: A glycosylation site in Fc portion of IgG1.

<400> SEQUENCE: 54

Gln Tyr Asn Ser
1

<210> SEQ ID NO 55
<211> LENGTH: 4
<212> TYPE: PRT
<213> ORGANISM: Artificial Sequence
<220> FEATURE:
<223> OTHER INFORMATION: A glycosylation site in Fc portion of IgG1.

<400> SEQUENCE: 55

Gln Phe Asn Ser
1

<210> SEQ ID NO 56
<211> LENGTH: 4
<212> TYPE: PRT
<213> ORGANISM: Artificial Sequence
<220> FEATURE:
<223> OTHER INFORMATION: A glycosylation site in Fc portion of IgG1.

-continued

<400> SEQUENCE: 56

Gln Ala Gln Ser
1

<210> SEQ ID NO 57
<211> LENGTH: 4
<212> TYPE: PRT
<213> ORGANISM: Artificial Sequence
<220> FEATURE:
<223> OTHER INFORMATION: A sequence near the C-terminus of Fc portion.

<400> SEQUENCE: 57

Leu Ser Leu Ser
1

<210> SEQ ID NO 58
<211> LENGTH: 4
<212> TYPE: PRT
<213> ORGANISM: Artificial Sequence
<220> FEATURE:
<223> OTHER INFORMATION: A modified sequence near the C-terminus of the Fc portion.

<400> SEQUENCE: 58

Ala Thr Ala Thr
1

<210> SEQ ID NO 59
<211> LENGTH: 13
<212> TYPE: PRT
<213> ORGANISM: Artificial Sequence
<220> FEATURE:
<223> OTHER INFORMATION: A tetanus toxin derived peptide.

<400> SEQUENCE: 59

Met Gln Tyr Ile Lys Ala Asn Ser Lys Phe Ile Gly Ile
1 5 10

<210> SEQ ID NO 60
<211> LENGTH: 15
<212> TYPE: PRT
<213> ORGANISM: Artificial Sequence
<220> FEATURE:
<223> OTHER INFORMATION: A peptide containing a T-cell epitope.

<400> SEQUENCE: 60

Ala Arg Lys Leu Arg Gln Phe Leu Lys Met Asn Ser Thr Gly Asp
1 5 10 15

<210> SEQ ID NO 61
<211> LENGTH: 15
<212> TYPE: PRT
<213> ORGANISM: Artificial Sequence
<220> FEATURE:
<223> OTHER INFORMATION: A peptide containing a T-cell epitope.

<400> SEQUENCE: 61

Leu Arg Gln Phe Leu Lys Met Asn Ser Thr Gly Asp Phe Asp Leu
1 5 10 15

<210> SEQ ID NO 62
<211> LENGTH: 15
<212> TYPE: PRT
<213> ORGANISM: Artificial Sequence
<220> FEATURE:
<223> OTHER INFORMATION: A peptide containing a T-cell epitope.

<400> SEQUENCE: 62

Phe Leu Lys Met Asn Ser Thr Gly Asp Phe Asp Leu His Leu Leu
1 5 10 15

<210> SEQ ID NO 63
<211> LENGTH: 9
<212> TYPE: PRT
<213> ORGANISM: Artificial Sequence
<220> FEATURE:
<223> OTHER INFORMATION: A variant IL-7 peptide sequence.

<400> SEQUENCE: 63

Leu Arg Gln Phe Leu Asp Asp Asn Ser
1 5

<210> SEQ ID NO 64
<211> LENGTH: 9
<212> TYPE: PRT
<213> ORGANISM: Artificial Sequence
<220> FEATURE:
<223> OTHER INFORMATION: A variant IL-7 peptide sequence.

<400> SEQUENCE: 64

Thr Leu Leu Asn Cys Thr Gly Gln Gly
1 5

<210> SEQ ID NO 65
<211> LENGTH: 16
<212> TYPE: PRT
<213> ORGANISM: Artificial Sequence
<220> FEATURE:
<223> OTHER INFORMATION: A peptide containing a T-cell epitope.

<400> SEQUENCE: 65

Leu Arg Gln Phe Leu Lys Met Asn Ser Thr Gly Asp Phe Asp Leu Cys
1 5 10 15

<210> SEQ ID NO 66
<211> LENGTH: 16
<212> TYPE: PRT
<213> ORGANISM: Artificial Sequence
<220> FEATURE:
<223> OTHER INFORMATION: A peptide containing a T-cell epitope.

<400> SEQUENCE: 66

Cys Leu Arg Gln Phe Leu Lys Met Asn Ser Thr Gly Asp Phe Asp Leu
1 5 10 15

<210> SEQ ID NO 67
<211> LENGTH: 5
<212> TYPE: PRT
<213> ORGANISM: Artificial Sequence
<220> FEATURE:
<223> OTHER INFORMATION: A sequence containing a glycosylation site.

<400> SEQUENCE: 67

Met Asn Ser Thr Gly
1 5

<210> SEQ ID NO 68
<211> LENGTH: 5
<212> TYPE: PRT
<213> ORGANISM: Artificial Sequence
<220> FEATURE:
<223> OTHER INFORMATION: A sequence containing a glycosylation site.

<400> SEQUENCE: 68

-continued

```
Leu Asn Cys Thr Gly
1               5


<210> SEQ ID NO 69
<211> LENGTH: 30
<212> TYPE: DNA
<213> ORGANISM: Artificial Sequence
<220> FEATURE:
<223> OTHER INFORMATION: Primer M(s).

<400> SEQUENCE: 69

tgactttgat gaccacctgt taaaagtttc                                         30


<210> SEQ ID NO 70
<211> LENGTH: 28
<212> TYPE: DNA
<213> ORGANISM: Artificial Sequence
<220> FEATURE:
<223> OTHER INFORMATION: Primer M(a).

<400> SEQUENCE: 70

aacaggtggt catcaaagtc accagtgc                                           28


<210> SEQ ID NO 71
<211> LENGTH: 28
<212> TYPE: DNA
<213> ORGANISM: Artificial Sequence
<220> FEATURE:
<223> OTHER INFORMATION: Downstream primer.

<400> SEQUENCE: 71

ctcgagtcag tgttctttag tgcccatc                                           28


<210> SEQ ID NO 72
<211> LENGTH: 29
<212> TYPE: DNA
<213> ORGANISM: Artificial Sequence
<220> FEATURE:
<223> OTHER INFORMATION: Upsteam primer.

<400> SEQUENCE: 72

cccgggtgct ggaggtggag gatcaggtg                                          29
```

IL-7 VARIANTS WITH REDUCED IMMUNOGENICITY

CROSS REFERENCE TO RELATED APPLICATIONS

This application claims priority to and the benefit of U.S. Provisional Patent Application No. 60/634,470, filed on Dec. 9, 2004, the entire disclosure of which is incorporated by reference herein.

FIELD OF THE INVENTION

The invention relates generally to IL-7 moieties modified to reduce their immunogenicity.

BACKGROUND

Cytokines are stimulators of the immune system and are thus useful as drugs. For example, interferon-alpha (IFN-α), interferon-beta (IFN-β), interleukin-2 (IL-2), and granulocyte/macrophage-colony stimulating factor (GM-CSF) are all approved drugs used to treat viral infections, cancer, immune system misregulation such as autoimmune disease, and to promote recovery of the immune system after cancer chemotherapy. Unfortunately, these proteins can stimulate an immune response against themselves, causing patients to develop antibodies against the therapeutic protein. These antibodies can also inhibit function of the same protein endogenously produced within the patient, resulting in potential long-term consequences for patient health.

Interleukin-7 is a cytokine that promotes survival and proliferation of T-cells, B-cells, and other immune cells. It is also potentially a therapeutic protein to treat patients whose immune systems have been damaged by cancer chemotherapy, HIV infection, or other diseases, disorders, or chemical exposures. However, based on its immunostimulatory properties, therapeutically administered IL-7 is expected to induce an antibody response against itself. Therefore, there is a need in the art for improved versions of IL-7 that are less immunogenic, but that retain the property of stimulating the immune system.

SUMMARY OF THE INVENTION

The present invention is directed to interleukin-7 (IL-7) which has been modified to reduce its immunogenicity in comparison to wild-type IL-7. More specifically, the IL-7 proteins of the invention are modified to remove potential T-cell epitopes. As a result, IL-7 proteins of the invention have improved biological properties compared to wild-type IL-7.

Accordingly, in one aspect, the invention features a polypeptide at least 80% identical to a human IL-7 moiety or an active portion thereof, comprising an amino acid substitution at one or more residues corresponding to Gln22, Leu24, Ile30, Phe39, Met54, Phe57, Arg58, Ala60, Leu63, Lys68, Met69, Leu77, Ile88, Val96, Leu104, Leu128, Met147, Thr149, or Lys150. These amino acid modifications can be used singly or in combination to reduce an anti-IL-7 T-cell response. Thus, the invention encompasses IL-7 moieties with for example, one, at least two, at least four, or at least eight amino acid modifications at positions selected from Gln22, Leu24, Ile30, Phe39, Met54, Phe57, Arg58, Ala60, Leu63, Lys68, Met 69, Leu77, Ile88, Val96, Leu104, Leu128, Met147, Thr149, and Lys150. In one embodiment, the IL-7 moiety incorporates one, two, three, four, five or more of the following substitutions: Gln22Asp, Leu24Asp, Ile30Thr, Phe39Pro, Met54Ala, Phe57Lys, Phe57Asn, Arg58Asp, Ala60Ser, Arg61Glu, Leu77Asp, Leu104Ser, Leu104Val, Leu128Ala, Leu128Val, Leu128Pro, Leu128Ser, Met147Lys, Thr149Ser, or Lys150Stop.

In one embodiment, the polypeptide contains a substitution or substitutions at one or more at Phe39, Phe57, Leu77, and Leu128. In a further embodiment, the polypeptide has one or more of substitutions Phe39Pro, Phe57Asn, Leu77Asp, and Leu128Ser. In another embodiment, the polypeptide includes the substitutions Phe39Pro, Phe57Asn, Leu77Asp, and Leu128Ser, while in a further embodiment, the polypeptide includes the substitutions Phe39Pro, Phe57Asn, and Leu128Ser.

In certain embodiments of the invention, the polypeptide with at least 80% identity with a human IL-7 moiety further comprises an immunoglobulin (Ig) moiety, such as a human Ig moiety. In one embodiment, the Ig moiety is IgG2. In some embodiments, the Ig moiety is an Fc portion. The invention also relates to a cell comprising a nucleic acid sequence encoding a polypeptide modified according to the invention. In one embodiment, the cell is a prokaryotic cell.

In a further embodiment, the polypeptide has at least 90% identity to a human IL-7 moiety or an active portion thereof, while in another embodiment, the polypeptide has at least 95% identity to a human IL-7 moiety or an active portion thereof.

The invention also features a method of treating a patient comprising administering a therapeutically effective amount of a polypeptide of the invention to, for example, a patient diagnosed with cancer or HIV. In one embodiment, the invention provides for administration of between about 0.01 and about 10 mg/kg/day or between 0.01 and 10.00 mg/kg/day of a polypeptide of the invention.

BRIEF DESCRIPTION OF THE DRAWINGS

FIG. 1 depicts the amino acid sequence for human IL-7. The signal sequence is shown in bold. Also depicted in bold and italics is a stretch of eighteen amino acids which can be deleted from the IL-7 sequence (SEQ ID NO: 1).

FIG. 2 depicts the amino acid sequence for cow IL-7. The signal sequence is shown in bold (SEQ ID NO:2).

FIG. 3 depicts the amino acid sequence for sheep IL-7. The signal sequence is shown in bold (SEQ ID NO:3).

FIG. 4 is an amino acid sequence alignment of IL-7 proteins from human (SEQ ID NO:37), chimpanzee (SEQ ID NO:38), baboon (SEQ ID NO:39), macaque (SEQ ID NO:40), bovine (SEQ ID NO:41), pig (SEQ ID NO:42), sheep (SEQ ID NO:43), rat (SEQ ID NO:44), and murine (SEQ ID NO:45) sources.

FIG. 6 shows values for the average fold change in plasma Fc-IL-7 concentrations between day 0 and day 2, and between day 2 and 4 in test mice administered Fc-IL-7 subcutaneously (SC).

FIG. 7 depicts the average organ weights of organs taken from test mice sacrificed on day 7 compared to the average organ weights of mice in the control group.

DETAILED DESCRIPTION OF THE INVENTION

Figure 5:
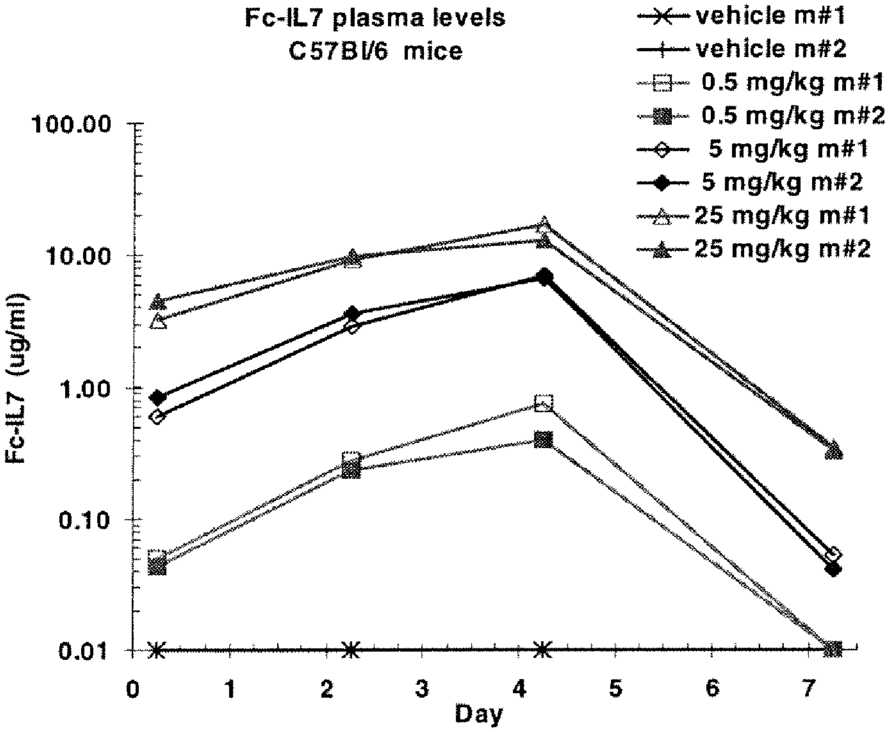
FIG. 5 depicts Fc-IL-7 plasma concentrations in μg/ml for both test mice and control mice administered Fc-IL-7 subcutaneously.

The invention is directed to IL-7 proteins that have reduced immunogenicity as compared to wild-type IL-7, as well as methods for making and using such proteins. More specifically, the invention provides mutations within IL-7 moieties that have the effect of reducing the immunogenicity of IL-7 itself, primarily by removing T-cell epitopes within IL-7 that may stimulate to an immune response. The invention also encompasses fusion proteins incorporating IL-7 moieties modified according to the teachings of the invention.

T-cell epitopes can be identified by a variety of computer and non-computer methods, including predictions based on structure-based computer modeling or by synthesis of peptides and testing for binding to specific MHC Class II molecules or in an immunogenicity assay. According to the invention, a potential T-cell epitope is a sequence that, when considered as an isolated peptide, is predicted to bind to an MHC Class II molecule or an equivalent in a non-human species. A potential T-cell epitope is defined without consideration of other aspects of antigen processing, such as the efficiency of protein uptake into antigen-presenting cells, the efficiency of cleavage at sites in an intact protein to yield a peptide that can bind to MHC Class II, and so on. Thus, the set of T-cell epitopes that are actually presented on MHC Class II after administration of a protein to an animal is a subset of the potential T-cell epitopes. According to the invention, a T-cell epitope is an epitope on a protein that interacts with an MHC class II molecule. Without wishing to be bound by theory, it is understood that a T-cell epitope is an amino acid sequence in a protein that failed to undergo the negative T-cell selection process during T-cell development and therefore will be expected to be presented by an MHC Class II molecule and recognized by a T-cell receptor.

B-cell epitopes are also identified by a variety of computer and non-computer methods, including predictions based on structure-based computer modeling or by synthesis of peptides and testing for binding to specific B-cell antigen receptor molecules or in an immunogenicity assay. According to the invention, a potential B-cell epitope is a sequence that, when considered as an isolated peptide, is predicted to bind to a B-cell antigen receptor or an equivalent in a non-human species. A B-cell epitope is an epitope that does bind or is recognized by a B-cell antigen receptor and is a subset of potential B-cell epitopes.

The invention provides methods related to reducing the immunogenicity of IL-7. According to one embodiment of the invention, potential non-self T-cell epitopes are identified in sequences of IL-7. For example, potential non-self T-cell epitopes are identified by computational methods based on modeling peptide binding to MHC Class II molecules. Substitutions are then made such that the ability of peptides containing potential T-cell epitopes to bind to MHC Class II is reduced or eliminated. This process of identifying and modifying peptides which bind to MHC Class II is termed "de-immunization" and the resultant modified protein molecules are termed "de-immunized."

According to the invention, MHC Class II binding can be removed in situations where a protein is to be produced in bacteria or in an organism that does not generate a mammalian glycosylation pattern, such as yeast or insect cells.

The invention provides non-computer methods for reducing or eliminating the number of T-cell epitopes in IL-7 without requiring elaborate computer simulations or protein three-dimensional structures. In one embodiment, a method of the invention takes advantage of the fact that a core segment of nine amino acids interacts with both the MHC class II molecule as well as the T-cell receptor during antigen presentation. The most N-terminal amino acid, the "anchor" position, binds to a deep pocket within the MHC class II molecule. One of the following amino acids is typically present at the anchor position, which is important for binding to an MHC class II molecule: leucine, valine, isoleucine, methionine, phenylalanine, tyrosine and tryptophan. According to the invention, an additional 2 to 3 amino acids adjacent to the core 9 amino acids also affect the interaction with MHC molecules.

A general method of the invention includes mutating any leucines, valines, isoleucines, methionines, phenylalanines, tyrosines or tryptophans that occur in IL-7. In one embodiment, one or more of these amino acids in a candidate T-cell epitope is mutated to a threonine, an alanine or a proline, thereby retaining some of the hydrophobic nature of the amino acid that is replaced. In further embodiments of the invention, one or more of the above-mentioned amino acids is deleted from a candidate T-cell epitope or potential T-cell epitope, or replaced with an appropriate amino acid analog. According to the invention, if an amino acid is deleted to destroy a potential T-cell epitope, care should be taken not to generate a new T-cell epitope that includes amino acids near the deletion.

Thus, the invention provides nucleic acid sequences and proteins that are useful in construction of less immunogenic IL-7 proteins. Specifically, the invention provides proteins with mutations of leucines, valines, isoleucines, methionines, phenylalanines, tyrosines, or tryptophans. Any aliphatic or aromatic residue (leucine, valine, isoleucine, methionine, phenylalanine, tryptophan or tyrosine) presents a high risk of creating an MHC binding peptide with the amino acid in the first position (anchor position) that binds the pocket of the MHC molecule. Therefore, substitution of any of the above-mentioned amino acids, with an amino acid that is not one of the above-mentioned amino acids, or with alanine, proline, or threonine, will remove a candidate T-cell epitope.

The proteins can be human proteins with sequences that generally correspond to sequences found in the human body. The invention also provides nucleic acid sequences encoding such proteins. The nucleic acid sequences for this aspect of the invention may exist as plasmids, PCR-generated fragments, or nucleic acids produced by chemical synthesis.

As used herein, the term "interleukin-7" or "IL-7" means IL-7 polypeptides and derivatives and analogs thereof having substantial amino acid sequence identity to wild-type mature mammalian IL-7. For example, IL-7 refers to an amino acid sequence of a recombinant or non-recombinant polypeptide having an amino acid sequence of: i) a native or naturally-occurring allelic variant of an IL-7 polypeptide, ii) a biologically active fragment of an IL-7 polypeptide, iii) a biologically active polypeptide analog of an IL-7 polypeptide, or iv) a biologically active variant of an IL-7 polypeptide.

IL-7 polypeptides modified according to the invention can be derived from any species, e.g., human, cow or sheep. IL-7 nucleic acid and amino acid sequences are well known in the art. For example, the human IL-7 amino acid sequence has a Genbank accession number of NM 000880 and is shown in FIG. 1 (SEQ ID NO:1); the mouse IL-7 amino acid sequence has a Genbank accession number of NM 008371; the rat IL-7 amino acid sequence has a Genbank accession number of AF 367210; the cow IL-7 amino acid sequence has a Genbank accession number of NM 173924 and is shown in FIG. 2 (SEQ ID NO:2); and the sheep IL-7 amino acid sequence has a Genbank accession number of U10089 and is shown in FIG. 3 (SEQ ID NO:3). The signal sequence for each of the polypeptide species is shown in bold in each of the figures and is typically not included where the IL-7 portion is fused C-terminal to the carrier protein.

In addition, in FIG. 4, an alignment of various mammalian IL-7 sequences is shown. IL-7 from non-human primates is generally more than 90% identical to human IL-7. Although the murine IL-7 sequence is the most divergent from the human IL-7 sequence, with less than 70% identity, it is nevertheless capable or activating the human IL-7 receptor. Therefore, IL-7 moieties from a range of species are particularly useful in accordance with the teachings of the invention.

A "variant" of an IL-7 protein is defined as an IL-7 amino acid sequence that is altered by one or more amino acids as compared to wild-type IL-7. The variant can have "conservative" changes, wherein a substituted amino acid has similar structural or chemical properties, e.g., replacement of leucine with isoleucine. More rarely, a variant can have "nonconservative" changes, e.g., replacement of a glycine with a tryptophan. Similar minor variations can also include amino acid deletions or insertions, or both.

Variant IL-7 proteins also include polypeptides that have at least about 70%, 75%, 80%, 81%, 82%, 83%, 84%, 85%, 86%, 87%, 88%, 89%, 90%, 91%, 92%, 93%, 94%, 95%, 96%, 97%, 98%, 99%, or more sequence identity with wild-type IL-7. To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino acid or nucleic acid sequence). The percent identity between the two sequences is a function of the number of identical positions shared by the sequences (i.e., % homology=(# of identical positions/total # of positions)times 100). The determination of percent homology between two sequences can be accomplished using a mathematical algorithm. A non-limiting example of a mathematical algorithm utilized for the comparison of two sequences is the algorithm of Karlin and Altschul, (1990) *Proc. Natl. Acad. Sci. USA,* 87:2264-68, modified as in Karlin and Altschul, (1993) *Proc. Natl. Acad. Sci. USA,* 90:5873-77. Such an algorithm is incorporated into the NBLAST and XBLAST programs of Altschul et al., (1990) *J. Mol. Biol.,* 215:403-10. BLAST nucleotide searches can be performed with the NBLAST program, score=100, wordlength=12. BLAST protein searches can be performed with the XBLAST program, score=50, wordlength=3. To obtain gapped alignments for comparison purposes, Gapped BLAST can be utilized as described in Altschul et al., (1997) *Nucleic Acids Research,* 25(17):3389-3402. When utilizing BLAST and Gapped BLAST programs, the default parameters of the respective programs (e.g., XBLAST and NBLAST) can be used.

Furthermore, the invention also includes IL-7 fusion proteins wherein the IL-7 moiety contains a deletion and which retain comparable activity compared to the corresponding unmodified IL-7 fusion proteins. For example, the invention provides a form of Ig-IL-7 or IL-7 in which the IL-7 moiety contains an eighteen amino acid internal deletion corresponding to the sequence VKGRKPAALGEAQPTKSL (SEQ ID NO:46), of wild-type human IL-7. (See FIG. 1). In addition, the invention provides an active form of IL-7 wherein Lys150 is deleted. Glu151 land His152 may also be deleted in conjunction with Lys150 while still leaving an active form of IL-7.

Throughout this application, the positions of amino acid residues in the IL-7 sequence are given with reference to the mature human IL-7 protein. For example, the cysteine in the N-terminal sequence MDCDIEGK (SEQ ID NO:47) of bacterially produced human IL-7 protein, which includes a start methionine, is still referred to as Cys2.

Modifying IL-7 Proteins

One aspect of the invention derives from the insight that IL-7 produced by bacterial expression will not contain post-translational modifications that are characteristic of eukaryotes, such as mammals. For example, IL-7 contains three predicted N-linked glycosylation sites at positions 70, 91, and 116. In an Fc-IL-7 fusion protein expressed in mammalian cells, the asparagines at positions 70 and 91 are glycosylated, while the asparagine at position 116 is not. It is likely that IL-7 endogenously produced in the human body is also N-glycosylated, at least at positions 70 and 91, and possibly at position 116. These N-linked glycosylations are not present in bacterially produced IL-7, and represent sequences that might be recognized by the human immune system as "non-self," i.e., not normally present in the human body. As such, the invention encompasses deimmunizing these potential epitope regions on IL-7 to reduce the immunogenicity of IL-7 and related proteins.

According to the invention, T-cell epitopes are present in IL-7 that include positions 70 and 91, as described in Table 1. The epitopes shown in Table 1 are defined in terms of a minimal 9-mer peptide, with the strong MHC Class II anchor residue in the first position.

TABLE 1

| T cell epitopes including position 70 | T cell epitopes including position 91 |
|---|---|
| LRQFLKMNS (SEQ ID NO: 48) | ILLNCTGQV (SEQ ID NO: 52) |
| FLKMNSTGD (SEQ ID NO: 49) | LLNCTGQVK (SEQ ID NO: 53) |
| LKMNSTGDF (SEQ ID NO: 50) | |
| MNSTGDFDL (SEQ ID NO: 51) | |

According to the invention, one method for reducing the immunogenicity of bacterially produced IL-7 is to introduce one or more of the following mutations: Leu63Ala, Leu63Val, Leu63Pro, Leu63Thr, Lys68Asp, Met69Asp, Lys68Glu, Met69Glu, Ile88Thr, Ile88Ala, Ile88Val, and Val96Gly. Other mutations may be introduced at positions 63, 68, 69, 88 and/or 94. Some mutations are particularly useful in combination, such as the pairs Lys68Asp coupled with Met69Asp and/or Ile88Thr coupled with Val96Gly.

When these mutations are introduced into IL-7 or a fusion protein comprising IL-7, the resulting mutant protein generally has enough IL-7 biological activity to be useful as a therapeutic protein. In fact, the biological activity of the IL-7 moiety is at least 10%, 20%, 50%, 70%, 80%, 90%, 95%, 99% or 100% in comparison to the biological activity of wild type IL-7. Activity of the IL-7 of the invention can be tested in an in vitro or in vivo assay. Example 9 shows an assay for testing biological activity of the IL-7 variants of the invention.

In addition, the mutations generally allow proper folding of the IL-7 moiety so that a pure protein, largely free of high-molecular weight aggregates and incorrectly disulfide-bonded forms, may be isolated. However, the folding and biological activity that results from any particular combination should be tested, for example as illustrated in the Examples, to verify that the desired activity is obtained.

According to the invention, an alternative strategy for reducing the immunogenicity of bacterially produced IL-7 is to alter Asn70 and Asn91 to aspartic acid. Without wishing to be bound by theory, the mutation of Asn70 and Asn91 to aspartic acid may be useful for the following reasons.

The immunogenicity of an exogenously administered therapeutic protein is mediated, in part, through the presentation of T-cell epitopes derived from the therapeutic protein. Such presentation is thought to occur through the following mechanism. A therapeutic protein is taken up by an antigen-presenting cell (APC), such as a dendritic cell, macrophage, or B-cell by endocytosis. The protein is transported into a series of vesicles termed endosomes, including the early, middle and late endosomes. In these vesicles, the environment becomes progressively more harsh and less favorable for extracellular, disulfide-bonded proteins that may be stably folded at neutral pH. Proteases termed cathepsins degrade internalized proteins into small peptides. A proportion of these protein fragments then become bound by MHC Class II proteins which transport the fragments to the cell surface as MHC Class II/peptide complexes. Such complexes are recognized by T-cell receptors on CD4+ T-cells.

In the case of peptides deriving from foreign proteins, presentation of an MHC Class II/peptide complex may stimulate an immune response. However, in the case of peptides deriving from self proteins, there are multiple mechanisms by which T-cells recognizing MHC Class II/peptide complexes are deleted or prevented from activating an immune response.

With the preceding two paragraphs taken as background, it is important to consider how an N-glycosylated protein would be processed in the endosome. Such a protein could be degraded into N-linked oligosaccharide-containing peptides that could bind to MHC Class II molecules. According to an insight of the invention, the endosome also contains an endoglycosidase that sometimes removes the oligosaccharide from asparagine, and in doing so, converts the asparagine into aspartic acid. Thus, self protein sequences that contain asparagine-linked oligosaccharides may be presented by MHC Class II as peptides containing the asparagine linked to an oligosaccharide, or as corresponding peptides containing aspartic acid instead of asparagine.

As part of the invention, it is also recognized that this strategy for reducing the immunogenicity of mammalian proteins that are expressed in bacteria may be applied in a general manner. Specifically, the substitution of aspartic acid for asparagine at a site of N-linked glycosylation generally has the effect of reducing the immunogenicity of a mammalian protein that is expressed in a prokaryote.

The invention contains additional mutations that reduce the immunogenicity of IL-7 and IL-7-containing fusion proteins when expressed in either bacterial or mammalian cells. These mutations include those listed in Table 2 below. An IL-7 or IL-7 containing fusion protein may comprise one or more of these mutations. For example, in one embodiment, IL-7 is modified to incorporate one or more of L24D, M54A, F57K, A60S, R61E, M147K, and T149S, with K150, E151 and H152 being deleted. In another embodiment, IL-7 is modified to incorporate one or more of D76N, L77D, T87Q, I88T, V96G, L 119S, M147K, and T149S, with K150, E151 and H152 being deleted. In a further embodiment, IL-7 can be modified to incorporate one or more of L24D, 130T, F39P, M54A, F57K, A60S, R61E, M68D, N69D, L77T87Q, I88T, V96G, L119S, L128A, M147K, and T149S, with K150, E151 and H152 being deleted.

In another embodiment, an IL-7 molecule or an IL-7 containing fusion protein may include mutations to one or more of residues 39, 57, 77 and/or 128 of IL-7. For example, IL-7 in one embodiment, includes a mutation at residue 39. In another embodiment, IL-7 includes a mutation at residue 57. In a further embodiment, IL-7 includes mutations at both residues 39 and 57. In yet another embodiment, IL-7 includes mutations at residues 39, 57 and 128, while in another embodiment, IL-7 includes mutations at residues 39, 57 and 77. In yet another embodiment, IL-7 includes mutations at residues 39, 57, 77 and 128. In a further embodiment, the phenylalanine residue at position 39 is replaced by a proline residue (F39P). In another embodiment, the phenylalanine residue at 57 is replaced by an asparagines residue (F57N). In another embodiment, the leucine residue at position 77 is replaced by aspartic acid (L77D). In yet another embodiment, the leucine residue at position 128 is replaced by serine (L128S).

TABLE 2

| Initial position in mature human IL-7 | Substitution |
|---|---|
| Gln22 | Asp |
| Leu24 | Asp |
| Ile30 | Thr |
| Phe39 | Pro |
| Met54 | Ala |
| Phe57 | Lys, Asn |
| Arg58 | Asp |
| Ala60 | Ser |
| Arg61 | Glu |
| Leu63 | Ala, Val, Pro |
| Lys68 | Asp |
| Met69 | Asp |
| Leu77 | Asp |
| Ile88 | Thr |
| Val96 | Gly |
| Leu104 | Ser, Val |
| Leu128 | Ala, Val, Pro, Ser |
| Met147 | Lys |
| Thr149 | Ser |
| Lys150 | Stop |

Verification of the Reduced Immunogenicity of the Proteins of the Invention

To check that a mutation of the invention has indeed resulted in reduced immunogenicity, standard experimental tests, which are well known in the art, may be employed. For example, a T-cell stimulation assay may be used (e.g. Jones et al., (2004), *J. Interferon Cytokine Res.,* 24:560). In such an assay, human peripheral blood mononuclear cells (PBMCs) are obtained and cultured according to standard conditions. After an optional pre-stimulation, a peptide corresponding to a potential MHC Class II epitope is added to the culture of PBMCs; the PBMCs are further incubated, and at a later time tritiated thymidine is added. The peptide may be a minimal 9-mer, or may have about 10 to 15 or more amino acids. After further incubation of the cells, incorporation of tritiated thymidine into DNA is then measured by standard techniques.

The T-cell stimulation assay is thought to work by the following mechanisms. First, if a peptide is used as a stimulator, the peptide must first bind to an MHC Class II molecule present on a cell among the PBMCs. Second, the MHC Class II/peptide complex must interact productively with a T-cell receptor on a CD4+ T-cell. If the test peptide is unable to bind sufficiently tightly to an MHC Class II molecule, no signal will result. If the peptide is able to bind an MHC Class II molecule and there are T-cells expressing an appropriately rearranged T-cell receptor capable of recognizing a particular MHC Class II/peptide complex, a signal should result. However, if such T-cells have been deleted as a result of a negative selection process, no signal will result. These mechanisms are considered relevant to the immunogenicity of a protein sequence, as inferred from the stimulation or lack of stimulation by a given peptide.

If recognizing T-cells are present in very low numbers in the PBMC population for stochastic reasons relating to failure of an appropriate T-cell receptor to take place or proliferation of other, unrelated T-cells followed by homeostasis of the T-cell population, there may also be no signal even though a signal is expected. Thus, false negative results may occur. Based on these considerations, it is important to use a large number of different sources of PBMCs and to test these samples independently. It is also generally useful to test PBMCs from an ethnically diverse set of humans, and to determine the MHC Class II alleles present in each PBMC population.

The standard T-cell assay has the disadvantage that the tritium incorporation signal is often only two-fold greater than the background incorporation. The proteins and peptides of the invention may also be tested in a modified T-cell assay in which, for example, purified CD4+ T-cells and purified dendritic cells are co-cultured in the presence of the test peptide, followed by exposure to tritiated thymidine and then assayed for tritiated thymidine incorporation. This second assay has the advantage that tritiated thymidine incorporation into irrelevant cells, such as CD8+ T-cells, is essentially eliminated and background is thus reduced.

A third assay involves the testing of a candidate protein with reduced immunogenicity in an animal such as a primate. Such an assay would generally involve the testing of an entire IL-7 protein or IL-7-containing fusion protein in which the IL-7 moiety had been designed by testing individual component peptides for potential immunogenicity in a cell-based assay such as one described above. Once such a candidate IL-7-containing protein is designed and expressed, the protein is tested for immunogenicity by injection into an animal.

Injection of the modified IL-7-containing protein is generally performed in the same manner as the anticipated route of delivery during therapeutic use in humans. For example, intradermal, subcutaneous, intramuscular, intraperitoneal injection or intravenous infusion may be used. If more than one administration is used, the administrations may be by different routes.

For immunogenicity testing purposes, it may be useful to coadminister an adjuvant to increase the signal and minimize the number of animals that need to be used. If an adjuvant is used, it is possible to use an adjuvant lacking a protein component, such as non-coding DNA with unmethylated CpG dinucleotides, bacterial lipid A, N-formyl methionine, or other bacterial non-protein components. Without wishing to be bound by theory, the rationale for avoiding protein-containing adjuvants is that other proteins may provide T-cell epitopes that will ultimately contribute to an antibody response against the candidate protein.

After one or more administrations of the candidate IL-7-containing protein, the presence of anti-IL-7 antibodies is tested according to standard techniques, such as the ELISA method. It is found that the altered IL-7-containing molecules of the invention induce antibody formation less frequently, and to a lesser extent, than corresponding molecules containing normal human IL-7.

Many of the proteins of the invention alter surface residues of IL-7. It is contemplated that the proteins of the invention, while being less immunogenic than corresponding proteins containing human IL-7, may still occasionally induce formation of antibodies. Because the B-cell epitopes of the proteins of the invention are generally different from those of unmodified IL-7, antibodies to the proteins of the invention will generally not cross-react with endogenous IL-7, and formation of antibodies to the proteins of the invention will have no long-term consequences for the health of the patient.

Fc-IL-7 Fusion Proteins

A key aspect of the invention is that IL-7 modified according to the invention may be fused to a carrier protein to create a fusion protein. In one embodiment, the carrier protein is disposed towards the N-terminus of the fusion protein and the IL-7 is disposed towards the C-terminus. In another embodiment, the IL-7 is disposed towards the N-terminus of the fusion protein and the carrier protein is disposed towards the C-terminus.

The carrier protein can be any polypeptide covalently fused to the IL-7 protein. In one embodiment, the carrier protein is albumin, for example, human serum albumin. The albumin moiety may be fused to the C-terminal or N-terminal end of the IL-7 moiety. In another embodiment, the carrier protein is an immunoglobulin (Ig) moiety, such as an Ig heavy chain. The Ig chain may be derived from IgA, IgD, IgE, IgG, or IgM. According to the invention, the Ig moiety may be an intact antibody and may direct the IL-7 fusion protein to specific target sites in the body. Fusion proteins making use of antibody targeting are known to those in the art.

In one embodiment, the Ig moiety comprises an Fc region. As used herein, "Fc portion" encompasses domains derived from the constant region of an immunoglobulin, such as a human immunoglobulin, including a fragment, analog, variant, mutant or derivative of the constant region. Suitable immunoglobulins include IgG1, IgG2, IgG3, IgG4, and other classes. The constant region of an immunoglobulin is defined as a naturally-occurring or synthetically-produced polypeptide homologous to the immunoglobulin C-terminal region, and can include a hinge, a CH2 domain, a CH3 domain, or a CH4 domain, separately or in any combination. In the present invention, the Fc portion typically includes at least a CH2 domain. For example, the Fc portion can include hinge-CH2-CH3. Alternatively, the Fc portion can include all or a portion of the hinge region, the CH2 domain and/or the CH3 domain. Methods for making Fc-IL-7 fusion proteins are disclosed in U.S. Provisional Patent Application No. 60/533,406.

The constant region of an immunoglobulin is responsible for many important antibody functions including Fc receptor (FcR) binding and complement fixation. There are five major classes of heavy chain constant region, classified as IgA, IgG, IgD, IgE, and IgM. For example, IgG is separated into four γ subclasses: γ 1, γ 2, γ 3, and γ 4, also known as IgG1, IgG2, IgG3, and IgG4, respectively.

IgG molecules interact with multiple classes of cellular receptors, including three classes of Fcγ receptors (Fc γ R) specific for the IgG class of antibody, namely FcγRI, FcγRII, and FcγRIII. The important sequences for the binding of IgG to the FcγR receptors have been reported to be located in the CH2 and CH3 domains. The serum half-life of an antibody is influenced by the ability of that antibody to bind to an Fc receptor (FcR). Similarly, the serum half-life of immunoglobulin fusion proteins is also influenced by the ability to bind to such receptors (Gillies et al., (1999) *Cancer Res.* 59:2159-66). Compared to those of IgG1, CH2 and CH3 domains of IgG2 and IgG4 have biochemically undetectable or reduced binding affinity to Fc receptors. It has been reported that immunoglobulin fusion proteins containing CH2 and CH3 domains of IgG2 or IgG4 had longer serum half-lives compared to the corresponding fusion proteins containing CH2 and CH3 domains of IgG1 (U.S. Pat. No. 5,541,087; Lo et al., (1998) *Protein Engineering,* 11:495-500). Accordingly, in certain embodiments of the invention, CH2 and CH3 domains are derived from an antibody isotype with reduced receptor binding affinity and effector functions, such as, for example, IgG2 or IgG4.

The hinge region is normally located C-terminal to the CH1 domain of the heavy chain constant region. In the IgG isotypes, disulfide bonds typically occur within this hinge region, permitting the final tetrameric molecule to form. This region is dominated by prolines, serines and threonines. When included in the present invention, the hinge region is typically at least homologous to the naturally-occurring immunoglobulin region that includes the cysteine residues to form disulfide bonds linking the two Fc moieties. Representative sequences of hinge regions for human and mouse immunoglobulins are known in the art and can be found in Borrebaeck, C. A. K., ed., (1992) *Antibody Engineering, A Practical Guide,* W. H. Freeman and Co. Suitable hinge regions for the present invention can be derived from IgG1, IgG2, IgG3, IgG4, and other immunoglobulin classes.

The IgG1 hinge region has three cysteines, two of which are involved in disulfide bonds between the two heavy chains of the immunoglobulin. These same cysteines permit efficient and consistent disulfide bonding formation of an Fc portion. Therefore, a hinge region of the present invention in one embodiment is derived from IgG1, such as human IgG1. When the IgG1 hinge is used, the first cysteine can be mutated to another amino acid, such as serine.

The IgG2 isotype hinge region has four disulfide bonds that tend to promote oligomerization and possibly incorrect disulfide bonding during secretion in recombinant systems. A suitable hinge region can be derived from an IgG2 hinge. In one embodiment, the first two cysteines of the IgG2 hinge are mutated to another amino acid.

The hinge region of IgG4 is known to form interchain disulfide bonds inefficiently. However, a suitable hinge region for the present invention can be derived from the IgG4 hinge region, and can contain a mutation that enhances correct formation of disulfide bonds between heavy chain-derived moieties (Angal et al., (1993) *Mol. Immunol.,* 30:105-8).

In accordance with the present invention, the Fc portion can contain CH2 and/or CH3 and/or CH4 domains and a hinge region that are derived from different antibody isotypes, i.e., a hybrid Fc portion. For example, in one embodiment, the Fc portion contains CH2 and/or CH3 domains derived from IgG2 or IgG4 and a mutant hinge region derived from IgG1. Alternatively, a mutant hinge region from another IgG subclass is used in a hybrid Fc portion. For example, a mutant form of the IgG4 hinge that allows efficient disulfide bonding between the two heavy chains can be used. A mutant hinge can also be derived from an IgG2 hinge in which the first two cysteines are each mutated to another amino acid. Such hybrid Fc portions facilitate high-level expression and improve the correct assembly of the Fc-IL-7 fusion proteins. Assembly of such hybrid Fc portions is known in the art and has been described in U.S. Published Patent Application No. 2003-0044423.

In some embodiments, the Fc portion contains amino acid modifications that generally extend the serum half-life of an Fc fusion protein. Such amino acid modifications include mutations substantially decreasing or eliminating Fc receptor binding or complement fixing activity. For example, the glycosylation site within the Fc portion of an immunoglobulin heavy chain can be removed. In IgG1, the glycosylation site is Asn297 within the amino acid sequence Gln-Tyr-Asn-Ser (SEQ ID NO:54). In other immunoglobulin isotypes, the glycosylation site corresponds to Asn297 of IgG1. For example, in IgG2 and IgG4, the glycosylation site is the asparagine within the amino acid sequence Gln-Phe-Asn-Ser (SEQ ID NO:55). Accordingly, a mutation of Asn297 of IgG1 removes the glycosylation site in an Fc portion derived from IgG1. In one embodiment, Asn297 is replaced with Gln. In other embodiments, the tyrosine within the amino acid sequence Gln-Tyr-Asn-Ser (SEQ ID NO:54) is further mutated to eliminate a potential non-self T-cell epitope resulting from asparagine mutation. For example, the amino acid sequence Gln-Tyr-Asn-Ser (SEQ ID NO:54) within an IgG1 heavy chain can be replaced with a Gln-Ala-Gln-Ser (SEQ ID NO:56) amino acid sequence.

Similarly, in IgG2 or IgG4, a mutation of asparagine within the amino acid sequence Gln-Phe-Asn-Ser (SEQ ID NO:55) removes the glycosylation site in an Fc portion derived from IgG2 or IgG4 heavy chain. In one embodiment, the asparagine is replaced with a glutamine. In other embodiments, the phenylalanine within the amino acid sequence Gln-Phe-Asn-Ser (SEQ ID NO:55) is further mutated to eliminate a potential non-self T-cell epitope resulting from asparagine mutation. For example, the amino acid sequence Gln-Phe-Asn-Ser (SEQ ID NO:55) within an IgG2 or IgG4 heavy chain can be replaced with a Gln-Ala-Gln-Ser (SEQ ID NO:56) amino acid sequence. Other mutations that are useful in reducing Fc receptor binding are disclosed in U.S. patent application Ser. No. 09/256,156.

It has also been observed that alteration of amino acids near the junction of the Fc portion and the non-Fc portion can dramatically increase the serum half life of the Fc fusion protein. (U.S. Published Patent Application No. 2002-0147311). Accordingly, the junction region of an Fc-IL-7 or IL-7-Fc fusion protein of the present invention can contain alterations that, relative to the naturally-occurring sequences of an immunoglobulin heavy chain and IL-7, lie within about 10 amino acids of the junction point. These amino acid changes can cause an increase in hydrophobicity by, for example, changing the C-terminal lysine of the Fc portion to a hydrophobic amino acid such as alanine or leucine. (See e.g. SEQ ID NO: 16). In yet another embodiment of the invention, the C-terminal lysine and preceding glycine of the Fc portion are deleted. (See e.g. SEQ ID NO: 18).

In other embodiments, the Fc portion contains amino acid alterations of the Leu-Ser-Leu-Ser segment near the C-terminus of the Fc portion of an immunoglobulin heavy chain. The amino acid substitutions of the Leu-Ser-Leu-Ser (SEQ ID NO:57) segment eliminate potential junctional T-cell epitopes. In one embodiment, the Leu-Ser-Leu-Ser (SEQ ID NO:57) amino acid sequence near the C-terminus of the Fc portion is replaced with an Ala-Thr-Ala-Thr (SEQ ID NO:58) amino acid sequence. In other embodiments, the amino acids within the Leu-Ser-Leu-Ser (SEQ ID NO:57) segment are replaced with other amino acids such as glycine or proline. Detailed methods of generating amino acid substitutions of the Leu-Ser-Leu-Ser (SEQ ID NO:57) segment near the C-terminus of an IgG1, IgG2, IgG3, IgG4, or other immunoglobulin class molecules, as well as other exemplary modifications for altering junctional T-cell epitopes, have been described in U.S. Published Patent Application No. 2003-0166877.

In one embodiment, a spacer or linker peptide is inserted between the carrier protein and the IL-7 protein. The spacer or linker peptide can be non-charged or non-polar or hydrophobic. The length of a spacer or linker peptide is between 1 and about 100 amino acids, or between 1 and about 50 amino acids, or between 1 and about 25 amino acids, or between 1 and about 15 amino acids. In one embodiment, the spacer contains a sequence $(G_4S)_n$, where n is less than 10. In another embodiment, the linker sequence is GGGGSGGGG (SEQ ID NO:17). In yet another embodiment, the spacer contains a motif that is recognized as an N-linked glycosylation site. In another embodiment of the invention, the carrier protein and the IL-7 fusion protein are joined via a spacer or linker peptide. In an alternative embodiment of the invention, the carrier protein and IL-7 fusion protein are separated by a synthetic spacer, for example a PNA spacer. The spacer can be non-charged, or non-polar or hydrophobic.

Production of IL-7 Fusion Proteins

Fusion proteins containing IL-7 modified according to the teachings of the invention can be synthesized by the non-limiting methods described herein. Assays useful for testing pharmacokinetic activities of fusion proteins containing IL-7 modified according to the invention in in vivo animal models are also described herein.

The IL-7 fusion proteins of the invention can be produced using recombinant expression vectors known in the art. The term "expression vector" refers to a replicable DNA construct used to express DNA which encodes the desired IL-7 fusion protein and which includes a transcriptional unit comprising an assembly of (1) genetic element(s) having a regulatory role in gene expression, for example, promoters, operators, or enhancers, operatively linked to (2) a DNA sequence encoding the desired IL-7 fusion protein which is transcribed into mRNA and translated into protein, and (3) appropriate transcription and translation initiation and termination sequences. The choice of promoter and other regulatory elements generally varies according to the intended host cell.

The nucleic acid encoding the IL-7 fusion protein is transfected into a host cell using recombinant DNA techniques. In the context of the present invention, the foreign DNA includes a sequence encoding the inventive proteins. Suitable host cells include prokaryotic, yeast or higher eukaryotic cells. In one embodiment, the host is a prokaryotic organism.

The recombinant IL-7 fusion proteins can be expressed in yeast hosts, such as from *Saccharomyces* species, such as *S. cerevisiae*. Yeast of other genera such as *Pichia* or *Kluyveromyces* may also be employed. Yeast vectors will generally contain an origin of replication from a yeast plasmid or an autonomously replicating sequence (ARS), a promoter, DNA encoding the IL-7 fusion protein, sequences for polyadenylation and transcription termination and a selection gene. Suitable promoter sequences in yeast vectors include the promoters for metallothionein, 3-phosphoglycerate kinase or other glycolytic enzymes, such as enolase, glyceraldehyde-3-phosphate dehydrogenase, hexokinase, pyruvate decarboxylase, phosphofructokinase, glucose-4-phosphate isomerase, 3-phosphoglycerate mutase, pyruvate kinase, triosephosphate isomerase, phosphoglucose isomerase and glucokinase.

Various mammalian or insect cell culture systems can be employed to express recombinant protein. Baculovirus systems for production of proteins in insect cells are well known in the art. Examples of suitable mammalian host cell lines include NS/0 cells, L cells, C127, 3T3, Chinese hamster ovary (CHO), HeLa, and BHK cell lines. Additional suitable mammalian host cells include CV-1 cells (ATCC CCL70) and COS-7 cells both derived from monkey kidney. Another suitable monkey kidney cell line, CV-1/EBNA, was derived by transfection of the CV-1 cell line with a gene encoding Epstein-Barr virus nuclear antigen-1 (EBNA-1) and with a vector containing CMV regulatory sequences (McMahan et al., (1991), *EMBO J.,* 10:2821). The EBNA-1 gene allows for episomal replication of expression vectors, such as HAV-EO or pDC406, that contain the EBV origin of replication.

Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences. Commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence.

When secretion of the IL-7 fusion protein from the host cell is desired, the expression vector may comprise DNA encoding a signal or leader peptide. In the present invention the native signal sequence of IL-7 can be used, or alternatively, a heterologous signal sequence may be added, such as the signal sequence from interleukin-4.

The present invention also provides a process for preparing the recombinant proteins of the present invention including culturing a host cell transformed with an expression vector comprising a DNA sequence that encodes the IL-7 fusion protein under conditions that promote expression. The desired protein is then purified from culture media or cell extracts. For example, supernatants from expression systems that secrete recombinant protein into the culture medium can be first concentrated using a commercially available protein concentration filter, for example, an Amicon or Millipore Pellicon ultrafiltration unit. Following the concentration step, the concentrate can be applied to a suitable purification matrix, as known in the art.

An "isolated" or "purified" IL-7 fusion protein or biologically active portion thereof is substantially free of cellular material or other contaminating proteins from the cell or tissue source from which the IL-7 fusion protein is derived, or substantially free from chemical precursors or other chemicals when chemically synthesized. The language "substantially free of cellular material" includes preparations of IL-7 fusion protein in which the protein is separated from cellular components of the cells from which it is isolated or recombinantly produced. In one embodiment, the language "substantially free of cellular material" includes preparations of IL-7 fusion protein having less than about 30% (by dry weight) of non-IL-7 fusion protein (also referred to herein as a "contaminating protein"), less than about 20% of non-IL-7 fusion protein, less than about 10% of non-IL-7 fusion protein, or less than about 5% non-IL-7 fusion protein. When the IL-7 fusion protein or biologically active portion thereof is purified from a recombinant source, it is, in one embodiment, substantially free of culture medium, i.e., culture medium represents less than about 20%, less than about 10%, or less than about 5% of the volume of the protein preparation.

The term "substantially pure Ig-IL-7 fusion protein" or "substantially pure IL-7 fusion protein" refers to a preparation in which the IL-7 comprising fusion protein constitutes at least 60%, 70%, 80%, 90%, 95% or 99% of the proteins in the preparation.

Methods of Treatment Using IL-7 Proteins

The IL-7 proteins, including fusion proteins, of the invention are useful in treating immune deficiencies and in accelerating the natural reconstitution of the immune system that occurs, for example, after diseases or treatments that are immunosuppressive in nature. For example, IL-7 proteins can be used to treat viral infections, immune disorders, and to enhance the growth (including proliferation) of specific cell types. Moreover, the IL-7 proteins can be in the treatment of cancers such as bladder cancer, lung cancer, brain cancer, breast cancer, skin cancer, and prostate cancer. In one example, it is useful to treat patients who have undergone one or more cycles of chemotherapy with IL-7 proteins as described above to help their immune cells replenish. Alternatively, it is also useful to administer the IL-7 proteins described above to patients with HIV, the elderly, patients receiving a transplant or other patients with suppressed immune system function.

Administration

Both the IL-7 and IL-7 fusion proteins of the invention can be incorporated into a pharmaceutical composition suitable for administration. Such compositions typically comprise IL-7 or an IL-7 fusion protein and a pharmaceutically-acceptable carrier. As used herein the language "pharmaceutically-acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Medicaments that contain the IL-7 proteins of the invention can have a concentration of 0.01 to 100% (w/w), though the amount varies according to the dosage form of the medicaments.

Administration dose depends on the body weight of the patients, the seriousness of the disease, and the doctor's opinion. However, it is generally advisable to administer between about 0.01 to about 10 mg/kg body weight a day, about 0.02 to about 2 mg/kg/day in case of injection, or about 0.5 mg/kg/day. The dose can be administered once or several times daily according to the seriousness of the disease and the doctor's opinion.

Compositions of the invention are useful when co-administered with one or more other therapeutic agents, for example, a molecule also known to be useful to replenish blood cells. For example, the molecule may be erythropoietin which is known to be used to replenish red blood cells, G-CSF which is used to replenish neutrophils or GM-CSF which is used to replenish granulocytes and macrophages.

Aspects of invention are further illustrated by the following examples.

EXAMPLES

Example 1

Identification of T-cell Epitopes by Computational Methods

According to the invention, epitopes of IL-7 can be modified using methods for introducing mutations into proteins to modulate their interaction with the immune system. These methods are similar to those disclosed in U.S. Published Patent Application No. 2003-0166877. According to the invention, known methods in the art that can be adapted according to the invention include those described in the prior art (WO 92/10755 and WO 96/40792 (Novo Nordisk), EP 0519 596 (Merck & Co.), EP 0699 755(Centro de Immunologia Moelcular), WO 98/52976 and WO 98/59244 (Biovation Ltd.) or related methods.

Advantageous mutant proteins, however, can be obtained if the identification of said epitopes is realized by the following method which is described herewith in detail and applied to IL-7. There are a number of factors that play important roles in determining the total structure of a protein, polypeptide or immunoglobulin. First, the peptide bond, i.e., that bond which joins the amino acids in the chain together, is a covalent bond. This bond is planar in structure, essentially a substituted amide. An "amide" is any of a group of organic compounds containing the grouping —CONH—.

The planar peptide bond linking Cα of adjacent amino acids may be represented as

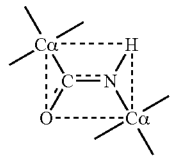

depicted below:

Because the O═C and the C—N atoms lie in a relatively rigid plane, free rotation does not occur about these axes. Hence, a plane schematically depicted by the interrupted line is sometimes referred to as an "amide" or "peptide plane" plane wherein lie the oxygen (O), carbon (C), nitrogen (N), and hydrogen (H) atoms of the peptide backbone. At opposite corners of this amide plane are located the Cα atoms. Since there is substantially no rotation about the O═C and C—N atoms in the peptide or amide plane, a polypeptide chain thus comprises a series of planar peptide linkages joining the Cα atoms.

A second factor that plays an important role in defining the total structure or conformation of a polypeptide or protein is the angle of rotation of each amide plane about the common Cα linkage. The terms "angle of rotation" and "torsion angle" are hereinafter regarded as equivalent terms. Assuming that the O, C, N, and H atoms remain in the amide plane (which is usually a valid assumption, although there may be some slight deviations from planarity of these atoms for some conformations), these angles of rotation define the N and R polypeptide's backbone conformation, i.e., the structure as it exists between adjacent residues. These two angles are known as $\phi$ and $\psi$. A set of the angles $\phi_i$, $\psi_i$, where the subscript i represents a particular residue of a polypeptide chain, thus effectively defines the polypeptide secondary structure. The conventions used in defining the $\phi$, $\psi$ angles, i.e., the reference points at which the amide planes form a zero degree angle, and the definition of which angle is $\phi$, and which angle is $\psi$, for a given polypeptide, are defined in the literature. (See, e.g, Ramachandran et al., (1968), *Adv. Prot. Chem.* 23:283-437, at pages 285-94).

The method can be applied to any protein, and is based in part upon the discovery that in humans the primary Pocket 1 anchor position of MHC Class II molecule binding grooves has a well designed specificity for particular amino acid side chains. The specificity of this pocket is determined by the identity of the amino acid at position 86 of the beta chain of the MHC Class II molecule. This site is located at the bottom of Pocket 1 and determines the size of the side chain that can be accommodated by this pocket. Marshall, *J. Immunol., (*1994), 152:4946-4956. If this residue is a glycine, then all hydrophobic aliphatic and aromatic amino acids (hydrophobic aliphatics being: valine, leucine, isoleucine, methionine and aromatics being: phenylalanine, tyrosine and tryptophan) can be accommodated in the pocket, with a preference being for the aromatic side chains. If this pocket residue is a valine, then the side chain of this amino acid protrudes into the pocket and restricts the size of peptide side chains that can be accommodated such that only hydrophobic aliphatic side chains can be accommodated. Therefore, in an amino acid residue sequence, wherever an amino acid with a hydrophobic aliphatic or aromatic side chain is found, there is the potential for a MHC Class II restricted T-cell epitope. If the side-chain is hydrophobic aliphatic, however, it is approximately twice as likely to be associated with a T-cell epitope than an aromatic side chain (assuming an approximately even distribution of Pocket 1 types throughout the global population).

An exemplary computational method profiles the likelihood of peptide regions of IL-7 to contain T-cell epitopes as follows: (1) The primary sequence of a peptide segment of predetermined length is scanned, and all hydrophobic aliphatic and aromatic side chains present are identified. (2) The hydrophobic aliphatic side chains are assigned a value greater than that for the aromatic side chains; preferably about twice the value assigned to the aromatic side chains, e.g., a value of 2 for a hydrophobic aliphatic side chain and a value of 1 for an aromatic side chain. (3) The values determined to be present are summed for each overlapping amino acid residue segment (window) of predetermined uniform length within the peptide, and the total value for a particular segment (window) is assigned to a single amino acid residue at an intermediate position of the segment (window), preferably to a residue at about the midpoint of the sampled segment (window). This procedure is repeated for each sampled overlapping amino acid residue segment (window). Thus, each amino acid residue of the peptide is assigned a value that relates to the likelihood of a T-cell epitope being present in that particular segment (window). (4) The values calculated and assigned as described in Step 3, above, can be plotted against the amino acid coordinates of the entire amino acid residue sequence being assessed. (5) All portions of the sequence which have a score of a predetermined value, e.g., a value of 1, are deemed likely to contain a T-cell epitope and can be modified, if desired.

This particular aspect of the present invention provides a general method by which T-cell epitopes of IL-7 can be described. Modifications to the peptide in these regions have the potential to modify the MHC Class II binding characteristics.

According to another aspect of the present invention, T-cell epitopes can be predicted with greater accuracy by the use of a more sophisticated computational method which takes into account the interactions of peptides with models of MHC Class II alleles.

The computational prediction of T-cell epitopes present within a peptide according to this particular aspect contemplates the construction of models of at least 42 MHC Class II alleles based upon the structures of all known MHC Class II molecules and a method for the use of these models in the computational identification of T-cell epitopes, the construction of libraries of peptide backbones for each model in order to allow for the known variability in relative peptide backbone alpha carbon (C$\alpha$) positions, the construction of libraries of amino-acid side chain conformations for each backbone dock with each model for each of the 20 amino-acid alternatives at positions critical for the interaction between peptide and MHC Class II molecule, and the use of these libraries of backbones and side-chain conformations in conjunction with a scoring function to select the optimum backbone and side-chain conformation for a particular peptide docked with a particular MHC Class II molecule and the derivation of a binding score from this interaction.

Models of MHC Class II molecules can be derived via homology modeling from a number of similar structures found in the Brookhaven Protein Data Bank ("PDB"). These may be made by the use of semi-automatic homology modeling software (Modeller et al., (1993), J. Mol. Biol., 234: 779-815) which incorporates a simulated annealing function, in conjunction with the CHARMm force-field for energy minimization (available from Molecular Simulations Inc., San Diego, Calif.). Alternative modeling methods can be utilized as well.

Other computational methods which use libraries of experimentally derived binding data of each amino-acid alternative at each position in the binding groove for a small set of MHC Class II molecules (Marshall et al., (1995), Biomed. Pept. Proteins Nucleic Acids, 1(3): 157-162) are known, as are yet other computational methods which use similar experimental binding data in order to define the binding characteristics of particular types of binding pockets within the groove, again using a relatively small subset of MHC Class II molecules, and then 'mixing and matching' pocket types from this pocket library to artificially create further 'virtual' MHC Class II molecules (Sturniolo et al., (1999), Nat. Biotech, 17(6): 555-561. Both methods suffer the major disadvantage that, due to the complexity of the assays and the need to synthesize large numbers of peptide variants, only a small number of MHC Class II molecules can be experimentally scanned. Therefore the first method can only make predictions for a small number of MHC Class II molecules. The second method also makes the assumption that a pocket lined with similar amino-acids in one molecule will have the same binding characteristics when in the context of a different Class II allele and suffers further disadvantages in that only those MHC Class II molecules can be 'virtually' created which contain pockets contained within the pocket library. Using the modeling approach described herein, the structure of any number and type of MHC Class II molecules can be deduced, therefore alleles can be specifically selected to be representative of the global population. In addition, the number of MHC Class II molecules scanned can be increased by making further models further than having to generate additional data via complex experimentation.

The use of a backbone library allows for variation in the positions of the Cα atoms of the various peptides being scanned when docked with particular MHC Class II molecules. This is again in contrast to the alternative computational methods described above which rely on the use of simplified peptide backbones for scanning amino-acid binding in particular pockets. These simplified backbones are not likely to be representative of backbone conformations found in 'real' peptides leading to inaccuracies in prediction of peptide binding. The present backbone library is created by superposing the backbones of all peptides bound to MHC Class II molecules found within the Protein Data Bank and noting the root mean square (RMS) deviation between the Cα atoms of each of the eleven amino-acids located within the binding groove. While this library can be derived from a small number of suitable available mouse and human structures (currently 13), in order to allow for the possibility of even greater variability, the RMS figure for each C"-α position is increased by 50%. The average Cα position of each amino-acid is then determined and a sphere drawn around this point whose radius equals the RMS deviation at that position plus 50%. This sphere represents all allowed Cα positions.

Working from the Cα with the least RMS deviation (that of the amino-acid in Pocket 1 as mentioned above, equivalent to Position 2 of the 11 residues in the binding groove), the sphere is three-dimensionally gridded, and each vertex within the grid is then used as a possible location for a Cα of that amino-acid. The subsequent amide plane, corresponding to the peptide bond to the subsequent amino-acid is grafted onto each of these Cαs and the ϕ and ψ angles are rotated step-wise at set intervals in order to position the subsequent Cα. If the subsequent Cα falls within the 'sphere of allowed positions' for this Cα than the orientation of the dipeptide is accepted, whereas if it falls outside the sphere then the dipeptide is rejected. This process is then repeated for each of the subsequent Cα positions, such that the peptide grows from the Pocket 1 Cα 'seed', until all nine subsequent Cαs have been positioned from all possible permutations of the preceding Cαs. The process is then repeated once more for the single Cα preceding pocket 1 to create a library of backbone Cα positions located within the binding groove.

The number of backbones generated is dependent upon several factors: The size of the 'spheres of allowed positions'; the fineness of the gridding of the 'primary sphere' at the Pocket 1 position; the fineness of the step-wise rotation of the ϕ and ψ angles used to position subsequent Cαs. Using this process, a large library of backbones can be created. The larger the backbone library, the more likely it will be that the optimum fit will be found for a particular peptide within the binding groove of an MHC Class II molecule. Inasmuch as all backbones will not be suitable for docking with all the models of MHC Class II molecules due to clashes with amino-acids of the binding domains, for each allele a subset of the library is created comprising backbones which can be accommodated by that allele. The use of the backbone library, in conjunction with the models of MHC Class II molecules creates an exhaustive database consisting of allowed side chain conformations for each amino-acid in each position of the binding groove for each MHC Class II molecule docked with each allowed backbone. This data set is generated using a simple steric overlap function where a MHC Class II molecule is docked with a backbone and an amino-acid side chain is grafted onto the backbone at the desired position. Each of the rotatable bonds of the side chain is rotated step-wise at set intervals and the resultant positions of the atoms dependent upon that bond noted. The interaction of the atom with atoms of side-chains of the binding groove is noted and positions are either accepted or rejected according to the following criteria: the sum total of the overlap of all atoms so far positioned must not exceed a pre-determined value. Thus the stringency of the conformational search is a function of the interval used in the step-wise rotation of the bond and the pre-determined limit for the total overlap. This latter value can be small if it is known that a particular pocket is rigid; however, the stringency can be relaxed if the positions of pocket side-chains are known to be relatively flexible. Thus allowances can be made to imitate variations in flexibility within pockets of the binding groove. This conformational search is then repeated for every amino-acid at every position of each backbone when docked with each of the MHC Class II molecules to create the exhaustive database of side-chain conformations.

A suitable mathematical expression is used to estimate the energy of binding between models of MHC Class II molecules in conjunction with peptide ligand conformations which have to be empirically derived by scanning the large database of backbone/side-chain conformations described above. Thus a protein is scanned for potential T-cell epitopes by subjecting each possible peptide of length varying between 9 and 20 amino-acids (although the length is kept constant for each scan) to the following computations: An MHC Class II molecule is selected together with a peptide backbone allowed for that molecule and the side-chains corresponding to the desired peptide sequence are grafted on. Atom identity and interatomic distance data relating to a particular side-chain at a particular position on the backbone are collected for each allowed conformation of that amino-acid (obtained from the database described above). This is repeated for each side-chain along the backbone and peptide scores derived using a scoring function. The best score for that backbone is retained and the process repeated for each allowed backbone for the selected model. The scores from all allowed backbones are compared and the highest score is deemed to be the peptide score for the desired peptide in that MHC Class II model. This process is then repeated for each model with every possible peptide derived from the protein being scanned, and the scores for peptides versus models are displayed.

In the context of the present invention, each ligand presented for the binding affinity calculation is an amino-acid segment selected from a peptide or protein as discussed above. Thus, the ligand is a selected stretch of amino acids about 9 to 20 amino acids in length derived from a peptide, polypeptide or protein of known sequence. The terms "amino acids" and "residues" are hereinafter regarded as equivalent terms. The ligand, in the form of the consecutive amino acids of the peptide to be examined grafted onto a backbone from the backbone library, is positioned in the binding cleft of an MHC Class II molecule from the MHC Class II molecule model library via the coordinates of the C"-α atoms of the peptide backbone and an allowed conformation for each side-chain is selected from the database of allowed conformations. The relevant atom identities and interatomic distances are also retrieved from this database and used to calculate the peptide binding score. Ligands with a high binding affinity for the MHC Class II binding pocket are flagged as candidates for site-directed mutagenesis. Amino-acid substitutions are made in the flagged ligand (and hence in the protein of interest) which is then retested using the scoring function in order to determine changes which reduce the binding affinity below a predetermined threshold value. These changes can then be incorporated into the protein of interest to remove T-cell epitopes.

Binding between the peptide ligand and the binding groove of MHC Class II molecules involves non-covalent interactions including, but not limited to: hydrogen bonds, electrostatic interactions, hydrophobic (lipophilic) interactions and van der Waal's interactions. These are included in the peptide scoring function as described in detail below. It should be understood that a hydrogen bond is a non-covalent bond which can be formed between polar or charged groups and consists of a hydrogen atom shared by two other atoms. The hydrogen of the hydrogen donor has a positive charge where the hydrogen acceptor has a partial negative charge. For the purposes of peptide/protein interactions, hydrogen bond donors may be either nitrogens with hydrogen attached or hydrogens attached to oxygen or nitrogen. Hydrogen bond acceptor atoms may be oxygens not attached to hydrogen, nitrogens with no hydrogens attached and one or two connections, or sulphurs with only one connection. Certain atoms, such as oxygens attached to hydrogens or imine nitrogens (e.g. C═NH) may be both hydrogen acceptors or donors. Hydrogen bond energies range from 3 to 7 Kcal/mol and are much stronger than van der Waal's bonds, but weaker than covalent bonds. Hydrogen bonds are also highly directional and are at their strongest when the donor atom, hydrogen atom and acceptor atom are co-linear. Electrostatic bonds are formed between oppositely charged ion pairs and the strength of the interaction is inversely proportional to the square of the distance between the atoms according to Coulomb's law. The optimal distance between ion pairs is about 2.8 Å. In protein/peptide interactions, electrostatic bonds may be formed between arginine, histidine or lysine and aspartate or glutamate. The strength of the bond will depend upon the pKa of the ionizing group and the dielectric constant of the medium although they are approximately similar in strength to hydrogen bonds.

Lipophilic interactions are favorable hydrophobic-hydrophobic contacts that occur between the protein and the peptide ligand. Usually, these will occur between hydrophobic amino acid side chains of the peptide buried within the pockets of the binding groove such that they are not exposed to solvent. Exposure of the hydrophobic residues to solvent is highly unfavorable since the surrounding solvent molecules are forced to hydrogen bond with each other forming cage-like clathrate structures. The resultant decrease in entropy is highly unfavorable. Lipophilic atoms may be sulphurs which are neither polar nor hydrogen acceptors and carbon atoms which are not polar.

van der Waal's bonds are non-specific forces found between atoms which are 3-4 Å apart. They are weaker and less specific than hydrogen and electrostatic bonds. The distribution of electronic charge around an atom changes with time and, at any instant, the charge distribution is not symmetric. This transient asymmetry in electronic charge induces a similar asymmetry in neighboring atoms. The resultant attractive forces between atoms reaches a maximum at the van der Waal's contact distance but diminishes very rapidly at about 1 Å to about 2 Å. Conversely, as atoms become separated by less than the contact distance, increasingly strong repulsive forces become dominant as the outer electron clouds of the atoms overlap. Although the attractive forces are relatively weak compared to electrostatic and hydrogen bonds (about 0.6 Kcal/mol), the repulsive forces in particular may be very important in determining whether a peptide ligand may bind successfully to a protein.

In one embodiment, the Böhm scoring function (SCORE1 approach) is used to estimate the binding constant. (Böhm, H. J., (1994), *J. Comput. Aided Mol. Des.,* 8(3):243-256) which is hereby incorporated in its entirety). In another embodiment, the scoring function (SCORE2 approach) is used to estimate the binding affinities as an indicator of a ligand containing a T-cell epitope (Böhm, H. J., (1998), *J. Comput. Aided Mol. Des.,* 12(4):309-323) which is hereby incorporated in its entirety). However, the Böhm scoring functions as described in the above references are used to estimate the binding affinity of a ligand to a protein where it is already known that the ligand successfully binds to the protein and the protein/ligand complex has had its structure solved, the solved structure being present in the Protein Data Bank ("PDB"). Therefore, the scoring function has been developed with the benefit of known positive binding data. In order to allow for discrimination between positive and negative binders, a repulsion term must be added to the equation. In addition, a more satisfactory estimate of binding energy is achieved by computing the lipophilic interactions in a pairwise manner rather than using the area based energy term of the above Böhm functions. Therefore, in one embodiment, the binding energy is estimated using a modified Böhm scoring function. In the modified Böhm scoring function, the binding energy between protein and ligand ($\Delta G_{bind}$) is estimated considering the following parameters: The reduction of binding energy due to the overall loss of translational and rotational entropy of the ligand ($\Delta G_0$); contributions from ideal hydrogen bonds ($\Delta G_{hb}$) where at least one partner is neutral; contributions from unperturbed ionic interactions ($\Delta G_{ionic}$); lipophilic interactions between lipophilic ligand atoms and lipophilic acceptor atoms ($\Delta G_{lipo}$); the loss of binding energy due to the freezing of internal degrees of freedom in the ligand, i.e., the freedom of rotation about each C—C bond is reduced ($\Delta G_{rot}$); the energy of the interaction between the protein and ligand ($E_{VdW}$). Consideration of these terms gives equation 1:

$$(\Delta G_{bind})=(\Delta G_0)+(\Delta G_{hb}\times N_{hb})+(\Delta F_{ionic}\times N_{ionic})+(\Delta F_{lipo}\times N_{lipo})+(\Delta G_{rot}+N_{rot})+(E_{VdW}).$$

where N is the number of qualifying interactions for a specific term and, in one embodiment, $\Delta G_0$, $\Delta G_{hb}$, $\Delta G_{ionic}$, $\Delta G_{lipo}$ and $\Delta G_{rot}$ are constants which are given the values: 5.4, −4.7, −4.7, −0.17, and 1.4, respectively.

The term $N_{hb}$ is calculated according to equation 2:

$$N_{hb}=\Sigma_{h\text{-}bonds}f(\Delta R,\Delta\alpha)\times f(N_{neighb})\times f_{pcs}$$

$f(\Delta R, \Delta\alpha)$ is a penalty function which accounts for large deviations of hydrogen bonds from ideality and is calculated according to equation 3:

$$f(\Delta R, \Delta-\alpha) = f1(\Delta R)\times f2(\Delta\alpha)$$

$$\begin{aligned}\text{where: } f1(\Delta R) &= 1 \text{ if } \Delta R <= TOL\\ &\text{or} = 1-(\Delta R - TOL)/0.4 \text{ if } \Delta R <= 0.4+TOL\\ &\text{or} = 0 \text{ if } \Delta R > 0.4+TOL\end{aligned}$$

$$\begin{aligned}\text{and: } f2(\Delta\alpha) &= 1 \text{ if } \Delta\alpha < 30^\circ\\ &\text{or} = 1-(\Delta\alpha-30)/50 \text{ if } \Delta\alpha <= 80^\circ\\ &\text{or} = 0 \text{ if } \Delta\alpha > 80^\circ\end{aligned}$$

TOL is the tolerated deviation in hydrogen bond length=0.25 Å; ΔR is the deviation of the H—O/N hydrogen bond length from the ideal value=1.9 Å; Δα is the deviation of the hydrogen bond angle $\angle_{N/O-H\,.\,.\,.\,O/N}$ from its idealized value of 180°.

$f(N_{neighb})$ distinguishes between concave and convex parts of a protein surface and therefore assigns greater weight to polar interactions found in pockets rather than those found at the protein surface. This function is calculated according to equation 4 below:

$$f(N_{neighb})=(N_{neighb}/N_{neighb,0})^{\alpha} \text{ where } \alpha=0.5.$$

$N_{neighb}$ is the number of non-hydrogen protein atoms that are closer than 5 Å to any given protein atom.

$N_{neighb,0}$ is a constant=25

$f_{pcs}$ is a function which allows for the polar contact surface area per hydrogen bond and therefore distinguishes between strong and weak hydrogen bonds and its value is determined according to the following criteria:

$$f_{pcs}=\beta \text{ when } A_{polar}/N_{HB}<10\text{ Å}^2$$

$$\text{or } f_{pcs}=1 \text{ when } A_{polar}/N_{HB}>10\text{ Å}^2$$

$A_{polar}$ is the size of the polar protein-ligand contact surface $N_{HB}$ is the number of hydrogen bonds β is a constant whose value=1.2

For the implementation of the modified Böhm scoring function, the contributions from ionic interactions, $\Delta G_{ionic}$, are computed in a similar fashion to those from hydrogen bonds described above since the same geometry dependency is assumed.

The term $N_{lipo}$ is calculated according to equation 5 below:

$$N_{lipo}=\Sigma_{lL}f(r_{lL})$$

$f(r_{lL})$ is calculated for all lipophilic ligand atoms, l, and all lipophilic protein atoms, L, according to the following criteria:

$$f(r_{lL})=1 \text{ when } r_{lL}\leqq R1 f(r_{lL}-R1)/(R2-R1) \text{ when } R2<r_{lL}>R1$$

$$f(r_{lL})=0 \text{ when } r_{lL}\geqq R2$$

where: $R1=r_l^{vdw}+r_L^{vdw}+0.5$ and $R2=R1+3.0$ and $r_l^{vdw}$ is the van der Waal's radius of atom l and $r_L^{vdw}$ is the van der Waal's radius of atom L The term $N_{rot}$ is the number of rotable bonds of the amino acid side chain and is taken to be the number of acyclic $sp^3$-sp3 and sp3-sp2 bonds. Rotations of terminal $-CH_3$ or $-NH_3$ are not taken into account.

The final term, $E_{VdW}$, is calculated according to equation 6 below:

$$E_{VdW}=\epsilon_1\epsilon_2((r_1^{vdw}+r_2^{vdw})^{12}/r^{12}-(r_1^{vdw}+r_2^{vdw})^6/r^6),$$

where:

$\epsilon_1$ and $\epsilon_2$ are constants dependent upon atom identity;

$r_1^{vdw}+r_2^{vdw}$ are the van der Waal's atomic radii; and r is the distance between a pair of atoms.

With regard to equation 6, in one embodiment, the constants $\epsilon_1$ and $\epsilon_2$ are given the atom values: C: 0.245, N: 0.283, O: 0.316, S: 0.316, respectively (i.e. for atoms of Carbon, Nitrogen, Oxygen and Sulfur, respectively). With regards to equations 5 and 6, the van der Waal's radii are given the atom values C: 1.85, N: 1.75, O: 1.60, S: 2.00 Å.

It should be understood that all predetermined values and constants given in the equations above are determined within the constraints of current understandings of protein ligand interactions with particular regard to the type of computation being undertaken herein.

As described above, the scoring function is applied to data extracted from the database of side-chain conformations, atom identities, and interatomic distances. For the purposes of the present description, the number of MHC Class II molecules included in this database is 42 models plus four solved structures. It should be apparent from the above descriptions that the modular nature of the construction of the computational method of the present invention means that new models can simply be added and scanned with the peptide backbone library and side-chain conformational search function to create additional data sets which can be processed by the peptide scoring function as described above. This allows for the repertoire of scanned MHC Class II molecules to easily be increased, or structures and associated data to be replaced if data are available to create more accurate models of the existing alleles.

The present prediction method can be calibrated against a data set comprising a large number of peptides whose affinity for various MHC Class II molecules has previously been experimentally determined. By comparison of calculated versus experimental data, a cut of value can be determined above which it is known that all experimentally determined T-cell epitopes are correctly predicted.

It should be understood that, although the above scoring function is relatively simple compared to some sophisticated methodologies that are available, the calculations are performed extremely rapidly. It should also be understood that the objective is not to calculate the true binding energy per se for each peptide docked in the binding groove of a selected MHC Class II protein. The underlying objective is to obtain comparative binding energy data as an aid to predicting the location of T-cell epitopes based on the primary structure (i.e. amino acid sequence) of a selected protein. A relatively high binding energy or a binding energy above a selected threshold value would suggest the presence of a T-cell epitope in the ligand. The ligand may then be subjected to at least one round of amino-acid substitution and the binding energy recalculated. Due to the rapid nature of the calculations, these manipulations of the peptide sequence can be performed interactively within the program's user interface on cost-effectively available computer hardware. Major investment in computer hardware is thus not required.

It would be apparent to one skilled in the art that other available software could be used for the same purposes. In particular, more sophisticated software which is capable of docking ligands into protein binding-sites may be used in conjunction with energy minimization. Examples of docking software are: DOCK (Kuntz et al., (1982), *J. Mol. Biol.,* 161:269-288), LUDI (Böhm, H. J., (1994), *J. Comput Aided Mol. Des.,* 8:623-632) and FLEXX (Rarey et al., (1995), *ISMB,* 3:300-308). Examples of molecular modeling and manipulation software include: AMBER (Tripos) and CHARMm (Molecular Simulations Inc.). The use of these computational methods would severely limit the throughput of the method of this invention due to the lengths of processing time required to make the necessary calculations. However, it is feasible that such methods could be used as a 'secondary screen' to obtain more accurate calculations of binding energy for peptides which are found to be 'positive binders' via the method of the present invention. The limitation of processing time for sophisticated molecular mechanic or molecular dynamic calculations is one which is defined both by the design of the software which makes these calculations and the current technology limitations of computer hardware. It may be anticipated that, in the future, with the writing of more efficient code and the continuing increases in speed of computer processors, it may become feasible to make such calculations within a more manageable time-frame. Further information on energy functions applied to macromolecules and consideration of the various interactions that take place within a folded protein structure can be found in: Brooks et al., (1983), *J. Comput. Chem.,* 4:187-217 and further information concerning general protein-ligand interactions can be found in: Dauber-Osguthorpe et al., (1988),

*Proteins,* 4(1):31-47. Useful background information can also be found, for example, in Fasman, G. D., ed., *Prediction of Protein Structure and the Principles of Protein Conformation,* Plenum Press, New York, ISBN: 0-306 4313-9.

Example 2

In Vitro Analysis of IL-7 Derived Peptides as Potential CD4+ T Helper Cell Epitopes by Unfractionated PBMC Cultures Based on in silico predictions that sequences surrounding N-linked glycosylation sites of the IL-7 protein are immunogenic, peptides encompassing these regions, spanning for example Leu63 to Ser71 (LRQFLKMNS (SEQ ID NO:48)) or Ile88 to Val96 (ILLNCTGQV (SEQ ID NO:52)) in mature human IL-7 protein, are analyzed for their immunogenicity, which is measured by their ability to induce T-cell proliferation in vitro. In essence, PBMCs isolated from human blood are incubated with individual overlapping 15-mer peptides, and proliferative responses are measured by $^3$H-thymidine incorporation. In principle, T-cells within the mixture of PBMCs will only proliferate if they recognize individual peptide-MHC complexes on autologous APCs (antigen presenting cells), and thus proliferation is an indication of peptide immunogenicity.

For example, 15-mer peptides that are staggered by three amino acids and span the region from, for example, Met54 to Leu80 in human IL-7 are synthesized (Pepscan Systems, Netherlands), resuspended in DMSO (Sigma Chemical, St. Louis, Mo., U.S.A.), and used at a final concentration of 5 μM in 0.5% DMSO in culture media.

PBMCs are isolated from peripheral blood from healthy donors by Ficoll-Hypaque gradient centrifugation, and are stored frozen in liquid nitrogen. In addition, each PBMC sample is HLA typed, using a SSP PCR typing kit (Bio-Synthesis, Lewisville, Tex.) on DNA isolated with a QiaAmp Tissue Kit (Qiagen, Valencia, Calif.).

In a typical proliferation assay, each of the overlapping 15-mer peptides is assayed in sextuplicate PBMC cultures derived from 40 naïve donors. Briefly, $2\times10^5$ PBMCs, thawed rapidly before use, are mixed with 5 μM of each peptide and incubated at 37° C. in 5% $CO_2$ for 7 days. As a positive control, samples are incubated with the tetanus toxin derived peptide MQYIKANSKFIGI (SEQ ID NO:59), whereas negative control samples are incubated with 0.5% DMSO. During the last 12 hours of incubation the cultures are pulsed with of [methyl-$^3$H]thymidine (0.5 μCi/well) (NEN Life Science Products, Boston, Mass.), the cultures are harvested onto filter mats and thymidine incorporation is measured as counts per minute (CPM) using a Wallac microplate beta top plate scintillation counter (Perkin Elmer, Boston, Mass.). The stimulatory index for each peptide is calculated by dividing the CPM value of a given peptide divided by the CPM value obtained from negative controls.

It is found that the stimulatory index of the positive control peptide is significantly greater than 1 (the stimulatory index of the negative control), and peptides containing the core sequence LRQFLKMNS (SEQ ID NO:48), FLKMNSTGD (SEQ ID NO:49) or LKMNSTGDF (SEQ ID NO:50), such as, for example peptides ARKLRQFLKMNSTGD (SEQ ID NO:60), LRQFLKMNSTGDFDL (SEQ ID NO:61), or FLKMNSTGDFDLHLL (SEQ ID NO:62), have an increase in stimulatory index. Therefore peptide sequences such as LRQFLKMNS (SEQ ID NO:48) or LKMNSTGDF (SEQ ID NO:50) indeed represent potential T-cell epitopes.

A similar analysis is performed with a series of 15-mer peptides encompassing a region defined by the core peptides ILLNCTGQV (SEQ ID NO:52) and LLNCTGQVK (SEQ ID NO:53), and it is found that these peptide sequences as well represent potential T-cell epitopes.

Example 3

Mapping of CD4+ T Helper Cell Epitopes using Differentiated Human Dendritic Cells (DCs) in Vitro Mature dendritic cells (DCs) are potent antigen-presenting cells (APCs) that present antigenic peptides or whole proteins to T-cells efficiently. Isolated DCs, pulsed with antigenic peptides in vitro, are used to induce primary T-cell responses that can be measured in in vitro proliferation assays. Differentiated DCs are generated, for example by the following procedure: first, human monocytes are generated by allowing PBMCs to adhere to plastic tissue culture flasks or by purifying $CD14^+$ PBMCs with magnetically labeled antibodies (Miltenyi Biotec, Auburn, Calif.). The purified monocytes (0.5 to $1.5\times10^6$ cells/ml) are then cultured in AIM V media (GIBCO BRL, Grand Island, N.Y., U.S.A.) containing 1000 U/ml GM-CSF (Endogen; Woburn, Mass.) and 500 U/ml IL-4 (Endogen; Woburn, Mass.) for 3 days. Subsequently, these immature DCs are pulsed with 5 μg/ml of experimental or control peptides and further incubated with a combination of 1000 U/ml TNF-α (Endogen; Woburn, Mass.), 1000 U/ml GM-CSF and 500 U/ml IL-4 for another 48 hours. Mature DCs are monitored by high surface expression levels of $CD80^+$, $CD86^+$ and HLA-DR.

These mature antigen-pulsed DCs are irradiated with 4200 Rads and are used in a proliferation assay with purified autologous $CD4^+$ T-cells. ($CD4^+$ T-cells are purified with magnetically labeled antibodies (Miltenyi Biotec, Auburn, Calif.), using frozen PBMC aliquots from the same donor that provides monocytes for the in vitro DC differentiation.) In a typical assay, antigen-pulsed DCs ($2\times10^5$/mL) are incubated together with autologous $CD4^+$ T-cells ($2\times10^6$ cells/mL) in round-bottomed 96-well plates at 37° C. in 5% $CO_2$ for 7 days. [methyl-3H]thymidine (NEN Life Science Products, Boston, Mass.) is added during the last 12 hours of incubation at 0.5 μCi/well, the samples are harvested, lysed onto glass filters, and $^3$H-thymidine incorporation is measured in a scintillation counter.

15-mer peptides, as described for Example 1, are tested in this assay and compared to reference peptides and other controls. It is found that this assay is more sensitive than the assay described in Example 1, allowing better differentiation between the ability of individual peptides to induce T-cell proliferation. It is found, that IL-7 peptides containing the core sequences LRQFLKMNS (SEQ ID NO:48), FLKMNSTGD (SEQ ID NO:49), LKMNSTGDF (SEQ ID NO:50), ILLNCTGQV (SEQ ID NO:52) or LLNCTGQVK (SEQ ID NO:53) do indeed induce significant T-cell proliferation and therefore these sequences do represent potential T-cell epitopes.

Example 4

In Vitro Analysis of De-Immunizing Amino Acid Substitutions in IL-7

Amino acid substitutions in the peptide regions described above which are considered to render the IL-7 protein less immunogenic are tested in in vitro assays, as described in Example 1 and Example 2. For example, the variant IL-7 peptide encompassing the sequence LRQFLDDNS (SEQ ID NO:63) is expected to generate a significantly decreased T-cell proliferative response compared to the wild-type parental peptide encompassing LRQFLKMNS (SEQ ID NO:48). Similarly, the variant IL-7 peptide encompassing the sequence TLLNCTGQG (SEQ ID NO:64) is expected to generate a significantly decreased T-cell proliferative response compared to the wild-type parental peptide encompassing ILLNCTGQV (SEQ ID NO:52).

A series of IL-7 derived 15-mer peptides is synthesized that encompass the variant IL-7 sequences LRQFLDDNS (SEQ ID NO:63) or TLLNCTGQG (SEQ ID NO:64), as described in Example 1. In addition, the variant IL-7 proteins, or fusion proteins containing variant IL-7, which include substitutions of the invention are produced either in a prokaryotic or eukaryotic expression system (DeI-IL-7's). For example, a variant IL-7 is produced that includes the amino acid substitutions K68D, M69D, I88T and V94G. (In addition, the prokaryotically produced IL-7 proteins include a start methionine.) These peptides and purified proteins, and their parental counterparts, are tested in their ability to induce T-cell proliferation, in assays with whole PBMC cultures as described in Example 1 or by pulsing human DCs as described in Example 2.25 μg/ml of protein is used to stimulate PBMCs or to pulse DCs.

It is found that in general, peptides derived from the variant IL-7 sequences have a significantly reduced ability to induce T-cell proliferation compared to the corresponding peptides derived from the wild-type human IL-7 protein. Therefore, these variant peptide sequences are much poorer potential T-cell epitopes. Likewise, the bacterially produced variant IL-7 protein also has a reduced ability to induce T-cell proliferation than wild-type IL-7, indicating that these mutated regions may be significant contributors to the immunogenicity of prokaryotically produced IL-7.

Example 5

Analysis of IL-7 Derived Peptides as Potential B-cell Epitopes

For bacterially-produced, unglycosylated human IL-7 protein, sequences surrounding N-linked glycosylation sites of IL-7 may be recognized as "non-self" by the human immune system, and elicit an antibody response. Essentially, to assess if these sequences represent linear B-cell epitopes, peptides spanning these sequences are used to immunize rabbits, and the reactivity of resulting antibodies toward bacterially-produced native human IL-7 and denatured human IL-7 is tested. As a further control, a native eukaryotically-produced glycosylated huFc-IL-7 fusion protein is used.

Methods and materials to raise polyclonal antibodies against a specific peptide antigen in, for example, rabbits, and their subsequent purification are generally known to those skilled in the art, and references thereto may be found, for example, in: Antibodies: A Laboratory Manual, E. Harlow and D. Lane, Cold Spring Harbor Press.

Briefly, in one example, a peptide containing the core sequence FLKMNSTGD (SEQ ID NO:49), such as LRQFLKMNSTGDFDL[C] (SEQ ID NO:65) or [C]LRQFLKMNSTGDFDL (SEQ ID NO:66) is coupled via an added terminal cysteine to three different carrier proteins, keyhole limpet hemocyanin (KLH, EMD Biosciences, San Diego, Calif.), BSA (EMD Biosciences, San Diego, Calif.), and ovalbumin (Pierce, Rockford, Ill.) using a coupling agent such as SMCC (Pierce, Rockford, Ill.), and multiple rabbits are immunized by successive injections with each of the peptide conjugate in the presence of adjuvant. The immune response is boosted with further injections of one of the peptide-carrier conjugates at monthly intervals, and the resulting antiserum from each rabbit is affinity-purified over a Sulfo-Link column (Pierce, Rockford, Ill.) to which the peptide is coupled, and the antibody is further concentrated over a hydroxyapatite column (Bio-Rad Laboratories, Hercules, Calif.).

The purified antibodies are tested against bacterially-produced native human IL-7, denatured human IL-7 and a eukaryotically-produced glycosylated huFc-IL-7 fusion protein in an ELISA assay, following standard procedures. Briefly, ELISA plates, coated with the purified protein preparations, are incubated with the test antibody samples, the plates are washed, incubated with a secondary antibody such as horseradish peroxidase-coupled anti-rabbit IgG, washed again and incubated with a chromogenic substrate solution to indicate the concentration of bound antibody.

Similarly, antibodies are raised to other peptides encompassing the . . . MNSTG . . . (SEQ ID NO:67) glycosylation site (at Asn70) in human IL-7, or to peptides encompassing the . . . LNCTG . . . (SEQ ID NO:68) glycosylation site (at Asn91). Using this approach, it is found that generally the denatured bacterially-produced human IL-7 is well recognized by the antibodies and that the glycosylated huFc-IL-7 fusion protein is not. Peptides that give rise to antibodies reacting with the bacterially-produced native human IL-7 protein indicate that a linear B-cell epitope at the glycosylation site is recognized. It is further found that, in a cell-based proliferation assay as described in Example 9, the antibodies raised against peptides of this Example have the effect of inhibiting IL-7-stimulated cell proliferation. This result indicates that these antibodies have neutralizing activity.

Example 6

Construction of Human IL-7 Variants that Lack Potential T-cell Epitopes

Nucleic acids are constructed that encode versions of human IL-7 variants either suitable for bacterial expression or suitable for eukaryotic expression, for instance as a fusion protein. For example, nucleic acids encoding a mature human IL-7 variant containing the substitutions K6SD, M69D, ISST, and V96G (DeI-IL-7 SEQ ID NO: 4) are constructed, using standard methods familiar to those skilled in the art. SEQ ID NO: 11 shows an example of such a DNA sequence encoding a mature IL-7 variant, DeI-IL-7, with codon substitutions of amino acid residues K68D, M69D, 188T, and V96G.

For bacterial expression, the protein sequence of DeI-IL-7 including a start methionine (bDeI-IL-7, SEQ ID NO: 5) is reverse-translated using a codon bias appropriate for optimal *E. coli* expression. The resulting nucleic acid sequence is further adapted to include desired (or to exclude undesired) features such as a stop codon or restriction sites, and sequences are added that facilitate cloning into a bacterial expression vector, for example an appropriate vector from the pET series (EMD Biosciences, San Diego, Calif.). The nucleic acid sequence is synthesized by total gene synthesis (Blue Heron Biotechnology, Bothell, Wash.) and inserted into the expression vector. An example of a DNA sequence encoding bDeI-IL-7, codon-optimized for *E. coli* with codon substitutions of amino acid residues K68D, M69D, 188T, V96G, is shown in SEQ ID NO:10.

For eukaryotic expression as a huFc-DeI-IL-7 fusion protein, the nucleic acid sequence of the mature human IL-7 is modified to incorporate codons for desired amino acid mutations of the invention as described above. (See e.g. SEQ ID NO:11). The sequence is further adapted to incorporate flanking sequences with unique restriction sites for insertion as a Xma I/Xho I fragment in-frame into a pdCs-huFc expression vector encoding the hinge, CH2 and CH3 region of IgGi (see Lo et al., (1998), *Protein Engineering* 11:495), and is synthesized by total gene synthesis (Blue Heron Biotechnology, Bothell, Wash.). The synthetic Xma I/Xho I DeI-IL-7 fragment is then cloned into the pdCs-huFc vector, yielding an expression plasmid encoding huFc-DeI-IL-7. Other IL-7 and Fc-IL-7 variants of the invention can be produced by similar methods.

Specifically, nucleic acids encoding the human deimmunized Fc-IL-7 fusion proteins huFcγ2(h)(FN>AQ)-(linker2)-IL-7(PNS) and huFcγ2(h)(FN>AQ)-(linker2)-IL-7(PNDS) were generated as follows. huFcγ2(h)(FN>AQ)-(linker2)-IL-7(PNS) is a human Fc-IL-7 fusion protein comprising the N-terminus of human IL-7 genetically fused to the C-terminus of a human IgG2 Fc domain with an IgG1 hinge via a linker sequence GGGGSGGGG (SEQ ID NO:17). The Fc portion contains the mutations Phe296Ala and Asn297Gln. The IL-7 portion contains the mutations F39P, F57N and L128S. huFcγ2(h)(FN>AQ)-(linker2)-IL-7(PNDS) is the same as huFcγ2(h)(FN>AQ)-(linker2)-IL-7(PNS), but for containing an additional mutation in the IL-7 moiety, L77D. The sequence also contains codons for the mutation of the LSLS (SEQ ID NO:57) sequence near the C-terminus of the Fc portion to be replaced by ATAT (SEQ ID NO:58). In addition, the nucleic acid sequence includes a codon to replace the C-terminal lysine of the Fc portion with an alanine residue.

A nucleic acid of the sequence presented in SEQ ID NO:29 was synthesized de novo (Blue Heron Biotechnology, Bothell, Wash.), which encodes the linker sequence GGGGSGGGG (SEQ ID NO:17) followed by mature human IL-7 containing the amino acid substitutions F39P, F57N, and L128S (IL-7(PNS)) and which contains flanking restriction sites Xma I and Xho I at the 5'- and 3' ends, respectively. This purified Xma I/Xho I fragment was ligated to a likewise digested and purified vector fragment of the pdCs-huFc series, pdC10-huFcγ2(h)(FN>AQ), generating a plasmid encoding huFcγ2(h)(FN>AQ)-(linker2)-IL-7(PNS). Lo et al., (1998), *Protein Engineering* 11:495. The coding sequence was ascertained by sequencing.

The further introduction of the substitution L77D into IL-7 (PNS) was performed by standard PCR mutagenesis methods, using mutagenic primers M(s) (5'-TGACTTTGAT GACCACCTGTTAAAAGTTTC-3' (SEQ ID NO:69); mutated codon underlined) and M(a) (5'-AACAGGTG GTCATCAAAGTCACCAGTGC-3' (SEQ ID NO:70)). Briefly, separate PCR reactions were performed on a plasmid template containing (linker2)-IL-7(PNS), one with M(s) and the downstream primer 5'-CTCGAGTCAGTGTTCTT-TAGTGCCCATC-3' (SEQ ID NO:71) the other with M(a) and the upstream primer 5'-CCCGGGTGCTGGAGGTG-GAGGATCAGGTG-3' (SEQ ID NO:72), the PCR fragments were purified and combined as the template for a secound round of PCR using again the upstream primer 5'-CCCGGGTGCTGGAGGTGGAGGATCAGGTG-3' (SEQ ID NO:72) and the downstream primer 5'-CTCGAGT-CAGTGTTCTTTAGTGCCCATC-3' (SEQ ID NO:73). The resultant purified fragment was inserted into a TA cloning vector pCR2.1 ((Invitrogen, Carlsbad, Calif.), and its sequence was confirmed. An Xma I/Xho I fragment encoding (linker2)-IL-7(PNDS) was excised, and ligated to a likewise digested and purified vector fragment of the pdCs-huFc series, pdC10-huFcγ2(h)(FN>AQ), generating a plasmid encoding huFcγ2(h)(FN>AQ)-(linker2)-IL-7(PNDS).

Similarly, plasmids encoding variants of these fusion proteins differing in the Fc moiety are obtained; for example a plasmid encoding huFcγ2(h)(linker2)-IL-7(PNDS) is obtained by ligating an Xma I/Xho I fragment encoding (linker2)-IL-7(PNDS) to a likewise digested and purified vector fragment of the pdCs-huFc series, pdC10-huFcγ2(h).

Example 7

Expression and Purification of IL-7 Variants

For eukaryotic expression of the huFc-DeI-IL-7 fusion protein, electroporation is used to introduce the DNA encoding the fusion protein into a mouse myeloma NS/0 cell line. To perform electroporation NS/0 cells are grown in Dulbecco's modified Eagle's medium supplemented with 10% heat-inactivated fetal bovine serum, 2 mM glutamine and penicillin/streptomycin. About $5\times10^6$ cells are washed once with PBS and resuspended in 0.5 ml PBS. 10 μg of linearized plasmid DNA for huFc-DeI-IL-7 is then incubated with the cells in a Gene Pulser Cuvette (0.4 cm electrode gap, BioRad) on ice for 10 min. Electroporation is performed using a Gene Pulser (BioRad, Hercules, Calif.) with settings at 0.25 V and 500 μF. Cells are allowed to recover for 10 min on ice, after which they are resuspended in growth medium and plated onto two 96 well plates.

Stably transfected clones are selected by their growth in the presence of 100 nM methotrexate (MTX), which is added to the growth medium two days post-transfection. The cells are fed every 3 days two to three more times, and MTX-resistant clones appear in 2 to 3 weeks. Supernatants from clones are assayed by anti-Fc ELISA to identify clones that produced high amounts of the IL-7 fusion protein. High producing clones are isolated and propagated in growth medium containing 100 nM MTX. Typically, a serum-free growth medium, such as H-SFM or CD medium (Life Technologies), is used.

A standard purification of Fc-containing fusion proteins is performed based on the affinity of the Fc protein moiety for Protein A. Briefly, NS/0 cells expressing the fusion protein, such as huFc-DeI-IL-7, are grown in tissue culture medium and the supernatant containing the expressed protein is collected and loaded onto a pre-equilibrated Fast Flow Protein A Sepharose column. The column is then washed extensively with buffer (such as 100 MM sodium phosphate, 150 mM NaCl at neutral pH). Bound protein is eluted at a low pH (pH 2.5-3) in same buffer as above and fractions are immediately neutralized.

Bacterial expression and purification of bDeI-IL-7 is performed essentially as described by Cosenza et al. for bacterially-produced IL-7 (see Cosenza et al., (1997) *JBC,* 272: 32995). In essence, bDeI-IL-7 is isolated from inclusion bodies, denatured and refolded. Briefly, bacterial expression cultures transformed with the expression vector encoding, for example, bDeI-IL-7 are grown to mid-log phase and recombinant protein expression is induced. Following induction, the bacteria are harvested and lysed by sonication, and inclusion bodies are isolated in buffer A (50 mM Tris HCl (7.5), 5 mM EDTA, 20% sucrose). After extensive washes, the inclusion bodies are resuspended in a guanidine denaturation buffer (50 mM Tris-HCl (pH8.0), 5 M guanidine HCl, 5 mM EDTA), briefly sonicated and reduced in 6 mM DTT. Denatured bDeI-IL-7 protein is then further purified by denaturing size exclusion HPLC. The protein is then refolded in refolding buffer (50 mM glycine, 30 mM NaOH, 0.4 M L-arginine, 1 mM DTT, pH 10), dialyzed into a phosphate buffer, and further purified by size exclusion HPLC.

Example 8

Biochemical Analysis of IL-7 Variants

The effect of the introduced mutations on the integrity of IL-7 proteins is assessed by routine reducing and non-reducing SDS-PAGE analysis and size exclusion chromatography.

For example, the fusion protein huFc-DeI-IL-7, expressed from NS/0 cells, is captured on Protein A Sepharose beads (Repligen, Needham, Mass.) from the tissue culture medium into which it is secreted, and eluted by boiling in protein sample buffer, with or without a reducing agent such as β-mercaptoethanol. The sample is fractionated by SDS-PAGE and the protein bands are visualized by Coomassie staining. It is expected that a fusion protein containing IL-7 mutations that sufficiently interfere with proper folding is more likely to show degradation products by SDS-PAGE.

Purified huFc-DeI-IL-7 is also analyzed by size exclusion chromatography (SEC) to assess the extent to which the fusion protein is aggregated. Briefly, the cell culture supernatant is loaded onto a pre-equilibrated Fast-Flow Protein A Sepharose column, the column is washed extensively in a physiological buffer (such as 100 mM Sodium Phosphate, 150 mM NaCl at neutral pH), and the bound protein is eluted at about pH 2.5 to 3 in same salt buffer as above. Fractions are immediately neutralized, peak fractions are pooled, and an aliquot is fractionated over an analytical SEC column.

Example 9

In Vitro Activity of IL-7 Variants

To determine whether the IL-7 variants containing mutations of the invention retain their cytokine activity in vitro cellular proliferation bioassays are performed. Human PBMC (Peripheral Blood Mononuclear Cells) are activated by PHA-P to produce cells which are responsive to IL-7. Proliferation is measured in a standard thymidine incorporation assay.

For example, the cytokine activity of huFc-DeI-IL-7 and bDeI-IL-7 is determined. Briefly, PBMC's are first incubated for five days with 10 microgram/ml PHA-P, cells are washed and then incubated in medium with huFc-DeI-IL-7 or bDeI-IL-7, prepared as a dilution series, for a total of 48 hours. During the final 12 hours, the samples are pulsed with 0.3 μCi of [methyl-3H]thymidine (Dupont-NEN-027). Cells are then washed extensively, harvested and lysed onto glass filters. $^3$H-thymidine incorporated into DNA is measured in a scintillation counter. As a standard, wild type huIL-7 protein, obtained from R&D Systems (Minneapolis, Minn.), or obtained from the National Institute for Biological Standards and Control (NIBSC), is assayed.

An ED50 value of cell proliferation for huFc-DeI-IL-7 or bDeI-IL-7 is obtained from plotting a dose response curve according to standard techniques, and determining the protein concentration that results in half-maximal response.

Example 10

Induction of Anti-Human IL-7 Antibodies in Monkeys by Wild-Type IL-7 and IL-7 Variants It is known that bacterial-derived wild-type human IL-7 administered to monkeys often results in neutralizing anti-human IL-7 antibody titers (Storek et al., (2003), *Blood,* 101:4209; Fry et al., (2003), *Blood,* 101:2294). Thus, the propensity of prokaryotically produced variant IL-7 and wild-type IL-7 proteins, as well as eukaryotically produced fusion proteins containing wild-type or variant IL-7 polypeptides, to induce neutralizing antibodies in nonhuman primates is assessed. In a typical experiment, rhesus macaques are injected with 40 μg/kg of the protein samples subcutaneously once a day for four weeks. For example, the protein samples are commercially available prokaryotically-produced IL-7 (PeproTech, Rocky Hill, N.J.), the prokaryotically produced variant IL-7(K68D, M69D, I88T, V94G), and the equivalent Fc-IL-7 fusion proteins produced in a mammalian expression system. At regular intervals, serum is obtained from the animals, and serum concentrations of antibodies against human IL-7 are measured by ELISA using human IL-7 coated 96 well plates (Nunc, Naperville, Ill.). Typically, serial dilutions of each serum sample are added to each well in triplicate for two hours, washed with 0.05% Tween (Tween 20) in PBS and blocked with 1% BSA/1% goat serum in PBS. To each sample a horseradish peroxidase-conjugated anti-macaque IgG is added (1:60,000 in sample buffer), incubated at 37° C. for 2 hr, and the plate is washed 8 times with 0.05% Tween in PBS. Samples are then assayed using the colorimetric substrate solution OPD (o-phenylenediamine dihydrochloride) by measuring the OD at 490 nm, subtracting the background OD reading at 650 nm.

It is found that prokaryotically produced wild-type IL-7 protein indeed gives rise to high anti-IL-7 antibody titers. In contrast, the antibody titers of the prokaryotically produced variant IL-7 gives rise to significantly lower titers of anti IL-7 antibodies. It is also found that the differences in the levels of anti IL-7 antibody titers produced by animals administered mammalian produced wild-type and variant Fc-IL-7 fusion proteins, (with mutations around the N-linked glycosylation sites) are not as pronounced. This result may indicate that the lack of glycosylation at these sites in the prokaryotically produced proteins contributes to the immunogenicity of these proteins.

Example 11

Acute Tolerability of Fc-IL-7 in Immunocompetent Mice

The Fc-IL-7 fusion protein huFcγ2(h)(FN>AQ)(linker2)-huIL-7 was prepared according to the method described in Example No. 6, purified, then formulated in 50 mM phosphate, 150 mM sodium chloride pH 7.00, 0.05% (v/v) Tween 80. (The FN>AQ mutations are noted in the figures alternatively as N≧Q). The protein concentrations of diluted solutions were determined using the absorbance at 280 nm and the theoretical extinction coefficient of 0.98 mg/$OD_{280}$, based on the known protein sequence. For dosing mice, an aliquot of each sample was removed from stock vials and diluted with 0.9% saline within one hour of dosing.

C57B 1/6 mice (Charles River Laboratories, Wilmington, Mass.), 17 weeks of aged were divided into groups of 2 mice each and were administered the Fc-IL-7 fusion proteins subcutaneously for 5 consecutive days. Groups received dosages of either 0.5, 5.0, 25 mg/kg or the vehicle control each day. All mice survived the treatment through day 7, at which point the mice were sacrificed.

Fc-IL-7 plasma levels were determined by obtaining blood samples from the retro-orbital sinus 6 hours after dosing on days 0, 2, 4, and 7. Blood samples were collected in tubes containing heparin to prevent clotting. Cells were removed by centrifugation and the concentration of intact Fc-IL-7 fusion protein in the plasma was measured using standard ELISA procedures. Plasma levels of Fc-IL-7 in μg/μl for test mice are shown in FIG. 5. The plasma of mice showed a dose dependent increase in Fc-IL-7 concentration at all time points tested and further increased following each dose. However, as shown in FIG. 6 the magnitude of the increase lessened after each dosing.

The functional activity of Fc-IL-7 was confirmed by measuring increases in B cells and T cells on day 7 following the initiation of dosing. Since IL-7 boosts the production of immune effector cells such as B cells and T cells, the cellularity and weight of the spleen is expected to increase. Mice were sacrificed on day 7 and organs were removed and weighed. FIG. 7 shows the average organ weights on day 7. As expected, spleen weight increased 3 to 5 fold 1 week after the initial dose. Lung weights increased 2 fold following the 2 higher doses of Fc-IL-7 due to lymphotcytic infiltration. No weight changes were observed in the kidney or liver.

Figure 8:
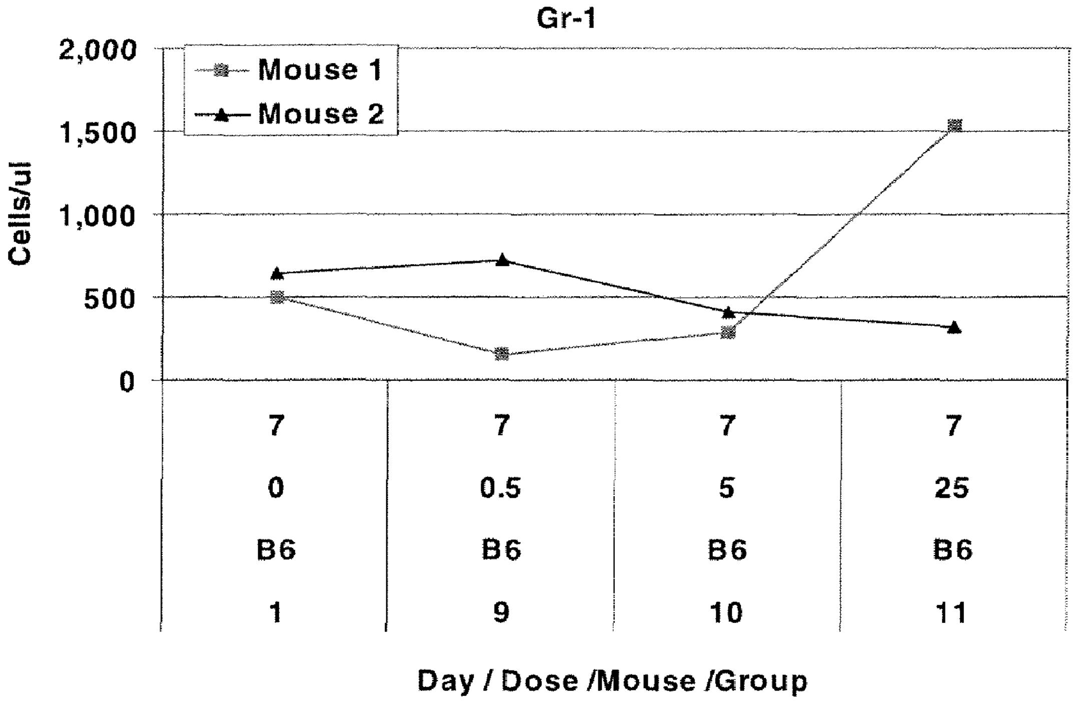
FIG. 8 depicts a comparison of the frequency of granulocyte Gr-1+ cells in cells/μL in the peripheral blood of mice from the control group, 0.5 mg/kg dosage group, 5.0 mg/kg dosage group, and 25 mg/kg dosage group on day 7.
Figure 9:
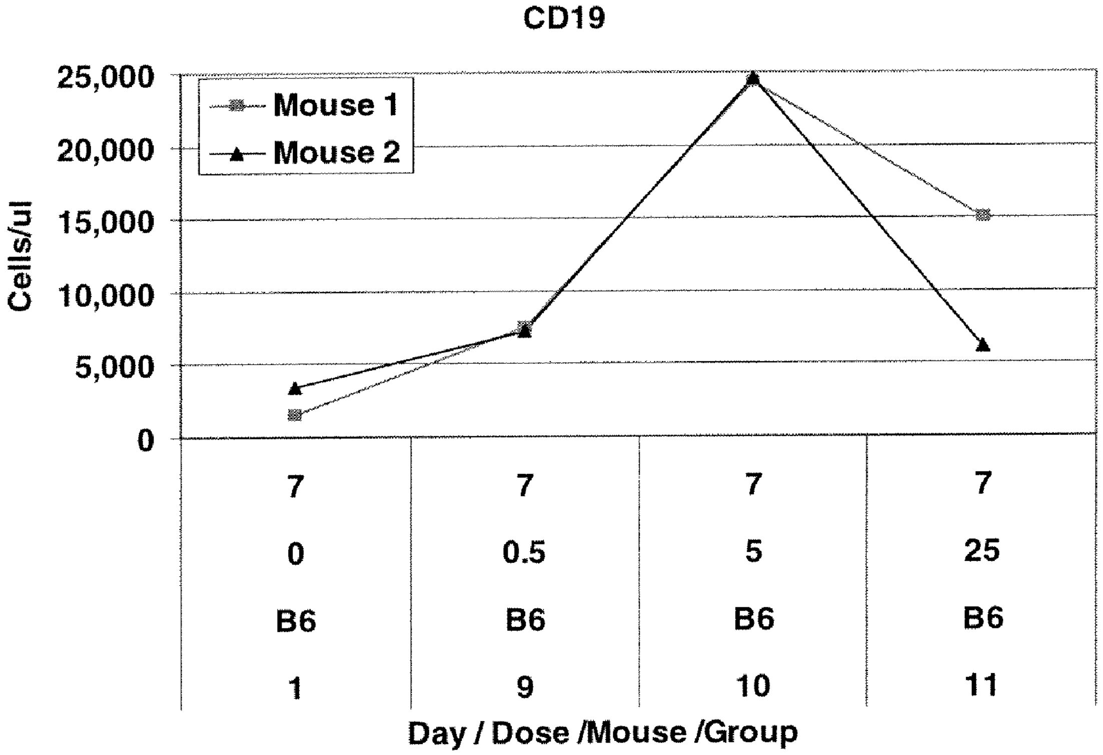
FIG. 9 depicts a comparison of the frequency of CD 19+ cells in cells/μL in the peripheral blood of mice from the control group, 0.5 mg/kg dosage group, 5.0 mg/kg dosage group, and 25 mg/kg dosage group on day 7.
Figure 10:
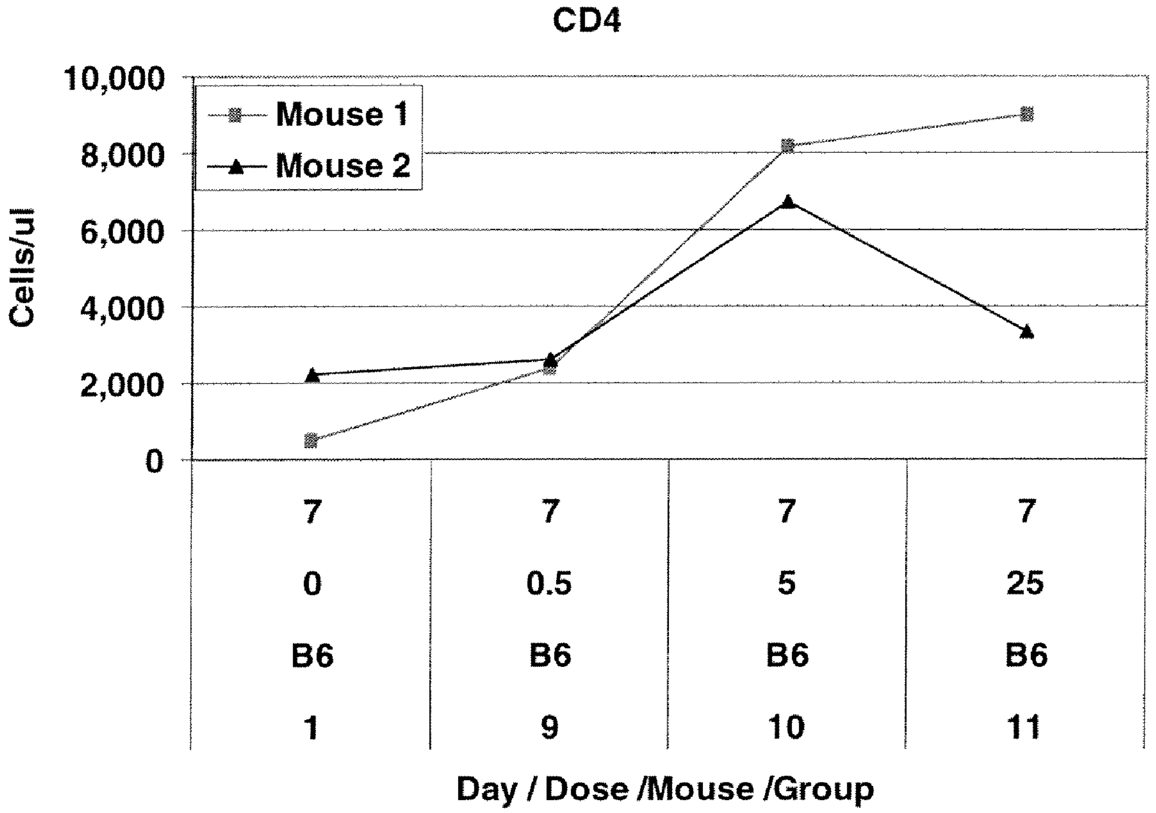
FIG. 10 depicts a comparison of the frequency of CD4+ cells in cells/μL in the peripheral blood of test from the control group, 0.5 mg/kg dosage group, 5.0 mg/kg dosage group, and 25 mg/kg dosage group on day 7.
Figure 11:
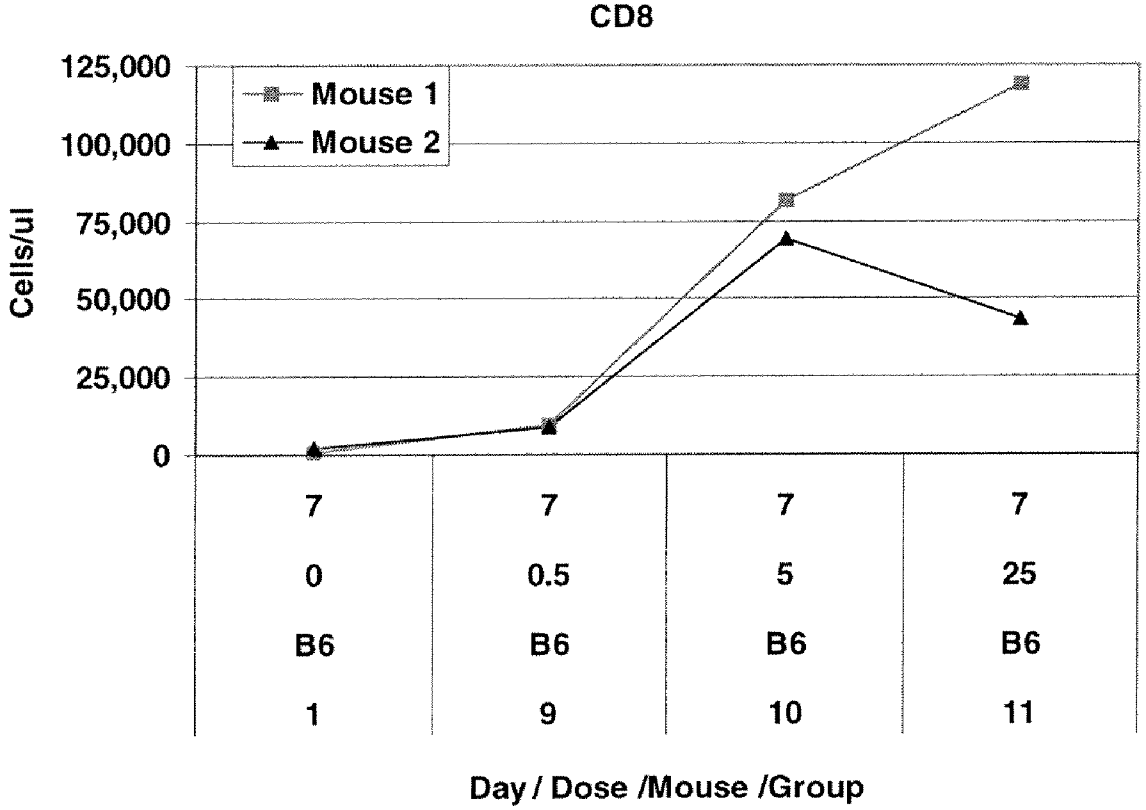
FIG. 11 depicts a comparison of the frequency of CD8+ cells in cells/μL in the peripheral blood of test from the control group, 0.5 mg/kg dosage group, 5.0 mg/kg dosage group, and 25 mg/kg dosage group on day 7.

The response of B cells (CD19+, CD4+, CD8+ and granulocytes (Gr-1+)) in all groups was observed on day 7. FIG. 8 shows the frequency of Gr-1+ cells in the peripheral blood of two mice in each group. As the data shows, granulocytes were generally unresponsive to Fc-IL-7. FIG. 9 shows the frequency of CD19+ cells in the peripheral blood of two mice in each group. FIG. 10 shows the frequency of CD4+ cells in the peripheral blood of two mice in each group, while FIG. 11 shows the frequency of CD8+ cells in the peripheral blood of two mice in each group. The increases in B cell (FIG. 9) and T cell (FIGS. 10 and 11) numbers were maximal for the 5 mg/kg dosage group with each mouse tested showing significantly increased T cell and B cell numbers over the control group and the 0.5 mg/kg dosage group. However, T cell numbers either declined or increased for mice in the 25 mg/kg dosage group. All measurements of cells are shown in cells per μL of blood.

Example 12

Assessment of Human Fc-IL-7 Activity

Figure 12:
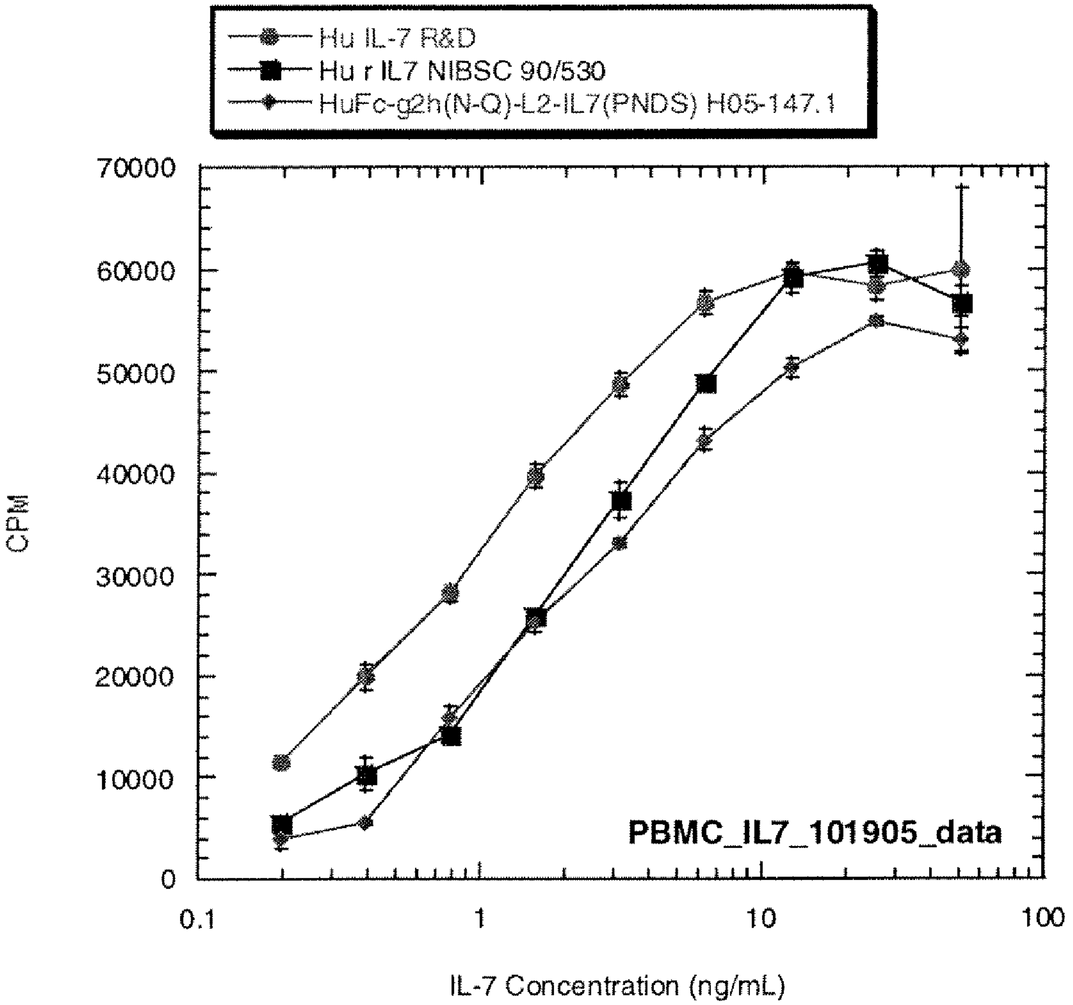
FIG. 12 depicts the activity of Fc-IL-7 as compared to wild type IL-7 based on incorporation of tritiated thymidine in counts per minute versus IL-7/Fc-IL-7 concentration in a standard cell proliferation assay.

The biological activity of the Fc-IL-7 fusion protein tested in Example 11 was measured by tritiated thymidine uptake in a standard cell proliferation assay using peripheral blood mononuclear cell (PBMC) PHA blasts according to the method described in Yokota et al., (1986), *Proc. Natl. Acad. Sci. USA,* 83:5894; and Stern etal., (1990), *Proc. Natl. Acad. Sci. USA,* 87:6808-68 12, with human IL-7 used as a standard. As shown in FIG. 12, cellular proliferation as measured by the uptake of tritiated thymidine for the Fc-IL-7 molecule is similar to that of the standard NIBSC human IL-7 (World Health Organization), indicating that the activity of the Fc-IL-7 molecule is similar to wild-type human IL-7 in a standard cell proliferation assay.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. An isolated polypeptide comprising an amino acid sequence at least 97% identical to mature human IL-7, wherein the polypeptide comprises two or more amino acid substitutions, wherein the substitutions are at positions selected from the group consisting of Phe39, Phe57, Leu77, and Leu 128.

2. The polypeptide of claim 1, wherein the amino acid substitutions comprise two or more of Phe39Pro, Phe57Asn, Leu77Asp, and Leu128Ser.

3. The polypeptide of claim 1, wherein the amino acid substitutions comprise the substitutions Phe39Pro, Phe57Asn, and Leu128Ser.

4. The polypeptide of claim 1, further comprising at least an Fc portion of an antibody.

5. The polypeptide of claim 4, wherein the Fc portion is a human Fc portion.

6. The polypeptide of claim 4, wherein the Fc portion is an IgG2 Fc portion.

7. The polypeptide of claim 1, wherein the polypeptide comprises amino acid substitutions at amino acid residues corresponding to positions Phe39, Phe57, Leu77, and Leu 128 of mature human IL-7.

8. An isolated polypeptide comprising the amino acid sequence of SEQ ID NO:9.

* * * * *